US009796756B2

(12) United States Patent
Hadwiger et al.

(10) Patent No.: US 9,796,756 B2
(45) Date of Patent: *Oct. 24, 2017

(54) GALACTOSE CLUSTER-PHARMACOKINETIC MODULATOR TARGETING MOIETY FOR SIRNA

(71) Applicant: Arrowhead Madison Inc., Madison, WI (US)

(72) Inventors: Philipp Hadwiger, Kulmbach (DE); Torsten Hoffmann, Weil am Rhein (DE); Eric A Kitas, Aesch BL (CH); Peter Mohr, Basel (CH); Ingo Roehl, Memmelsdorf (DE); Linda Valis, Neuoetting (DE); David B Rozema, Middleton, WI (US); David L Lewis, Madison, WI (US); Darren H Wakefield, Fitchburg, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/972,385

(22) Filed: Dec. 17, 2015

(65) Prior Publication Data

US 2016/0102120 A1 Apr. 14, 2016

Related U.S. Application Data

(62) Division of application No. 13/327,271, filed on Dec. 15, 2011, now Pat. No. 9,249,179.

(60) Provisional application No. 61/424,195, filed on Dec. 17, 2010.

(51) Int. Cl.
| | | |
|---|---|---|
| *A61K 47/26* | (2006.01) | |
| *A61K 48/00* | (2006.01) | |
| *C07K 5/113* | (2006.01) | |
| *C07H 21/02* | (2006.01) | |

(52) U.S. Cl.
CPC ........... *C07K 5/1021* (2013.01); *C07H 21/02* (2013.01)

(58) Field of Classification Search
USPC ....... 435/6.1, 91.1, 91.31, 455, 458; 514/44; 530/397; 536/23.1, 24.5
See application file for complete search history.

(56) References Cited

U.S. PATENT DOCUMENTS

| | | | |
|---|---|---|---|
| 5,885,968 A | 3/1999 | Biessen et al. | |
| 6,525,031 B2 | 2/2003 | Manoharan | |
| 9,249,179 B2* | 2/2016 | Hadwiger | C07K 5/1021 |
| 2004/0162260 A1 | 8/2004 | Rozema et al. | |
| 2008/0152661 A1 | 6/2008 | Rozema et al. | |
| 2008/0281074 A1 | 11/2008 | Rozema et al. | |
| 2009/0264636 A1 | 10/2009 | Vargeese et al. | |
| 2010/0015218 A1 | 1/2010 | Jadhav et al. | |
| 2010/0130592 A1 | 5/2010 | McSwiggen et al. | |
| 2010/0144831 A1 | 6/2010 | Fakhral et al. | |
| 2011/0124853 A1 | 5/2011 | Chen et al. | |
| 2011/0207799 A1 | 8/2011 | Rozema et al. | |
| 2011/0269814 A1 | 11/2011 | Manoharan et al. | |
| 2013/0178512 A1 | 7/2013 | Manoharan et al. | |
| 2016/0222384 A1 | 8/2016 | Lewis et al. | |

FOREIGN PATENT DOCUMENTS

WO 2009126933 A2 10/2009

OTHER PUBLICATIONS

Fourth Office Action for corresponding Chinese Application No. 201180060354.X.
Amarzguioui et al. "An algorithm far selection of functional siRNA sequences" Biochemical and Biophysical Research Communications (2004) 316: 1050-1058.
Baenziger JU et al. "Galactose and N-acetylgalactosamine-specific endocytosis of glycopeplides by isolated rat hepatocytes" Cell (1980) 22(2): 611-620.
Biessen et al. "Synthesis of Cluster Galactosides with High Affinity for the Hepatic Asialoglycoprotein Receptor" Journal of Medicinal Chemistry (1995) 38(9): 1538-1546.
Chalk et al. "Improved and automated prediction of effective siRNA" Biochemical and Biophysical Research Communications 2004 vol. 319, p. 264-274.
Connolly et al. "Binding and endocytosis of cluster glycosides by rabbit hepatocytes. Evidence for a short-circuit pathway that does not lead to degradation" Journal of Biological Chemistry (1982) 257(2): 939-945.
Frier et al. "Improved free-energy parameters far predictions of RNA duplex stability" Proceedings of the National Academy of Sciences USA (1986) 83: 9373-9377.
Heale et al. "siRNA target site secondary structure predictions using local stable substructures" Nucleic Acids Research (2005) 33(3).
Hean et al.; "Inhibition of hepatitis B virus replication in vivo using lipoplexes containing altritol-modified antiviral siRNAs."; Artif DNA PNA XNA ; Jul. 2010; 1(1):17-26.
Iobst ST et al. "Selective Sugar Binding to the Carbohydrate Recognition Domains of the Rat Hepatic and Macrophage Asialoglycoprotein Receptors." Journal of Biological Chemistry (1996) 271(12), p. 6686-6693.
Khvorova et al. "Functional siRNAs and miRNAs Exhibit Strand Bias" Cell (2003) 115: 209-216.
Kirby AJ "Effective Molarities for Intramolecular Reactions" Advances in Physical Organic Chemistry (1980) p. 183-278.
Pillai et al. "Repression of protein synthesis by miRNAs: how many mechanisms?" Trenos in Cell Biology (2007) 17 (3): 118-126.

(Continued)

*Primary Examiner* — Jane Zara
(74) *Attorney, Agent, or Firm* — Robert Michael Teigen

(57) ABSTRACT

The present invention is directed compositions for targeted delivery of RNA interference (RNAi) polynucleotides to cell in vivo. The pharmacokinetic modulator improve in vivo targeting compared to the targeting ligand alone. Targeting ligand-pharmacokinetic modulator targeting moiety targeted RNAi polynucleotides can be administered in vivo alone or together with co-targeted delivery polymers.

20 Claims, 7 Drawing Sheets

(56) References Cited

OTHER PUBLICATIONS

Pei et al. "On the art of identifying effective and specific siRNAs" Nature Methods (2006) 3(9): 670-676.
Rozema DB et al. "Endosomolysis by Masking of a Membrane-Active Agent (EMMA) for Cytoplasmic Release of Macromolecules" Bioconjugate Chemistry (2003) 14(1): 51-57.
Rozema et al. "Dynamic PolyConjugates for targeted in vivo delivery of siRNA to hepatocytes." Proc Natl Acad Sci USA (2007) 104(32):12982-12987.
Schwarz et al. "Asymmetry in the Assembly of the RNAi Enzyme Complex" Cell (2003) 115: 199-208.
Turner et al. "Free Energy Increments for Hydrogen Bonds in Nucleic Acid Base Pairs" Journal of the American Chemical Society (1987) 209: 3783-3785.
Ui-Tei et al. "Guidelines for the selection of highly effective siRNA sequences for mammalian and chick RNA Interference" Nucleic Acids Research (2004) 32(3): 936-948.
Wincott F et al. "Synthesis, deprotection, analysis and purification of RNA and ribozymes" Nucleic Acids Research (1995) 23(14): 2677-2684.
Wolfrum et al.; "Mechanisms and optimization of in vivo delivery of lipophilic siRNAs."; Nature Biotechnology; 2007; 25(10):1149-1157.
Decision of Rejection for corresponding Japanese Application No. 2013-544786; Dispatch Date of Feb. 10, 2016.
Notice of Reasons for Rejection for corresponding Japanese Application No. 2013-544786; Dispatch Date of Jun. 24, 2015.
Examination Report for corresponding Israeli Application No. 226968.
First Office Action for corresponding Chinese Application No. 201180060354.X.
Second Office Action for corresponding Chinese Application No. 201180060354.X.
Patent Examination Report No. 1 for corresponding Australian Application No. 2011343664.
Office Action for corresponding Russian Application No. 2013117288.
European Search Report and Opinion for corresponding Application No. 11848708.1.
International Search Report for corresponding Application No. PCT/US11/65210.
Further Examination Report for corresponding New Zealand Application No. 609537 dated Jul. 23, 2014.
Further Examination Report for corresponding New Zealand Application No. 609537 dated Nov. 14, 2014.
Shim et al.; "Efficient and targeted delivery of siRNA in vivo"; The FEBS Journal; 227; pp. 4814-4827; 2010.
European Search Report and Opinion for corresponding Application No. 17157064.1 dated Apr. 5, 2017.
Crombez et al.; "Targeting cyclin B1 Through peptide-based delivery of siRNA prevents tumour growth"; Nucleic Acids Research; vol. 37; No. 14; pp. 4556-4569; (2009).
Kim et al.; "Cholesteryl Oligoarginine Delivering Vascular Endothelial Growth Factor siRNA Effectively Inhibits Tumor Growth in Colon Adenocarcinoma"; Molecular Therapy; vol. 14; No. 3: pp. 343-350; (2006).
LeBeau et al.; "Targeting the cancer stroma with a fibroblast activation protein-activated promelittin protoxin"; Mol. Cancer Ther.; 2009; 8(5): 1378-1386.
Reynolds et al. "Rational siRNA design for RNA interference"; Nature Biotechnology, Advance Online Publication; Published online Feb. 1, 2004; Published online at http://www.nature.com/naturebiotechnology/.

\* cited by examiner

```
                       SEQUENCE LISTING

<160> NUMBER OF SEQ ID NOS: 32

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaaucuuau auuugaucca a                                           21

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uuggaucaaa uauaagauuc ccu                                         23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ggaucaucuc aagucuuact t                                           21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
guaagacuug agaugaucct t                                           21

<210> SEQ ID NO 5
<211> LENGTH: 26
<212> TYPE: PRT
<213> ORGANISM: Unknown
<220> FEATURE:
<223> OTHER INFORMATION: Description of Unknown: Melittin peptide
```

```
<400> SEQUENCE: 5

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 6
<211> LENGTH: 27
<212> TYPE: PRT
<213> ORGANISM: Unknown
<220> FEATURE:
<223> OTHER INFORMATION: Description of Unknown: Melittin peptide

<400> SEQUENCE: 6

Gly Ile Gly Ala Val Leu Lys Val Leu Thr Thr Gly Leu Pro Ala Leu
1               5                   10                  15

Ile Ser Trp Ile Ser Arg Lys Lys Arg Gln Gln
            20                  25

<210> SEQ ID NO 7
<211> LENGTH: 25
<212> TYPE: PRT
<213> ORGANISM: Unknown
<220> FEATURE:
<223> OTHER INFORMATION: Description of Unknown: Melittin peptide

<400> SEQUENCE: 7

Gly Ile Gly Ala Arg Leu Lys Val Leu Thr Thr Gly Leu Pro Arg Ile
1               5                   10                  15

Ser Trp Ile Lys Arg Lys Arg Gln Gln
            20                  25

<210> SEQ ID NO 8
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 8

Gly Ile Gly Ala Ile Leu Lys Val Leu Ser Thr Gly Leu Pro Ala Leu
1               5                   10                  15

Ile Ser Trp Ile Lys Arg Lys Arg Gln Glu
            20                  25

<210> SEQ ID NO 9
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 9

Gly Ile Gly Ala Val Leu Lys Val Leu Thr Thr Gly Leu Pro Ala Leu
1               5                   10                  15

Ile Gly Trp Ile Lys Arg Lys Arg Gln Gln
            20                  25

<210> SEQ ID NO 10
<211> LENGTH: 26
<212> TYPE: PRT
<213> ORGANISM: Unknown
<220> FEATURE:
<223> OTHER INFORMATION: Description of Unknown: Melittin peptide
```

```
<400> SEQUENCE: 10

Gly Ile Gly Ala Val Leu Lys Val Leu Ala Thr Gly Leu Pro Ala Leu
1               5                   10                  15

Ile Ser Trp Ile Lys Arg Lys Arg Gln Gln
            20                  25

<210> SEQ ID NO 11
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 11

Gly Ile Gly Ala Val Leu Lys Val Leu Ser Thr Gly Leu Pro Ala Leu
1               5                   10                  15

Ile Ser Trp Ile Lys Arg Lys Arg Gln Gln
            20                  25

<210> SEQ ID NO 12
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 12

Gly Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 13
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 13

Tyr Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 14
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 14

Gly Ile Gly Ala Ile Leu His Val Leu Ala Thr Gly Leu Pro Thr Leu
1               5                   10                  15

Ile Ser Trp Ile His His His His Gln Gln
            20                  25

<210> SEQ ID NO 15
<211> LENGTH: 26
<212> TYPE: PRT
<213> ORGANISM: Unknown
<220> FEATURE:
```

<223> OTHER INFORMATION: Description of Unknown: Melittin peptide

<400> SEQUENCE: 15

Gly Ile Gly Ala Ile Leu Lys Val Leu Ala Thr Gly Leu Pro Thr Leu
1               5                   10                  15

Ile Ser Trp Ile Arg Asn Arg Arg Gln
            20                  25

<210> SEQ ID NO 16
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 16

Gly Ile Gly Ala Ile Leu Arg Val Leu Ala Thr Gly Leu Pro Thr Leu
1               5                   10                  15

Ile Ser Trp Ile Lys Asn Lys Arg Lys Gln
            20                  25

<210> SEQ ID NO 17
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 17

Gly Ile Gly Ala Ile Leu Lys Val Leu Ala Thr Gly Leu Pro Thr Leu
1               5                   10                  15

Ile Ser Trp Ile Lys Arg Lys Arg Lys Gln
            20                  25

<210> SEQ ID NO 18
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 18

Gly Ile Gly Ala Ile Leu Lys Val Leu Ala Thr Gly Leu Pro Thr Leu
1               5                   10                  15

Ile Ser Trp Ile Lys Lys Lys Lys Gln Gln
            20                  25

<210> SEQ ID NO 19
<211> LENGTH: 32
<212> TYPE: PRT
<213> ORGANISM: Unknown
<220> FEATURE:
<223> OTHER INFORMATION: Description of Unknown: Melittin peptide

<400> SEQUENCE: 19

Gly Ile Gly Ala Ile Leu Lys Val Leu Ala Thr Gly Leu Pro Thr Leu
1               5                   10                  15

Ile Ser Trp Ile Lys Asn Lys Arg Lys Gln Gly Ser Lys Lys Lys Lys
            20                  25                  30

<210> SEQ ID NO 20
<211> LENGTH: 28
<212> TYPE: PRT
<213> ORGANISM: Unknown

```
<220> FEATURE:
<223> OTHER INFORMATION: Description of Unknown: Melittin peptide

<400> SEQUENCE: 20

Lys Lys Gly Ile Gly Ala Ile Leu Lys Val Leu Ala Thr Gly Leu Pro
1               5                   10                  15

Thr Leu Ile Ser Trp Ile Lys Asn Lys Arg Lys Gln
            20                  25

<210> SEQ ID NO 21
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 21

Gly Ile Gly Ala Ile Leu Glu Val Leu Ala Thr Gly Leu Pro Thr Leu
1               5                   10                  15

Ile Ser Trp Ile Lys Asn Lys Arg Lys Gln
            20                  25

<210> SEQ ID NO 22
<211> LENGTH: 22
<212> TYPE: PRT
<213> ORGANISM: Unknown
<220> FEATURE:
<223> OTHER INFORMATION: Description of Unknown: Melittin peptide

<400> SEQUENCE: 22

Gly Ile Gly Ala Val Leu Ser Val Leu Thr Thr Gly Leu Pro Ala Leu
1               5                   10                  15

Ile Ser Trp Ile Lys Arg
            20

<210> SEQ ID NO 23
<211> LENGTH: 24
<212> TYPE: PRT
<213> ORGANISM: Unknown
<220> FEATURE:
<223> OTHER INFORMATION: Description of Unknown: Melittin peptide

<400> SEQUENCE: 23

Gly Ile Gly Ala Val Leu Lys Val Leu Thr Thr Gly Leu Pro Ala Leu
1               5                   10                  15

Ile Ser Trp Ile Lys Arg Lys Arg
            20

<210> SEQ ID NO 24
<211> LENGTH: 22
<212> TYPE: PRT
<213> ORGANISM: Unknown
<220> FEATURE:
<223> OTHER INFORMATION: Description of Unknown: Melittin peptide

<400> SEQUENCE: 24

Gly Ile Gly Ala Val Leu Lys Val Leu Thr Thr Gly Leu Pro Ala Leu
1               5                   10                  15

Ile Ser Trp Ile Lys Arg
            20

<210> SEQ ID NO 25
<211> LENGTH: 26
<212> TYPE: PRT
```

```
<213> ORGANISM: Unknown
<220> FEATURE:
<223> OTHER INFORMATION: Description of Unknown: Melittin peptide

<400> SEQUENCE: 25

Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 26
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 26

Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 27
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 27

Gln Gln Arg Lys Arg Lys Ile Trp Ser Ile Leu Ala Pro Leu Gly Thr
1               5                   10                  15

Thr Leu Val Lys Leu Val Ala Gly Ile Gly
            20                  25

<210> SEQ ID NO 28
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 28

Gln Gln Arg Lys Arg Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 29
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 29

Gln Gln Arg Lys Arg Lys Ile Trp Ser Ile Leu Ala Ala Leu Gly Thr
1               5                   10                  15

Thr Leu Val Lys Leu Val Ala Gly Ile Cys
            20                  25

<210> SEQ ID NO 30
<211> LENGTH: 26
```

```
<212> TYPE: PRT
<213> ORGANISM: Unknown
<220> FEATURE:
<223> OTHER INFORMATION: Description of Unknown: Melittin peptide

<400> SEQUENCE: 30

Gln Gln Lys Lys Lys Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 31
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 31

Gln Gln Arg Lys Arg Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 32
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 32

Gln Lys Arg Lys Asn Lys Ile Trp Ser Ile Leu Thr Pro Leu Gly Thr
1               5                   10                  15

Ala Leu Val Lys Leu Ile Ala Gly Ile Gly
            20                  25
```

GALACTOSE CLUSTER-PHARMACOKINETIC MODULATOR TARGETING MOIETY FOR SIRNA

CROSS REFERENCE TO RELATED APPLICATIONS

This application is a divisional of U.S. patent application Ser. No. 13/327,271, filed Dec. 15, 2011, now issued as U.S. Pat. No. 9,249,179, which claims priority to U.S. Provisional Patent Application No. 61/424,195, filed Dec. 17, 2010, the entire contents of which are incorporated herein by reference.

BACKGROUND OF THE INVENTION

The delivery of polynucleotide and other substantially cell membrane impermeable compounds into a living cell is highly restricted by the complex membrane system of the cell. Drugs used in antisense, RNAi, and gene therapies are relatively large hydrophilic polymers and are frequently highly negatively charged. Both of these physical characteristics severely restrict their direct diffusion across the cell membrane. For this reason, the major barrier to polynucleotide delivery is the delivery of the polynucleotide across a cell membrane to the cell cytoplasm or nucleus.

One means that has been used to deliver small nucleic acid in vivo has been to attach the nucleic acid to either a small targeting molecule or a lipid or sterol. While some delivery and activity has been observed with these conjugates, the nucleic acid dose required with these methods has been prohibitively large.

Numerous transfection reagents have also been developed that achieve reasonably efficient delivery of polynucleotides to cells in vitro. However, in vivo delivery of polynucleotides using these same transfection reagents is complicated and rendered ineffective by in vivo toxicity, adverse serum interactions, and poor targeting. Transfection reagents that work well in vitro, cationic polymers and lipids, typically form large cationic electrostatic particles and destabilize cell membranes. The positive charge of in vitro transfection reagents facilitates association with nucleic acid via charge-charge (electrostatic) interactions thus forming the nucleic acid/transfection reagent complex. Positive charge is also beneficial for nonspecific binding of the vehicle to the cell and for membrane fusion, destabilization, or disruption. Destabilization of membranes facilitates delivery of the substantially cell membrane impermeable polynucleotide across a cell membrane. While these properties facilitate nucleic acid transfer in vitro, they cause toxicity and ineffective targeting in vivo. Cationic charge results in interaction with serum components, which causes destabilization of the polynucleotide-transfection reagent interaction, poor bioavailability, and poor targeting. Membrane activity of transfection reagents, which can be effective in vitro, often leads to toxicity in vivo.

For in vivo delivery, the vehicle (nucleic acid and associated delivery agent) should be small, less than 100 nm in diameter, and preferably less than 50 nm. Even smaller complexes, less that 20 nm or less than 10 nm would be more useful yet. Delivery vehicles larger than 100 nm have very little access to cells other than blood vessel cells in vivo. Complexes formed by electrostatic interactions tend to aggregate or fall apart when exposed to physiological salt concentrations or serum components. Further, cationic charge on in vivo delivery vehicles leads to adverse serum interactions and therefore poor bioavailability. Interestingly, high negative charge can also inhibit targeted in vivo delivery by interfering with interactions necessary for targeting, i.e. binding of targeting ligands to cellular receptors. Thus, near neutral vehicles are desired for in vivo distribution and targeting. Without careful regulation, membrane disruption or destabilization activities are toxic when used in vivo. Balancing vehicle toxicity with nucleic acid delivery is more easily attained in vitro than in vivo.

Rozema et al., in U.S. Patent Publication 20040162260 demonstrated a means to reversibly regulate membrane disruptive activity of a membrane active polyamine. The membrane active polyamine provided a means of disrupting cell membranes. pH-dependent reversible regulation provided a means to limit activity to the endosomes of target cells, thus limiting toxicity. Their method relied on modification of amines on a polyamine with 2-propionic-3-methylmaleic anhydride.

This modification converted the polycation to a polyanion via conversion of primary amines to pairs of carboxyl groups (β carboxyl and γ carboxyl) and reversibly inhibited membrane activity of the polyamine. Rozema et al. (Bioconjugate Chem. 2003, 14, 51-57) reported that the β carboxyl did not exhibit a full apparent negative charge and by itself was not able to inhibit membrane activity. The addition of the γ carboxyl group was reported to be necessary for effective membrane activity inhibition. To enable co-delivery of the nucleic acid with the delivery vehicle, the nucleic acid was covalently linked to the delivery polymer. They were able to show delivery of polynucleotides to cells in vitro using their biologically labile conjugate delivery system. However, because the vehicle was highly negatively charged, with both the nucleic acid and the modified polymer having high negative charge density, this system was not efficient for in vivo delivery. The negative charge likely inhibited cell-specific targeting and enhanced non-specific uptake by the reticuloendothelial system (RES).

Rozema et al., in U.S. Patent Publication 20080152661, improved on the method of U.S. Patent Publication 20040162260 by eliminating the high negative charge density of the modified membrane active polymer. By substituting neutral hydrophilic targeting (galactose) and steric stabilizing (PEG) groups for the γ carboxyl of 2-propionic-3-methylmaleic anhydride, Rozema et al. were able to retain overall water solubility and reversible inhibition of membrane activity while incorporating effective in vivo hepatocyte cell targeting. As before, the polynucleotide was covalently linked to the transfection polymer. Covalent attachment of the polynucleotide to the transfection polymer was maintained to ensure co-delivery of the polynucleotide with the transfection polymer to the target cell during in vivo administration by preventing dissociation of the polynucleotide from the transfection polymer. Co-delivery of the polynucleotide and transfection polymer was required because the transfection polymer provided for transport of the polynucleotide across a cell membrane, either from outside the cell or from inside an endocytic compartment, to the cell cytoplasm. U.S. Patent Publication 20080152661 demonstrated highly efficient delivery of polynucleotides, specifically RNAi oligonucleotides, to liver cells in vivo using this new improved physiologically responsive polyconjugate.

However, covalent attachment of the nucleic acid to the polyamine carried inherent limitations. Modification of the transfection polymers, to attach both the nucleic acid and the masking agents was complicated by charge interactions. Attachment of a negatively charged nucleic acid to a positively charged polymer is prone to aggregation thereby limiting the concentration of the mixture. Aggregation could be overcome by the presence of an excess of the polycation or polyanion. However, this solution limited the ratios at which the nucleic acid and the polymer may be formulated. Also, attachment of the negatively charged nucleic acid onto the unmodified cationic polymer caused condensation and aggregation of the complex and inhibited polymer modification. Modification of the polymer, forming a negative polymer, impaired attachment of the nucleic acid.

Rozema et al. further improved upon the technology described in U.S. Patent Publication 20080152661, in U.S. Provisional Application 61/307,490. In U.S. Provisional Application 61/307,490, Rozema et al. demonstrated that, by carefully selecting targeting molecules, and attaching appropriate targeting molecules independently to both an siRNA and a delivery polymer, the siRNA and the delivery polymer could be uncoupled yet retain effective targeting of both elements to cells in vivo and achieve efficient functional targeted delivery of the siRNA. The delivery polymers used in both U.S. Patent Publication 20080152661 and U.S. Provisional Application 61/307,490 were relatively large synthetic polymers, poly(vinyl ether)s and poly(acrylate)s. The larger polymers enabled modification with both targeting ligands for cell-specific binding and PEG for increased shielding. Larger polymers were necessary for effective delivery, possibly through increased membrane activity and improved protection of the nucleic acid within the cell endosome. Larger polycations interact more strongly with both membranes and with anionic RNAs.

We have now developed an improved siRNA delivery system using an improved RNA interference polynucleotide targeting moiety.

SUMMARY OF THE INVENTION

In a preferred embodiment, the invention features a composition for delivering an RNA interference polynucleotide to a target cell in vivo comprising: an RNA interference polynucleotide conjugated to a targeting ligand-pharmacokinetic modulator targeting compound (siRNA-conjugate). The targeting ligand-pharmacokinetic modulator targeting compound has improved in vivo circulation and targeting properties compared to the targeting ligand alone. Exemplary targeting ligands include asialoglycoprotein receptor ligands and folate. The pharmacokinetic modulator, when combined with the targeting ligand provides increased tissue targeting. The siRNA can then be injected alone or in combination with a delivery molecule.

In a preferred embodiment we describe a pharmacokinetic modulator comprising a hydrophobic group having 16 or more carbon atoms. When combined with a targeting ligand, the targeting ligand-pharmacokinetic modulator provides improved in vivo delivery of siRNA. Exemplary suitable hydrophobic groups may be selected from the group comprising: cholesterol, palmitoyl, hexadec-8-enoyl, oleyl, (9E, 12E)-octadeca-9,12-dienoyl, dioctanoyl, and C16-C20 acyl. Hydrophobic groups having fewer than 16 carbon atoms are less effective in enhancing polynucleotide targeting.

Pharmacokinetic modulators useful as polynucleotide targeting moieties may be selected from the group consisting of: cholesterol, alkyl group, alkenyl group, alkynyl group, aryl group, aralkyl group, aralkenyl group, and aralkynyl group, each of which may be linear, branched, or cyclic. Pharmacokinetic modulators are preferably hydrocarbons, containing only carbon and hydrogen atoms. However, substitutions or heteroatoms which maintain hydrophobicity, for example fluorine, may be permitted.

In a one embodiment, the invention features a composition for delivering an RNA interference polynucleotide to a liver cell in vivo comprising: an ASGPr-targeted reversibly masked membrane active polyamine (delivery polymer) and an RNA interference polynucleotide conjugated to a galactose cluster-pharmacokinetic modulator targeting moiety (siRNA-conjugate). The delivery polymer and the siRNA-conjugate are synthesized separately and may be supplied in separate containers or a single container. The RNA interference polynucleotide is not conjugated to the polymer.

In a one embodiment, the membrane active polyamine comprises: an amphipathic polymer formed by random polymerization of amine-containing monomers, lower hydrophobic monomers, and higher hydrophobic monomers. The amine-containing monomers contain pendant amine groups selected from the group consisting of: primary amine and secondary amine. The lower hydrophobic monomers contain pendent hydrophobic groups having 1-6 carbon atoms. The higher hydrophobic monomers contain pendent hydrophobic groups having 12-36 or more carbon atoms. The ratio of amine groups to hydrophobic groups is selected to form a water soluble polymer with membrane disruptive activity, preferably ≥1 amine monomer per hydrophobic monomer. In one embodiment the polymer will have 60-80% amine monomers. Hydrophobic groups may be selected from the group consisting of: alkyl group, alkenyl group, alkynyl group, aryl group, aralkyl group, aralkenyl group, and aralkynyl group, each of which may be linear, branched, or cyclic, sterol, steroid, and steroid derivative. Hydrophobic groups are preferably hydrocarbons, containing only carbon and hydrogen atoms. However, substitutions or heteroatoms which maintain hydrophobicity, and include, for example fluorine, may be permitted. Particularly suitable membrane active polyamines comprise poly(vinyl ether) random terpolymers or poly(acrylate) random terpolymers.

In a preferred embodiment, an ASGPr-targeted reversibly masked melittin peptide comprises a melittin peptide reversibly modified by reaction of primary amines on the peptide with ASGPr ligand-containing masking agents. An amine is reversibly modified if cleavage of the modifying group restores the amine. Reversible modification of the melittin peptide reversibly inhibits membrane activity of the melittin peptide. Modification of polymer amine with the masking agent also preferably neutralizes charge of the amine. A preferred ASGPr ligand-containing masking agent comprises a galactosamine or galactosamine derivative having a disubstituted maleic anhydride amine-reactive group. Reaction of the anhydride with an amine reversibly modifies the amine to form a maleamate or maleamic acid. In the masked state, the reversibly masked melittin peptide does not exhibit membrane disruptive activity. Reversible modification of more than 80%, or more than 90%, of the amines on the melittin peptide is required to inhibit membrane activity and provide cell targeting function, i.e. form a reversibly masked melittin peptide.

In a preferred embodiment, a reversibly masked membrane active polyamine comprises a membrane active polyamine of the invention reversibly modified by reaction of amines on the polymer with masking agents. An amine is reversibly modified if cleavage of the modifying group restores the amine. Reversible modification of the membrane active polyamine reversibly inhibits membrane activity of the membrane active polyamine. Preferably, a masking agent also provides targeting function and/or serum interaction avoidance function. Modification of polymer amine with the masking agent also preferably neutralizes the charge of the amine. A preferred masking agent comprises a galactosamine or galactosamine derivative or a polyethylene glycol having a disubstituted maleic anhydride amine-reactive group. Reaction of the anhydride with an amine reversibly modifies the amine to form a maleamate or maleamic acid. In the masked state, the reversibly masked membrane active polyamine does not exhibit membrane disruptive activity. Reversible modification of more than 50%, more than 55%, more than 60%, more than 65%, more than 70%, more than 75%, or more than 80%, of the amines on the polyamine with masking agents may be required to inhibit membrane activity and provide cell targeting function, i.e. form a reversibly masked membrane active polymer. Membrane activity inhibition and/or in vivo targeting of the described membrane active polyamines requires modification of >50% of the polymer amines.

The RNAi polynucleotide conjugate and a delivery polymer can be administered to a mammal in pharmaceutically acceptable carriers or diluents. In one embodiment, the delivery polymer and the RNAi polynucleotide conjugate may be combined in a solution prior to administration to the mammal. In another embodiment, the delivery polymer and the RNAi polynucleotide conjugate may be co-administered to the mammal in separate solutions. In yet another embodiment, the delivery polymer and the RNAi polynucleotide conjugate may be administered to the mammal sequentially. For sequential administration, the delivery polymer may be administered prior to administration of the RNAi polynucleotide conjugate. Alternatively, for sequential administration, the RNAi polynucleotide conjugate may be administered prior to administration of the delivery polymer.

Further objects, features, and advantages of the invention will be apparent from the following detailed description when taken in conjunction with the accompanying drawings.

DETAILED DESCRIPTION OF THE INVENTION

Figure 1:
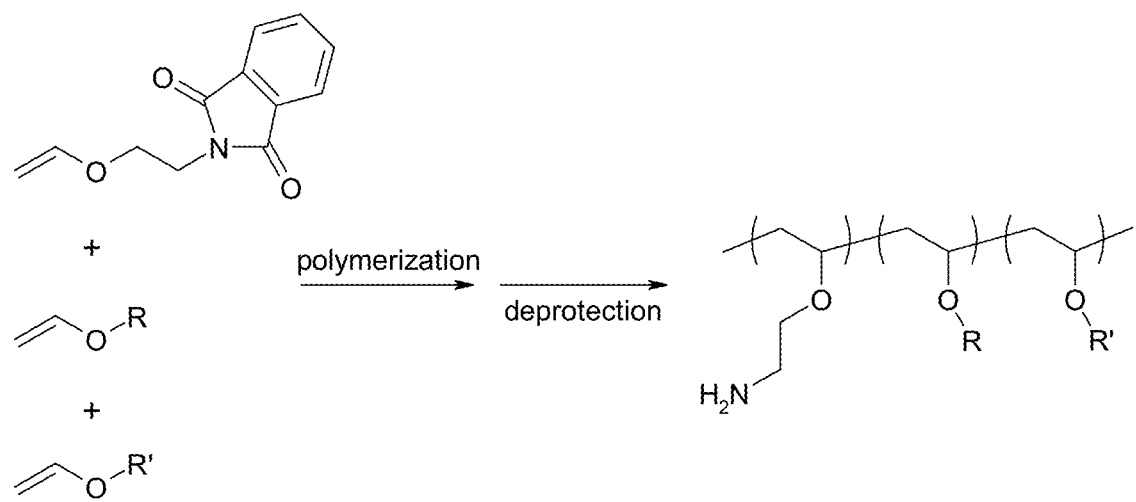
FIG. 1. Reaction scheme for polymerization of amphipathic poly(vinyl ether) random terpolymers.
Figure 2:
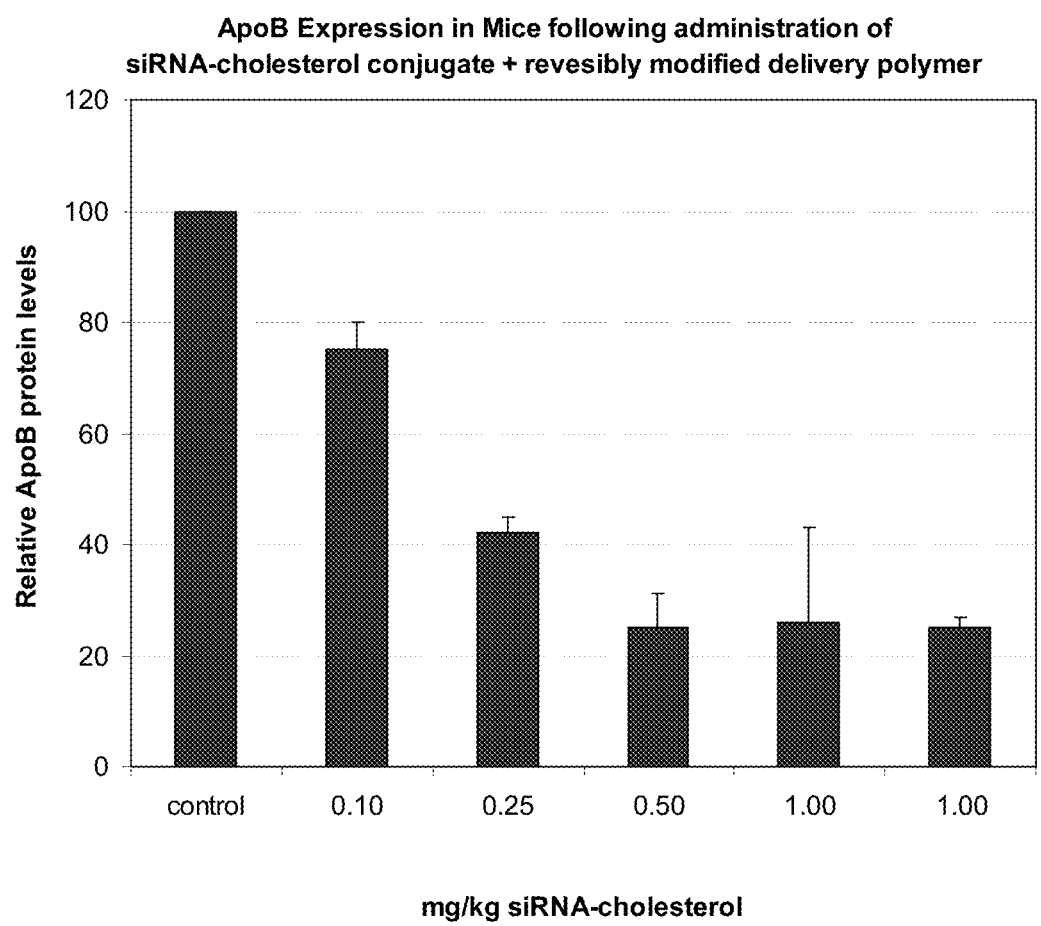
FIG. 2. Graph illustrating the effect of siRNA-cholesterol conjugate dose on gene knockdown.
Figure 3:
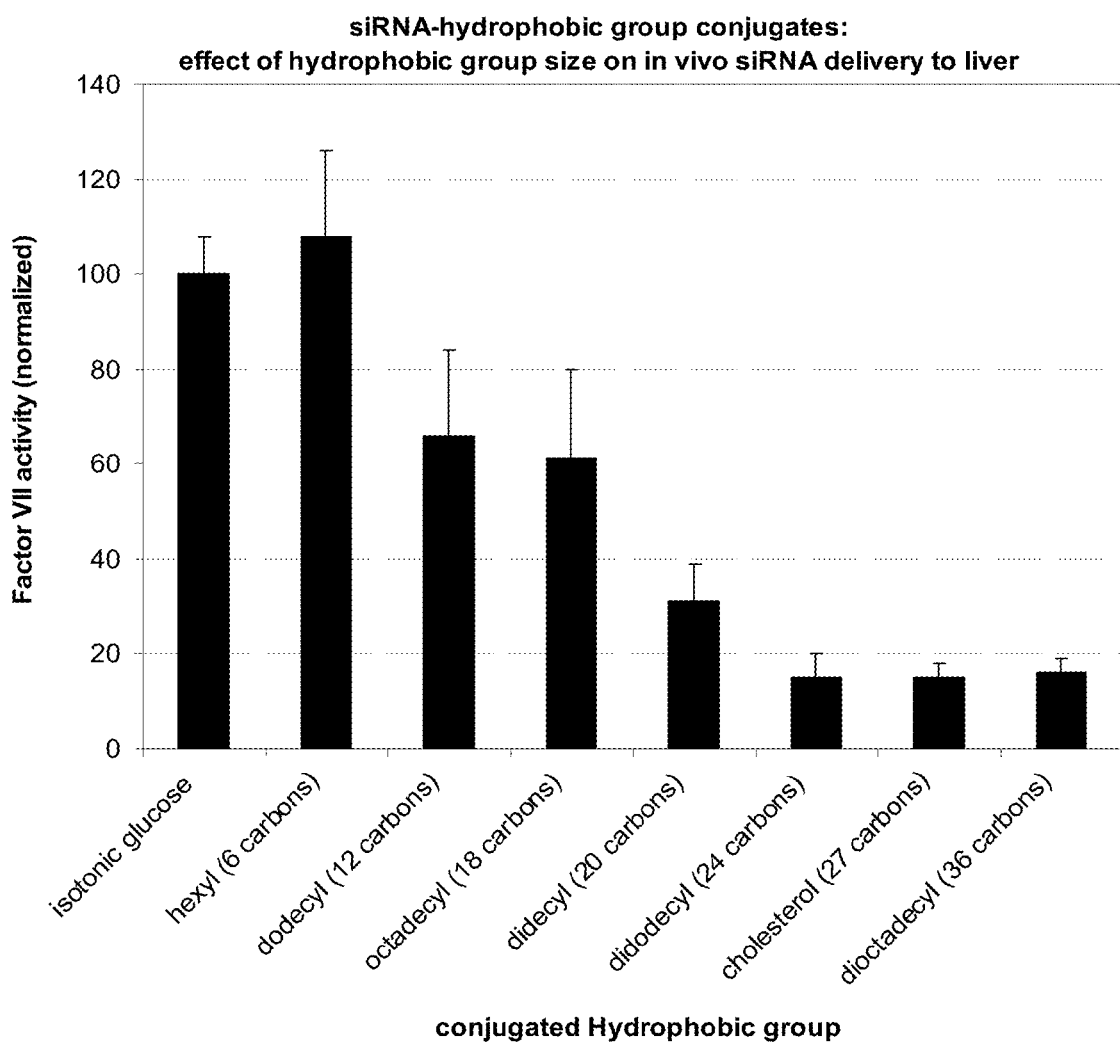
FIG. 3. Graph illustrating the effect of hydrophobe size on siRNA-hydrophobe conjugate targeting to liver.
Figure 4:
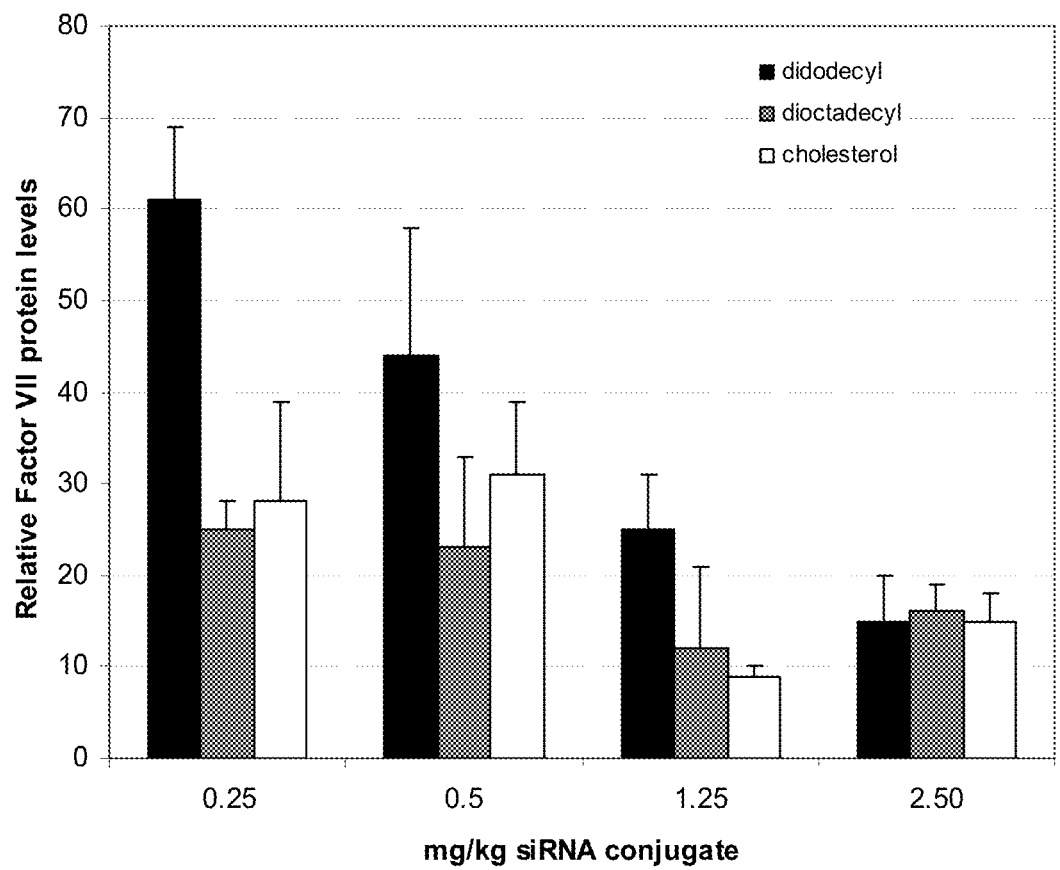
FIG. 4. Graph illustrating the effect of siRNA-hydrophobe conjugate dose on gene knockdown for several hydrophobic groups.
Figure 5:
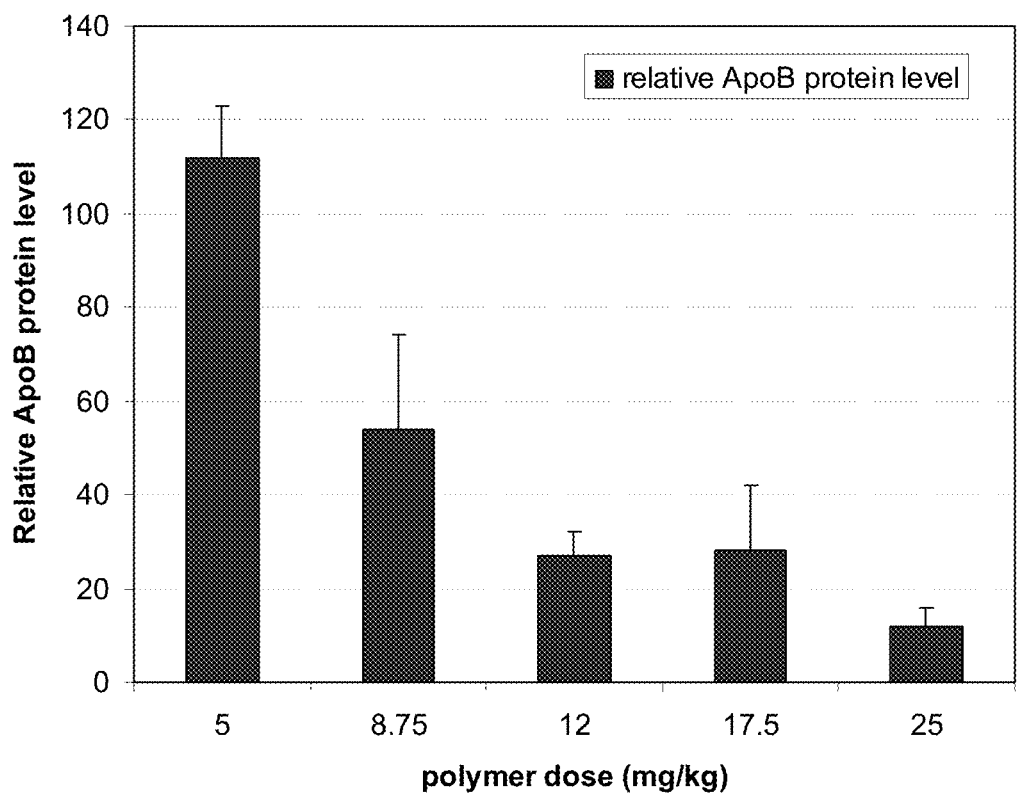
FIG. 5. Graph illustrating the effect of delivery polymer dose on siRNA-hydrophobe conjugate delivery to liver.
Figure 6:
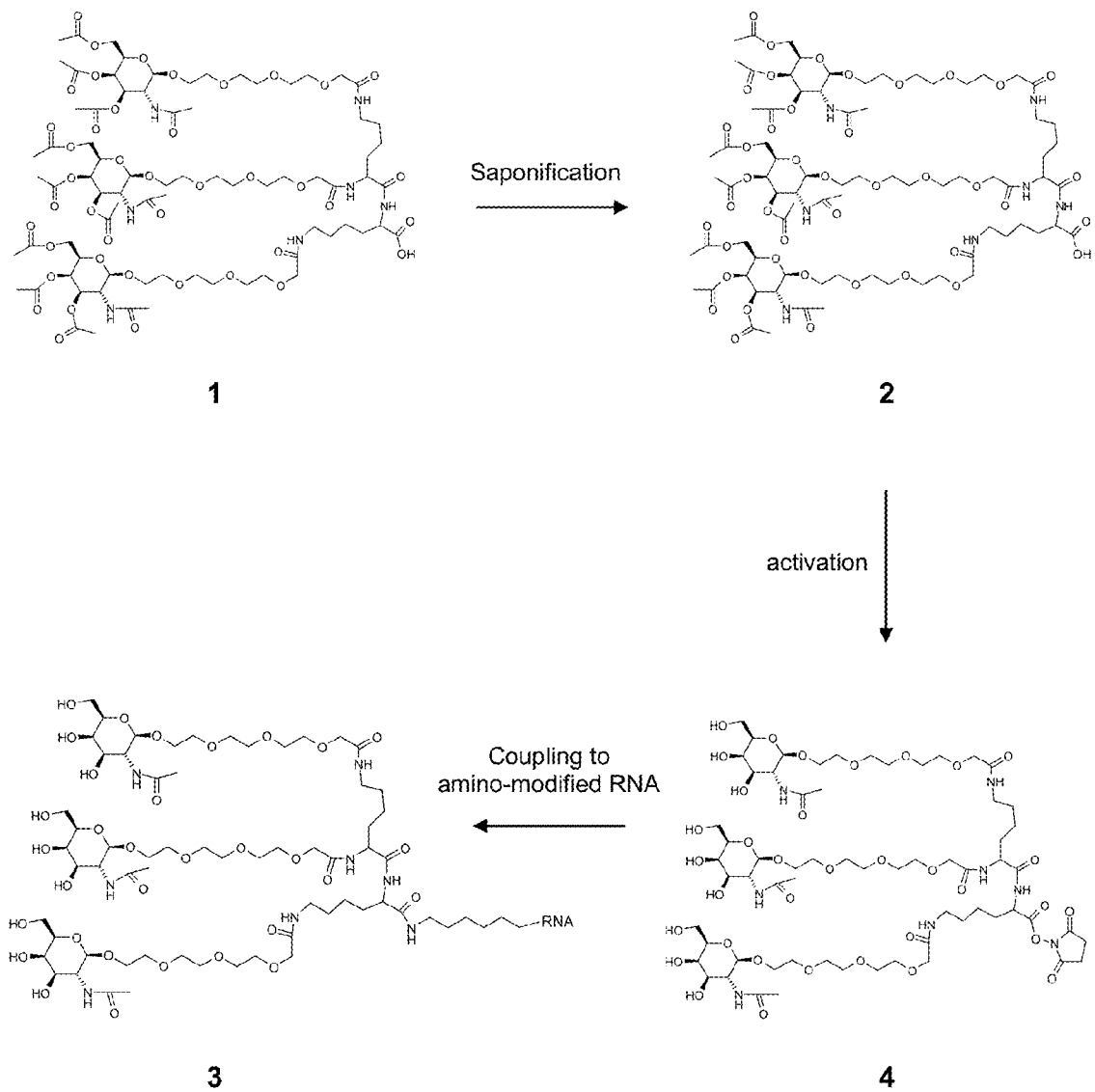
FIG. 6. Linkage of GalNAc Cluster to RNA.

Described herein is an improved RNA interference polynucleotide targeting moiety. The polynucleotide targeting moiety of the invention comprises a targeting ligand combined with a pharmacokinetic modulator. In a preferred embodiment, the targeting ligand and the pharmacokinetic modulator are covalently linked to each other and then covalently linked to the siRNA. In a preferred embodiment, linkage to the siRNA is by a physiologically labile covalent bond.

In a preferred embodiment we describe a pharmacokinetic modulator consisting of a hydrophobic group. More specifically, a pharmacokinetic modulator consists of a hydrophobic group having 16 or more carbon atoms. Exemplary suitable hydrophobic groups may be selected from the group comprising: cholesterol, palmitoyl, hexadec-8-enoyl, oleyl, (9E,12E)-octadeca-9,12-dienoyl, dioctanoyl, and C16-C20 acyl. Hydrophobic having fewer than 16 carbon atoms are less effective in enhancing polynucleotide targeting.

Pharmacokinetic modulators useful as polynucleotide targeting moieties may be selected from the group consisting of: cholesterol, alkyl group, alkenyl group, alkynyl group, aryl group, aralkyl group, aralkenyl group, and aralkynyl group, each of which may be linear, branched, or cyclic. Pharmacokinetic modulators are preferably hydrocarbons, containing only carbon and hydrogen atoms. However, substitutions or heteroatoms which maintain hydrophobicity, for example fluorine, may be permitted.

A targeting ligand and the pharmacokinetic modulator are linked to form the targeting ligand-pharmacokinetic modulator targeting moiety through a scaffold molecule. The targeting moiety scaffold can be any small molecule which permits linkage of the targeting ligand to the pharmacokinetic modulator and further permits attachment to the RNAi polynucleotide. An exemplary scaffold is a lysine or ornithine. A lysine or ornithine molecule contains two amine groups through which targeting ligand and the pharmacokinetic modulator may be attached and a carboxyl group through which attachment can be made to the RNAi polynucleotide. It is also possible, for example, to synthesis a pharmacokinetic modulator which can be covalently linked to the galactose cluster and the siRNA polynucleotide.

Described herein is an improved method for delivering RNA interference (RNAi) polynucleotides, to target cells in a mammal in vivo. Previously, in vivo delivery of polynucleotides required physical association of the polynucleotide with the delivery vehicle. The polynucleotide was either electrostatically associated with a delivery vehicle, as in polycation/nucleic acid complexes, encapsulated by the delivery vehicle, as in liposomes and stable nucleic acid-lipid particles (SNALPs), or covalently linked to a delivery vehicle, as in Dynamic PolyConjugates (Rozema et al. 2007). Surprisingly, we have found that by using appropriate RNAi polynucleotide conjugate molecules and appropriately targeted delivery polymers, the RNAi polynucleotide can be separated from the delivery polymer and still achieve efficient hepatocyte delivery of the polynucleotide.

Separation of the polynucleotide from the delivery peptide provides advantages in formulation, synthesis, and manufacturing.
  a) By removing the requirement that the polynucleotide and polymer are associated, either by covalent linkage or by charge-charge interaction, the concentration of the polymers and polynucleotides and the ratio between them is limited only by the solubility of the components rather than the solubility of the associated complex or ability to manufacture the complex. Increased solubility permits increased polynucleotide or delivery polymer concentration and therefore increased dosage.
  b) The polynucleotide and delivery polymer may be mixed at anytime prior to administration, or even administered separately. Thus, separation allows the components to be stored separately, either in solution or dry.
  c) Smaller, more stable formulation is possible compared to the larger, inherently unstable non-covalent delivery systems.
  d) Manufacture of the masked delivery polymer is easier in the absence of a covalently attached negatively charged polynucleotide or the need to covalently attach a negatively charged polynucleotide.

e) Manufacture is simplified and requires fewer steps in absence of physical association of the polynucleotide with the delivery polymer.

The invention includes conjugate delivery systems of the general structure:

$(M^1\text{-}L)_x\text{-}P\text{-}(L\text{-}M^2)_y$ plus N-T, wherein N is a RNAi polynucleotide, T is a targeting ligand-pharmacokinetic modulator polynucleotide targeting moiety, P is a membrane active polyamine, and masking agent $M^1$ contains a targeting moiety, (such as a galactose or galactose derivative having affinity for the asialoglycoprotein receptor for delivery to liver), covalently linked to P via a physiologically reversible linkage L, such as a maleamate linkage. Cleavage of L restores an unmodified amine on polyamine P. Masking agent $M^2$ is optional. If present, $M^2$ is a hydrophilic steric stabilizer covalently linked to P via a physiologically reversible linkage L, such as a maleamate linkage. x and y are each integers. In its unmodified state, P is a membrane active polyamine. Membrane active polyamines suitable for in vivo delivery of polynucleotides have been described in the art. Delivery polymer $(M^1\text{-}L)_x\text{-}P\text{-}(L\text{-}M^2)_y$ is not membrane active. Reversible modification of P amines, by attachment of $M^1$ and optionally $M^2$, reversibly inhibits or inactivates membrane activity of P and reduces the net positive charge of P. Sufficient masking agents are attached to P to inhibit membrane activity of the polymer. x+y has a value greater than 50%, more preferably greater than 60%, and more preferably greater than 70% of the amines on polyamine P, as determined by the quantity of amines on P in the absence of any masking agents. If P is a membrane active peptide, such as melittin, x+y has a value greater than 80%, and more preferably greater than 90% of the amines on polyamine P, as determined by the quantity of amines on P in the absence of any masking agents. Upon cleavage of reversible linkages L, unmodified amines are restored thereby reverting P to its unmodified, membrane active state. The reversible bond of reversible linkage L is chosen such that cleavage occurs in a desired physiological condition, such as that present in a desired tissue, organ, or sub-cellular location. A preferred reversible linkage is a pH labile linkage. $(M^1\text{-}L)_x\text{-}P\text{-}(L\text{-}M^2)_y$, an ASGPr-targeted reversibly masked membrane active polymer (masked polymer), and T-N, a polynucleotide-conjugate, are synthesized or manufactured separately. Neither T nor N are covalently linked directly or indirectly to P, L, $M^1$ or $M^2$. Electrostatic or hydrophobic association of the polynucleotide or the polynucleotide-conjugate with the masked or unmasked polymer is not required for in vivo liver delivery of the polynucleotide. The masked polymer and the polynucleotide conjugate can be supplied in the same container or in separate containers. They may be combined prior to administration, co-administered, or administered sequentially.

Polymer

The polymers of the invention are amphipathic membrane active polyamines. A polymer is a molecule built up by repetitive bonding together of smaller units called monomers. A polymer can be a homopolymer in which a single monomer is used or a polymer can be copolymer or heteropolymer in which two or more different monomers are used. The main chain of a polymer is composed of the atoms whose bonds are required for propagation of polymer length. A side chain of a polymer is composed of the atoms whose bonds are not required for propagation of polymer length.

More specifically, the polymers of the invention are amphipathic membrane active random copolymers. The monomers in random copolymers do not have a defined or arrangement along the main chain, and are written, for example, as: $\text{-}A_x\text{-}B_y\text{-}$ or $\text{-}A_x\text{-}B_y\text{-}C_z\text{-}$. The general compositions of such polymers are reflective of the ratio of input monomers. However, the exact ratio of one monomer to another may differ between chains. The distribution of monomers may also differ along the length of a single polymer. Also, the chemical properties of a monomer may affect its rate of incorporation into a random copolymer and its distribution within the polymer. While the ratio of monomers in a random polymer is dependent on the input ratio of monomer, the input ratio may not match exactly the ratio of incorporated monomers.

Amphipathic

Amphipathic, or amphiphilic, polymers are well known and recognized in the art and have both hydrophilic (polar, water-soluble) and hydrophobic (non-polar, lipophilic, water-insoluble) groups or parts.

Hydrophilic groups indicate in qualitative terms that the chemical moiety is water-preferring. Typically, such chemical groups are water soluble, and are hydrogen bond donors or acceptors with water. A hydrophilic group can be charged or uncharged. Charged groups can be positively charged (anionic) or negatively charged (cationic) or both (zwitterionic). Examples of hydrophilic groups include the following chemical moieties: carbohydrates, polyoxyethylene, certain peptides, oligonucleotides, amines, amides, alkoxy amides, carboxylic acids, sulfurs, and hydroxyls.

Hydrophobic groups indicate in qualitative terms that the chemical moiety is water-avoiding. Typically, such chemical groups are not water soluble, and tend not to form hydrogen bonds. Lipophilic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds.

As used herein, with respect to amphipathic polymers, a part is defined as a molecule derived when one covalent bond is broken and replaced by hydrogen. For example, in butyl amine, a breakage between the carbon and nitrogen bonds, and replacement with hydrogens, results in ammonia (hydrophilic) and butane (hydrophobic). If 1,4-diaminobutane is cleaved at nitrogen-carbon bonds, and replaced with hydrogens, the resulting molecules are again ammonia (2×) and butane. However, 1,4-diaminobutane is not considered amphipathic because formation of the hydrophobic part requires breakage of two bonds.

As used herein, a surface active polymer lowers the surface tension of water and/or the interfacial tension with other phases, and, accordingly, is positively adsorbed at the liquid/vapor interface. The property of surface activity is usually due to the fact that the molecules of the substance are amphipathic or amphiphilic.

Membrane Active

As used herein, membrane active polymers are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active polymers possess affinity for the membrane and cause a denaturation or deformation of bilayer structures. Membrane active polymers may be synthetic or non-natural amphipathic polymers.

As used herein, membrane active polymers are distinct from a class of polymers termed cell penetrating peptides or polymers represented by compounds such as the arginine-rich peptide derived from the HIV TAT protein, the antennapedia peptide, VP22 peptide, transportan, arginine-rich artificial peptides, small guanidinium-rich artificial polymers and the like. While cell penetrating compounds appear to transport some molecules across a membrane, from one side of a lipid bilayer to other side of the lipid bilayer, apparently without requiring endocytosis and without disturbing the integrity of the membrane, their mechanism is not understood.

Delivery of a polynucleotide to a cell is mediated by the membrane active polymer disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Endosomolytic

Endosomolytic polymers are polymers that, in response to a change in pH, are able to cause disruption or lysis of an endosome or provide for release of a normally cell membrane impermeable compound, such as a polynucleotide or protein, from a cellular internal membrane-enclosed vesicle, such as an endosome or lysosome. Endosomolytic polymers undergo a shift in their physico-chemical properties over a physiologically relevant pH range (usually pH 5.5-8). This shift can be a change in the polymer's solubility or ability to interact with other compounds or membranes as a result in a shift in charge, hydrophobicity, or hydrophilicity. Exemplary endosomolytic polymers have pH-labile groups or bonds. A reversibly masked membrane active polymer, wherein the masking agents are attached to the polymer via pH labile bonds, can therefore be considered to be an endosomolytic polymer.

Melittin is a small amphipathic membrane active peptide which naturally occurs in bee venom. Melittin can be isolated from a biological source or it can be synthetic. A synthetic polymer is formulated or manufactured by a chemical process "by man" and is not created by a naturally occurring biological process. As used herein, melittin encompasses the naturally occurring bee venom peptides of the melittin family that can be found in, for example, venom of the species: *Apis mellifera, Apis cerana, Vespula maculifrons, Vespa magnifica, Vespa velutina* nigrithorax, *Polistes* sp. HQL-2001, *Apis florae, Apis dorsata, Apis cerana cerana, Polistes hebraeus*. As used herein, melittin also encompasses synthetic peptides having amino acid sequence identical to or similar to naturally occurring melittin peptides. Specifically, melittin amino acid sequence encompass those shown in Table 1. Synthetic melittin peptides can contain naturally occurring L form amino acids or the enantiomeric D form amino acids (inverso). However, a melittin peptide should either contain essentially all L form or all D form amino acids. The melittin amino acid sequence can also be reversed (retro). Retro melittin can have L form amino acids or D form amino acids (retroinverso). Two melittin peptides can also be covalently linked to form a melittin dimer. Melittin can have modifying groups attached to either the amino terminal or carboxy terminal ends of the peptide. However, as used herein, melittin does not include chains or polymers containing more than two melittin peptides covalently linked to one another other or to another polymer or scaffold.

Hydrophobic groups are preferably hydrocarbons, containing only carbon and hydrogen atoms. However, non-polar substitutions or non-polar heteroatoms which maintain hydrophobicity, and include, for example fluorine, may be permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives. As used herein, lower hydrophobic monomers or groups comprise hydrophobic groups having two (2) to six (6) carbon atoms. As used herein, medium hydrophobic monomers or groups comprise hydrophobic groups having seven (7) to eleven (11) carbon atoms. As used herein, higher hydrophobic monomers or groups comprise hydrophobic groups having twelve (12) to thirty-sic (36) or more carbon atoms.

The ratio of amine groups to hydrophobic groups is selected to form a water soluble polymer with membrane disruptive activity. Preferred membrane active polymers of the invention are water soluble at ≥1 mg/ml, ≥5 mg/ml, ≥10 mg/ml, ≥15 mg/ml, ≥20 mg/ml, ≥25 mg/ml, and ≥30 mg/ml. Preferred membrane active polymers of the invention are surface active. Membrane active polymers of the invention are preferably in the size range of about 3 kDa to about 300 kDa. Because the polymers are amphipathic, they self-associate in aqueous solution, with a critical association concentration ≤1 mg/ml.

In one embodiment, the monomer incorporation ratio for the membrane active polyamine terpolymers is about 4-8 amine monomers: 3-5 lower hydrophobic monomers: 1 higher hydrophobic monomer. In another embodiment, the monomer incorporation ratio for the membrane active polyamines is about 5.4-7.5 amine monomers: 3-3.5 lower hydrophobic monomers: 1 higher hydrophobic monomers. In another embodiment, the monomer incorporation ratio for the membrane active polyamines is about 6 amine monomers to about 3 lower hydrophobic monomers to about 1 higher hydrophobic monomer. In one embodiment the hydrophobic groups of the hydrophobic monomers consist of alkyl groups.

In one embodiment, the amine/lower hydrophobic group copolymers are synthesized using monomers at a feed ratio of about 4-8 amine monomer: about 3-5 lower alkyl monomer. In another embodiment, the amine/lower hydrophobic group copolymers can be synthesized using monomers at a feed ratio of about 15 amine monomer: 4 lower hydrophobic group monomer.

In one embodiment, the amine/lower hydrophobic group/ higher hydrophobic group terpolymers are synthesized using monomers at a feed ratio of about 4-8 amine monomer: about 3-5 lower alkyl monomer: 1 higher alkyl monomer. In another embodiment, the amine/lower hydrophobic group/ higher hydrophobic group terpolymers can be synthesized using monomers at a feed ratio of about 15 amine monomer: 4 lower hydrophobic group monomer: 1 higher hydrophobic group monomer.

In one embodiment, particularly suitable membrane active polyamines comprise copolymers having amine containing monomers, butyl-containing monomers and higher hydrophobic group-containing monomers wherein the higher hydrophobic group contains 12-18 carbon atoms. Particularly suitable membrane active polyamines comprise poly(vinyl ether) random terpolymers or poly(acrylate) random terpolymers.

Masking

The delivery polymers of the invention comprise reversibly modified amphipathic membrane active polyamines wherein reversible modification inhibits membrane activity, neutralizes the polyamine to reduce positive charge and form a near neutral charge polymer, provides cell-type specific targeting, and inhibits non-specific interactions of the polymer. The polyamine is reversibly modified through reversible modification of amines on the polyamine.

The membrane active polyamines of the invention are capable of disrupting plasma membranes or lysosomal/ endocytic membranes. This membrane activity is an essential feature for cellular delivery of the polynucleotide. Membrane activity, however, leads to toxicity when the polymer is administered in vivo. Polyamines also interact readily with many anionic components in vivo, leading to undesired bio-distribution. Therefore, reversible masking of membrane activity of the polyamine is necessary for in vivo use. This masking is accomplished through reversible attachment of masking agents to the membrane active polyamine to form a reversibly masked membrane active polymer, i.e. a delivery polymer. In addition to inhibiting membrane activity, the masking agents shield the polymer from non-specific interactions, reduce serum interactions, increase circulation time, and provide cell-specific interactions, i.e. targeting.

It is an essential feature of the masking agents that, in aggregate, they inhibit membrane activity of the polymer, shield the polymer from non-specific interactions (reduce serum interactions, increase circulation time), and provide in vivo hepatocyte targeting. The membrane active polyamine is membrane active in the unmodified (unmasked) state and not membrane active (inactivated) in the modified (masked) state. A sufficient number of masking agents are linked to the polymer to achieve the desired level of inactivation. The desired level of modification of a polymer by attachment of masking agent(s) is readily determined using appropriate polymer activity assays. For example, if the polymer possesses membrane activity in a given assay, a sufficient level of masking agent is linked to the polymer to achieve the desired level of inhibition of membrane activity in that assay. Masking requires modification of ≥50%, ≥60%, ≥70%, or ≥80% of the amine groups on the polymer, as determined by the quantity of amines on the polymer in the absence of any masking agents. It is also a preferred characteristic of masking agents that their attachment to the polymer reduces positive charge of the polymer, thus forming a more neutral delivery polymer. It is desirable that the masked polymer retain aqueous solubility.

As used herein, a membrane active polyamine is masked if the modified polymer does not exhibit membrane activity and exhibits cell-specific (i.e. hepatocyte) targeting in vivo. A membrane active polyamine is reversibly masked if cleavage of bonds linking the masking agents to the polymer results in restoration of amines on the polymer thereby restoring membrane activity.

It is another essential feature that the masking agents are covalently bound to the membrane active polyamine through physiologically reversible bonds. By using physiologically reversible linkages or bonds, the masking agents can be cleaved from the polymer in vivo, thereby unmasking the polymer and restoring activity of the unmasked polymer. By choosing an appropriate reversible linkage, it is possible to form a conjugate that restores activity of the membrane active polymer after it has been delivered or targeted to a desired cell type or cellular location. Reversibility of the linkages provides for selective activation of the membrane active polymer. Reversible covalent linkages contain reversible or labile bonds which may be selected from the group comprising: physiologically labile bonds, cellular physiologically labile bonds, pH labile bonds, very pH labile bonds, and extremely pH labile bonds.

Preferred masking agents of the invention are able to modify the polymer (form a reversible bond with the polymer) in aqueous solution. A preferred amine-reactive group comprises a disubstituted maleic anhydride. A preferred masking agent is represented by the structure:

wherein in which $R^1$ is an alkyl group such as a methyl (—$CH_3$) group, ethyl (—$CH_2CH_3$) group, or propyl (—$CH_2CH_2CH_3$) group (to form a substituted alkylmaleic anhydride), and $R^2$ comprises an targeting ligand or a steric stabilizer.

In one embodiment, the targeting ligand comprises an ASGPr targeting moiety. In another embodiment, the steric stabilizer comprises a PEG.

The membrane active polyamine can be conjugated to masking agents in the presence of an excess of masking agents. The excess masking agent may be removed from the conjugated delivery polymer prior to administration of the delivery polymer.

Steric Stabilizer

As used herein, a steric stabilizer is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. A preferred steric stabilizer is a polyethylene glycol (PEG) or PEG derivative. As used herein, a preferred PEG can have about 1-500 ethylene glycol monomers, 2-20 ethylene glycol monomers, 5-15 ethylene glycol monomers, or about 10 ethylene glycol monomers. As used herein, a preferred PEG can also have a molecular weight average of about 85-20,000 Daltons (Da), about 200-1000 Da, about 200-750 Da, or about 550 Da. As used herein, steric stabilizers prevent or inhibit intramolecular or intermolecular interactions of a polymer to which it is attached relative to the polymer containing no steric stabilizer in aqueous solution.

Ligands

Targeting groups, or targeting ligands, are used for targeting or delivery a polymer or compound to target cells or tissues, or specific cells types. Targeting groups enhance the association of molecules with a target cell. Thus, targeting groups can enhance the pharmacokinetic or biodistribution properties of a conjugate to which they are attached to improve cellular distribution and cellular uptake of the conjugate. One or more targeting groups can be linked to the membrane active polymer either directly or via a linkage with a spacer. Binding of a targeting group, such as a ligand, to a cell or cell receptor may initiate endocytosis. Targeting groups may be monovalent, divalent, trivalent, tetravalent, or have higher valency. Targeting groups may be selected from the group comprising: compounds with affinity to cell surface molecule, cell receptor ligands, and antibodies, antibody fragments, and antibody mimics with affinity to cell surface molecules. A preferred targeting group comprises a cell receptor ligand. A variety of ligands have been used to target drugs and genes to cells and to specific cellular receptors. Cell receptor ligands may be selected from the group comprising: carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin). Examples of targeting groups include those that target the asialoglycoprotein receptor by using asialoglycoproteins or galactose residues. For example, liver hepatocytes contain ASGP Receptors. Therefore, galactose-containing targeting groups may be used to target hepatocytes. Galactose containing targeting groups include, but are not limited to: galactose, N-acetylgalactosamine, oligosaccharides, and saccharide clusters (such as: Tyr-Glu-Glu-(aminohexyl Gal-NAc)$_3$, lysine-based galactose clusters, and cholane-based galactose clusters). Further suitable conjugates can include oligosaccharides that can bind to carbohydrate recognition domains (CRD) found on the asialoglycoprotein-receptor (ASGP-R). Example conjugate moieties containing oligosaccharides and/or carbohydrate complexes are provided in U.S. Pat. No. 6,525,031

ASGPr Targeting Moiety

Targeting moieties or groups enhance the pharmacokinetic or biodistribution properties of a conjugate to which they are attached to improve cell-specific distribution and cell-specific uptake of the conjugate. Galactose and galactose derivates have been used to target molecules to hepatocytes in vivo through their binding to the asialoglycoprotein receptor (ASGPr) expressed on the surface of hepatocytes. As used herein, a ASGPr targeting moiety comprises a galactose and galactose derivative having affinity for the ASGPr equal to or greater than that of galactose. Binding of galactose targeting moieties to the ASGPr(s) facilitates cell-specific targeting of the delivery polymer to hepatocytes and endocytosis of the delivery polymer into hepatocytes.

ASGPr targeting moieties may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, and N-iso-butanoylgalactosamine (Iobst, S. T. and Drickamer, K. *J.B.C.* 1996, 271, 6686). ASGPr targeting moieties can be monomeric (e.g., having a single galactosamine) or multimeric (e.g., having multiple galactosamines).

In some embodiments, the galactose targeting moiety is linked to the amine-reactive group through a PEG linker as illustrated by the structure:

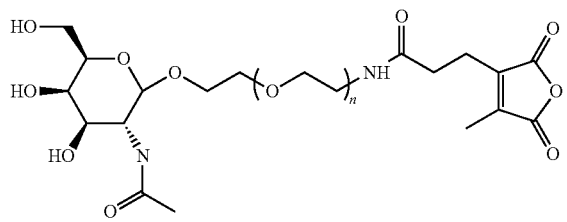

wherein n is an integer between 1 and 19.

In one embodiment, the membrane active polyamine is reversibly masked by attachment of ASGPr targeting moiety masking agents to ≥50%, ≥60%, ≥70%, or ≥80% of amines on the polyamine. In another embodiment, the membrane active polyamine is reversibly masked by attachment of ASGPr targeting moiety masking agents and PEG masking agents to ≥50%, ≥60%, ≥70%, or ≥80% of amines on the polyamine. In another embodiment, the ASGPr targeting moiety masking agents comprise an ASGPr targeting moiety linked to an amine-reactive group via a PEG linker. For membrane active polyamine masking with both ASGPr targeting moiety masking agents and PEG masking agents, a ratio of PEG to ASGPr targeting moiety is about 0-4:1, more preferably about 0.5-2:1. In another embodiment, there are about 1.3-2 PEG masking agents to about 1 galactose derivative masking agent.

Surface Charge

Zeta potential is a physical property which is exhibited by a particle in suspension and is closely related to surface charge. In aqueous media, the pH of the sample is one of the most important factors that affects zeta potential. When charge is based upon protonation/deprotonation of bases/acids, the charge is dependent on pH. Therefore, a zeta potential value must include the solution conditions, especially pH, to be meaningful. For typical particles, the magnitude of the zeta potential gives an indication of the potential stability of the colloidal system. If all the particles in suspension have a large negative or positive zeta potential, they will tend to repel each other and there will be no tendency for the particles to come together. However, if the particles have low zeta potential values, there will be no force to prevent the particles coming together and flocculating. The general dividing line between stable and unstable suspensions for typical particles is generally taken at either +30 or −30 mV. Particles with zeta potentials more positive than +30 mV or more negative than −30 mV are normally considered stable. Delivery polymers of the described invention exhibit a zeta potential of 20 mV to −20 mV at physiological salt and pH 8, but are colloidally stable in aqueous solution and do not flocculate.

Positive charge, or zeta potential, of a membrane active polyamine is reduced by modification with the masking agents. Polymer charge, especially positive charge, can result in unwanted interactions with serum components or non-target cells. Positive surface charge also plays a role in membrane activity by enhancing interaction of the polymer with negatively charged cell membranes. Therefore, delivery polymers with near neutral net charge or zeta potential are preferred for in vivo delivery of polynucleotides. Delivery polymers of the invention, membrane active polyamines masked by reversible attachment of ASGPr targeting moiety masking agents and steric stabilizer masking agents, have an apparent surface charge near neutral and are serum stable. More specifically, the delivery polymers of the invention have a zeta potential, measured at pH 8, between +30 and −30 mV, between +20 and −20 mV, between +10 and −10 mV, or between +5 and −5 mV. At pH 7, the net charge of the conjugate is expected to be more positive than at pH 8. Net charge, or surface charge, is a significant factor for in vivo applications.

Labile Linkage

A linkage or linker is a connection between two atoms that links one chemical group or segment of interest to another chemical group or segment of interest via one or more covalent bonds. For example, a linkage can connect a masking agent to a polymer. Formation of a linkage may connect two separate molecules into a single molecule or it may connect two atoms in the same molecule. The linkage may be charge neutral or may bear a positive or negative charge. A reversible or labile linkage contains a reversible or labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A reversible or labile bond is a covalent bond other than a covalent bond to a hydrogen atom that is capable of being selectively broken or cleaved under conditions that will not break or cleave other covalent bonds in the same molecule. More specifically, a reversible or labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, reversible or labile bonds encompass bonds that can be selectively cleaved more rapidly than other bonds a molecule.

Appropriate conditions are determined by the type of labile bond and are well known in organic chemistry. A labile bond can be sensitive to pH, oxidative or reductive conditions or agents, temperature, salt concentration, the presence of an enzyme (such as esterases, including nucleases, and proteases), or the presence of an added agent. For example, increased or decreased pH is the appropriate conditions for a pH-labile bond.

The rate at which a labile group will undergo transformation can be controlled by altering the chemical constituents of the molecule containing the labile group. For example, addition of particular chemical moieties (e.g., electron acceptors or donors) near the labile group can affect the particular conditions (e.g., pH) under which chemical transformation will occur.

As used herein, a physiologically labile bond is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. A cellular physiologically labile bond may also be cleaved in response to administration of a pharmaceutically acceptable exogenous agent. Physiologically labile bonds that are cleaved under appropriate conditions with a half life of less than 45 min. are considered very labile. Physiologically labile bonds that are cleaved under appropriate conditions with a half life of less than 15 min are considered extremely labile.

Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond.

As used herein, a pH-labile bond is a labile bond that is selectively broken under acidic conditions (pH<7). Such bonds may also be termed endosomally labile bonds, since cell endosomes and lysosomes have a pH less than 7. The term pH-labile includes bonds that are pH-labile, very pH-labile, and extremely pH-labile.

Reaction of an anhydride with an amine forms an amide and an acid. For many anhydrides, the reverse reaction (formation of an anhydride and amine) is very slow and energetically unfavorable. However, if the anhydride is a cyclic anhydride, reaction with an amine yields an amide acid, a molecule in which the amide and the acid are in the same molecule. The presence of both reactive groups (the amide and the carboxylic acid) in the same molecule accelerates the reverse reaction. In particular, the product of primary amines with maleic anhydride and maleic anhydride derivatives, maleamic acids, revert back to amine and anhydride $1\times10^9$ to $1\times10^{13}$ times faster than its noncyclic analogues (Kirby 1980).

Reaction of an Amine with an Anhydride to Form
an Amide and an Acid

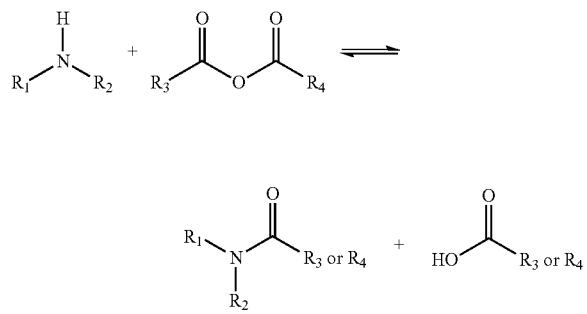

Reaction of an Amine with a Cyclic Anhydride to
Form an Amide Acid

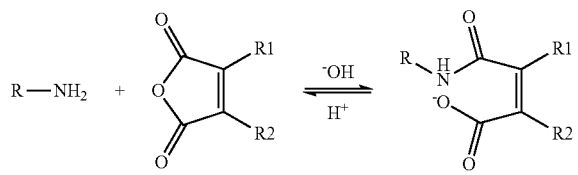

Cleavage of the amide acid to form an amine and an anhydride is pH-dependent and is greatly accelerated at acidic pH. This pH-dependent reactivity can be exploited to form reversible pH-labile bonds and linkers. Cis-aconitic acid has been used as such a pH-sensitive linker molecule. The γ-carboxylate is first coupled to a molecule. In a second step, either the α or β carboxylate is coupled to a second molecule to form a pH-sensitive coupling of the two molecules. The half life for cleavage of this linker at pH 5 is between 8 and 24 h.

Structures of Cis-Aconitic Anhydride and Maleic
Anhydride

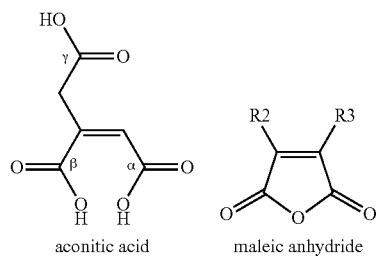

The pH at which cleavage occurs is controlled by the addition of chemical constituents to the labile moiety. The rate of conversion of maleamic acids to amines and maleic anhydrides is strongly dependent on substitution (R2 and R3) of the maleic anhydride system. When R2 is methyl, the rate of conversion is 50-fold higher than when R2 and R3 are hydrogen. When there are alkyl substitutions at both R2 and R3 (e.g., 2,3-dimethylmaleicanhydride) the rate increase is dramatic: 10,000-fold faster than non-substituted maleic anhydride. The maleamate bond formed from the modification of an amine with 2,3-dimethylmaleic anhydride is cleaved to restore the anhydride and amine with a half-life between 4 and 10 min at pH 5. It is anticipated that if R2 and R3 are groups larger than hydrogen, the rate of amide-acid conversion to amine and anhydride will be faster than if R2 and/or R3 are hydrogen.

Very pH-labile bond: A very pH-labile bond has a half-life for cleavage at pH 5 of less than 45 min. The construction of very pH-labile bonds is well-known in the chemical art.

Extremely pH-labile bonds: An extremely pH-labile bond has a half-life for cleavage at pH 5 of less than 15 min. The construction of extremely pH-labile bonds is well-known in the chemical art.

Disubstituted cyclic anhydrides are particularly useful for attachment of masking agents to membrane active polyamines of the invention. They provide physiologically pH-labile linkages, readily modify amines, and restore those amines upon cleavage in the reduced pH found in cellular endosomes and lysosome. Second, the α or β carboxylic acid group created upon reaction with an amine, appears to contribute only about $1/20^{th}$ of the expected negative charge to the polymer (Rozema et al. Bioconjugate Chemistry 2003). Thus, modification of the polyamine with the disubstituted maleic anhydrides effectively neutralizes the positive charge of the polyamine rather than creates a polymer with high negative charge. Near neutral polymers are preferred for in vivo delivery.

A naturally occurring polymer is a polymer that can be found in nature. Examples include polynucleotides, proteins, collagen, and polysaccharides (starches, cellulose, glycosaminoglycans, chitin, agar, agarose). A natural polymer can be isolated from a biological source or it can be synthetic. A synthetic polymer is formulated or manufactured by a chemical process "by man" and is not created by a naturally occurring biological process. A non-natural polymer is a synthetic polymer that is not made from naturally occurring (animal or plant) materials or monomers (such as amino acids, nucleotides, and saccharides). A polymer may be fully or partially natural, synthetic, or non-natural.

RNAi Polynucleotide Conjugate

We have found that conjugation of an RNAi polynucleotide to a targeting ligand-pharmacokinetic modulator targeting moiety, and co-administration of the RNAi polynucleotide conjugate with the delivery polymer described above provides for improved delivery of the RNAi polynucleotide in vivo. By functional delivery, it is meant that the RNAi polynucleotide is delivered to the cell and has the expected biological activity, sequence-specific inhibition of gene expression. Many molecules, including polynucleotides, administered to the vasculature of a mammal are normally cleared from the body by the liver. Clearance of a polynucleotide by the liver wherein the polynucleotide is degraded or otherwise processed for removal from the body and wherein the polynucleotide does not cause sequence-specific inhibition of gene expression is not considered functional delivery.

The RNAi polynucleotide conjugate is formed by covalently linking the RNAi polynucleotide to the targeting ligand-pharmacokinetic modulator targeting moiety. The polynucleotide may be synthesized or modified such that it contains a reactive group A. The targeting moiety may be synthesized or modified such that it contains a reactive group B. Reactive groups A and B are chosen such that they can be linked via a covalent linkage using methods known in the art.

The targeting moiety may be linked to the 3' or the 5' end of the RNAi polynucleotide. For siRNA polynucleotides, the targeting moiety may be linked to either the sense strand or the antisense strand, though the sense strand is preferred. In some embodiments, the siRNA is attached to the targeting moiety via a short alkyl chain containing a reactive group A, such as a primary amine group. Reactive group A is then coupled to a reactive group B, such as a carboxyl group, on the targeting moiety.

For targeting hepatocytes in liver, a preferred targeting ligand is a galactose cluster. A galactose cluster comprises a molecule having two to four terminal galactose derivatives. As used herein, the term galactose derivative includes both galactose and derivatives of galactose having affinity for the asialoglycoprotein receptor equal to or greater than that of galactose. A terminal galactose derivative is attached to a molecule through its C-1 carbon. The asialoglycoprotein receptor (ASGPr) is unique to hepatocytes and binds branched galactose-terminal glycoproteins. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, J. Biol. Chem., 257, 939-945). Multivalency is required to achieve nM affinity. The attachment of a single galactose derivative having affinity for the asialoglycoprotein receptor does not enable functional delivery of the RNAi polynucleotide to hepatocytes in vivo when co-administered with the delivery polymer.

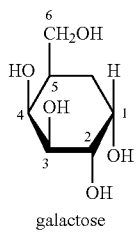

galactose

A galactose cluster contains three galactose derivatives each linked to a central branch point. The galactose derivatives are attached to the central branch point through the C-1 carbons of the saccharides. The galactose derivative is preferably linked to the branch point via linkers or spacers. A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a $PEG_3$ spacer. The branch point can be any small molecule which permits attachment of the three galactose derivatives and further permits attachment of the branch point to the RNAi polynucleotide. An exemplary branch point group is a di-lysine. A di-lysine molecule contains three amine groups through which three galactose derivatives may be attached and a carboxyl reactive group through which the di-lysine may be attached to the RNAi polynucleotide. Attachment of the branch point to the RNAi polynucleotide may occur through a linker or spacer. A preferred spacer is a flexible hydrophilic spacer. A preferred flexible hydrophilic spacer is a PEG spacer. A preferred PEG spacer is a $PEG_3$ spacer (three ethylene units). The galactose cluster may be attached to the 3' or 5' end of the RNAi polynucleotide using methods known in the art. For RNAi polynucleotides having 2 strands, such as siRNA, the galactose cluster may be attached to either strand.

A preferred galactose derivative is an N-acetyl-galactosamine (GalNAc). Other saccharides having affinity for the asialoglycoprotein receptor may be selected from the list comprising: galactose, galactosamine, N-formylgalactosamine, N-acetylgalactosamine, N-propionyl-galactosamine, N-n-butanoylgalactosamine, and N-iso-butanoylgalactosamine. The affinities of numerous galactose derivatives for the asialoglycoprotein receptor have been studied (see for example: Iobst, S. T. and Drickamer, K. J.B.C. 1996, 271, 6686) or are readily determined using methods typical in the art.

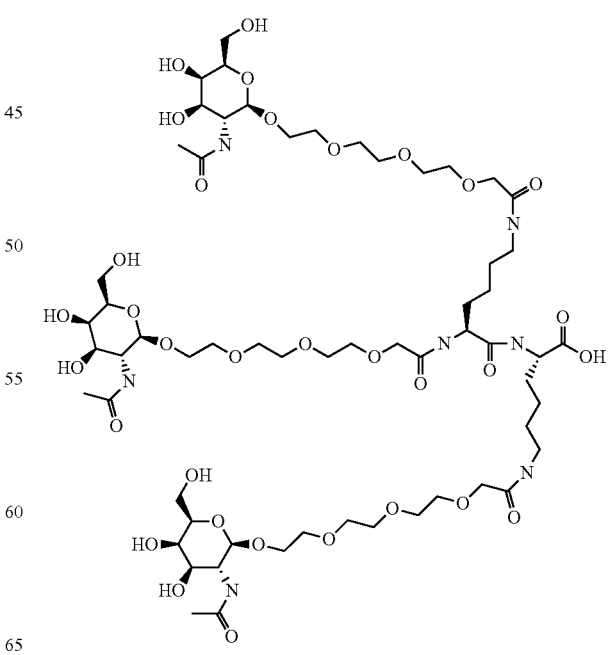

One Embodiment of a Galactose Cluster

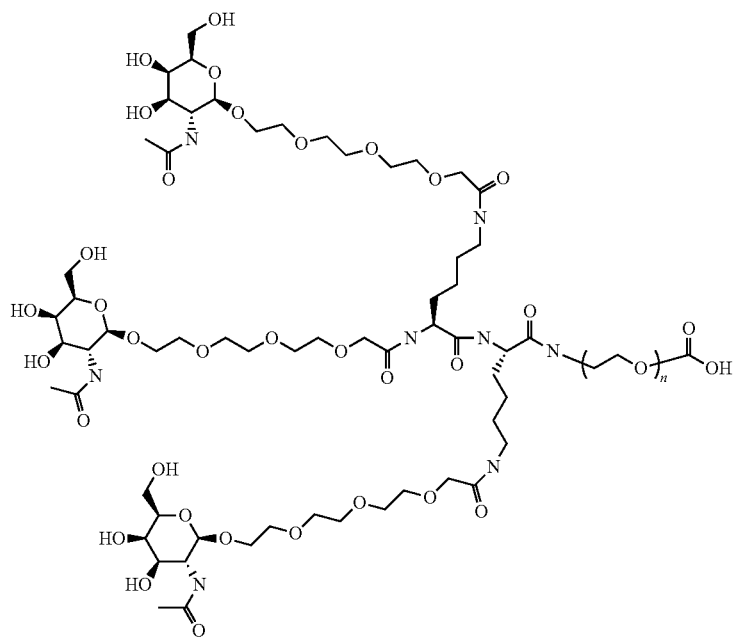

Galactose Cluster with PEG Spacer Between
Branch Point and Nucleic Acid

Polynucleotide

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap moiety at the 5'-end, the 3'-end, or both the 5' and 3' ends. The cap moiety can be, but is not limited to, an inverted deoxy abasic moiety, an inverted deoxy thymidine moiety, a thymidine moiety, or 3' glyceryl modification.

An RNA interference (RNAi) polynucleotide is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, microRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The polynucleotides of the invention can be chemically modified. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time increasing the serum stability of these compounds. Chemically modified siRNA can also minimize the possibility of activating interferon activity in humans.

In one embodiment, a chemically-modified RNAi polynucleotide of the invention comprises a duplex having two strands, one or both of which can be chemically-modified, wherein each strand is about 19 to about 29 nucleotides. In one embodiment, an RNAi polynucleotide of the invention comprises one or more modified nucleotides while maintaining the ability to mediate RNAi inside a cell or reconstituted in vitro system. An RNAi polynucleotide can be modified wherein the chemical modification comprises one or more (e.g., about 1, 2, 3, 4, 5, 6, 7, 8, 9, 10, or more) of the nucleotides. An RNAi polynucleotide of the invention can comprise modified nucleotides as a percentage of the total number of nucleotides present in the RNAi polynucleotide. As such, an RNAi polynucleotide of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given RNAi polynucleotide depends on the total number of nucleotides present in the RNAi polynucleotide. If the RNAi polynucleotide is single stranded, the percent modification can be based upon the total number of nucleotides present in the single stranded RNAi polynucleotide. Likewise, if the RNAi polynucleotide is double stranded, the percent modification can be based upon the total number of nucleotides present in the sense strand, antisense strand, or both the sense and antisense strands. In addition, the actual percentage of modified nucleotides present in a given RNAi polynucleotide can also depend on the total number of purine and pyrimidine nucleotides present in the RNAi polynucleotide. For example, wherein all pyrimidine nucleotides and/or all purine nucleotides present in the RNAi polynucleotide are modified.

An RNAi polynucleotide modulates expression of RNA encoded by a gene. Because multiple genes can share some degree of sequence homology with each other, an RNAi polynucleotide can be designed to target a class of genes with sufficient sequence homology. Thus, an RNAi polynucleotide can contain a sequence that has complementarity to sequences that are shared amongst different gene targets or are unique for a specific gene target. Therefore, the RNAi polynucleotide can be designed to target conserved regions of an RNA sequence having homology between several genes thereby targeting several genes in a gene family (e.g., different gene isoforms, splice variants, mutant genes, etc.). In another embodiment, the RNAi polynucleotide can be designed to target a sequence that is unique to a specific RNA sequence of a single gene.

The term complementarity refers to the ability of a polynucleotide to form hydrogen bond(s) with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein or protein subunit translated from the RNA, is reduced below that observed in the absence of the blocking polynucleotide-conjugates of the invention. Inhibition, down-regulation, or knockdown of gene expression, with a polynucleotide delivered by the compositions of the invention, is preferably below that level observed in the presence of a control inactive nucleic acid, a nucleic acid with scrambled sequence or with inactivating mismatches, or in absence of conjugation of the polynucleotide to the masked polymer.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans.

The RNAi polynucleotide-targeting moiety conjugate can be co-administered with the delivery polymer. By co-administered it is meant that the RNAi polynucleotide and the delivery polymer are administered to the mammal such that both are present in the mammal at the same time. The RNAi polynucleotide-targeting moiety conjugate and the delivery polymer may be administered simultaneously or they may be delivered sequentially. For simultaneous administration, they may be mixed prior to administration. For sequential administration, either the RNAi polynucleotide-targeting moiety conjugate or the delivery polymer may be administered first.

Therapeutic Effect

RNAi polynucleotides may be delivered for research purposes or to produce a change in a cell that is therapeutic. In vivo delivery of RNAi polynucleotides is useful for research reagents and for a variety of therapeutic, diagnostic, target validation, genomic discovery, genetic engineering, and pharmacogenomic applications. We have disclosed RNAi polynucleotide delivery resulting in inhibition of endogenous gene expression in hepatocytes. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. For example, Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly, inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes serve as useful paradigms for expression of intracellular proteins in general.

The liver is one of the most important target tissues for gene therapy given its central role in metabolism (e.g., lipoprotein metabolism in various hypercholesterolemias) and the secretion of circulating proteins (e.g., clotting factors in hemophilia). In addition, acquired disorders such as chronic hepatitis and cirrhosis are common and are also potentially treated by polynucleotide-based liver therapies. A number of diseases or conditions which affect or are affected by the liver are potentially treated through knockdown (inhibition) of gene expression in the liver. Such liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury.

The amount (dose) of delivery polymer and RNAi-polynucleotide-conjugate that is to be administered can be determined empirically. We have shown effective knockdown of gene expression using 0.1-10 mg/kg animal weight of siRNA-conjugate and 5-60 mg/kg animal weight delivery polymer. A preferred amount in mice is 0.25-2.5 mg/kg siRNA-conjugate and 10-40 mg/kg delivery polymer. More preferably, about 12.5-20 mg/kg delivery polymer is administered. The amount of RNAi polynucleotide-conjugate is easily increased because it is typically not toxic in larger doses.

As used herein, in vivo means that which takes place inside an organism and more specifically to a process performed in or on the living tissue of a whole, living multicellular organism (animal), such as a mammal, as opposed to a partial or dead one.

EXAMPLES

Example 1. Poly(Vinyl Ether) Random Copolymers

A. Vinyl Ether Monomers for Incorporation of Amine-Containing Monomers

2-Vinyloxy Ethyl Phthalimide was prepared via reacting 2-chloroethyl vinyl ether (25 g, 0.24 mol; CAS #110-75-8) and potassium phthalimide (25 g, 0.135 mol; CAS #1074-82-4) in 100° C. N,N-Dimethylformamide (DMF, 75 ml) using tetra n-butyl ammonium bromide (0.5 g; CAS #1643-

19-2) as the phase transfer catalyst. This solution was heated for 6 h and then crashed out in water and filtered. This solid was then recrystallized twice from methanol to give white crystals.

B. Synthesis of Water-Soluble, Amphipathic, Membrane Active Poly(Vinyl Ether) Polyamine Terpolymers X mol % amine-protected vinylether (e.g., 2-Vinyloxy Ethyl Phthalimide) is added to an oven dried round bottom flask under a blanket of nitrogen in anhydrous dichloromethane. To this solution Y mol % lower hydrophobic group (e.g., propyl, butyl) vinylether and optionally Z mol % higher hydrophobic group (e.g., dodecyl, octadecyl) vinylether are added (FIG. 1). The solution is placed in a −50 to −78° C. bath, and the 2-vinyloxy ethyl phthalimide is allowed to precipitate. To this solution 10 mol % $BF_3 \cdot (OCH_2CH_3)_2$ is added and the reaction is allowed to proceed for 2-3 h at −50° to −78° C. Polymerization is terminated by addition of ammonium hydroxide in methanol solution. The polymer is brought to dryness under reduced pressure and then brought up in 1,4-dioxane/methanol (2/1). 20 mol eq. of hydrazine per phthalimide is added to remove the protecting group from the amine. The solution is refluxed for 3 h and then brought to dryness under reduced pressure. The resulting solid is dissolved in 0.5 mol/L HCl and refluxed for 15 min to form the hydrochloride salt of the polymer, diluted with distilled water, and refluxed for an additional hour. The solution is then neutralized with NaOH, cooled to room temperature (RT), transferred to molecular cellulose tubing, dialyzed against distilled water, and lyophilized. The polymer can be further purified using size exclusion or other chromatography. The molecular weight of the polymers is estimated using columns according to standard procedures, including analytical size-exclusion chromatography and size-exclusion chromatography with multi-angle light scattering (SEC-MALS).

C. Synthesis of DW1360

An amine/butyl/octadecyl poly(vinyl ether) terpolymer, was synthesized from 2-vinyloxy ethyl phthalimide (5 g, 23.02 mmol), butyl vinylether (0.665 g, 6.58 mmol), and octadecyl vinylether (0.488 g, 1.64 mmol) monomers. 2-vinyloxy ethyl phthalimide was added to a 200 mL oven dried round bottom flask containing a magnetic stir bar under a blanket of Argon in 36 mL anhydrous dichloromethane. To this solution was added butyl vinyl ether and n-octadecyl vinyl ether. The monomers were fully dissolved at room temperature (RT) to obtain a clear, homogenous solution. The reaction vessel containing the clear solution was then placed into a −50° C. bath generated by addition of dry ice to a 1:1 solution of ACS grade denatured alcohol and ethylene glycol and a visible precipitation of phthalimide monomer was allowed to form. After cooling for about 1.5 min, $BF_3 \cdot (OCH_2CH_3)_2$ (0.058 g, 0.411 mmol) was added to initiate the polymerization reaction. The phthalimide monomer dissolved upon initiation of polymerization. The reaction was allowed to proceed for 3 h at −50° C. The polymerization was stopped by the addition of 5 mL of 1% ammonium hydroxide in methanol. The solvents were then removed by rotary evaporation.

The polymer was then dissolved in 30 mL of 1,4-dioxane/methanol (2/1). To this solution was added hydrazine (0.147 g, 46 mmol) and the mixture was heated to reflux for 3 h. The solvents were then removed by rotary evaporation and the resulting solid was then brought up in 20 mL of 0.5 mol/L HCl and refluxed for 15 minutes, diluted with 20 mL distilled water, and refluxed for an additional hour. This solution was then neutralized with NaOH, cooled to RT, transferred to 3,500 molecular weight cellulose tubing, dialyzed for 24 h (2×20 L) against distilled water, and lyophilized.

While polymers containing the indicated vinyl ether monomers are described, the invention is not limited to these particular monomers.

D. Synthesis of Water-Soluble, Amphipathic, Membrane Active Poly(Acrylate) Polyamine Terpolymers Poly(acrylate) and poly(methylacrylate) heteropolymers may be synthesized using the general free radical reaction scheme (as used herein a poly(methacrylate) polyamine is a subgenus of the genus poly(acrylate) polyamine):

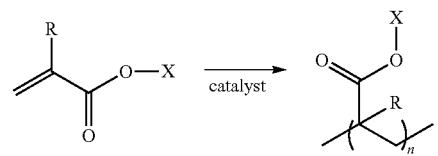

wherein R is independently a hydrogen or methyl group and X represents the desired monomer pendent groups present in the polymer at the desired ratios.

For polymer syntheses, suitable monomers include, but are not limited to:

BOC-protected amine-containing monomers (M):

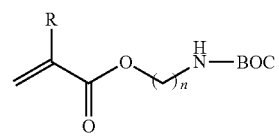

wherein n=1-4 and removal of the BOC protecting group yields a primary amine.

Lower hydrophobic group monomers (N):

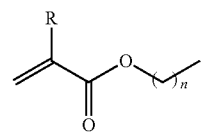

wherein n=1-5 and one or more carbons may be unsaturated.

Higher hydrophobic group monomers (O):

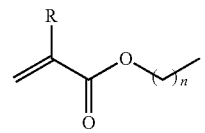

wherein n=8-24 and one or more carbons may be unsaturated.

Using the above monomers, membrane active heteropolymers can be synthesized with the following compositions: M can be 50-90 mol %; N can be 10-50 mol %; O can be 0-10 mol %.

E. Synthesis of Water-Soluble, Amphipathic, Membrane Active Poly(Acrylate) Polyamine Terpolymers

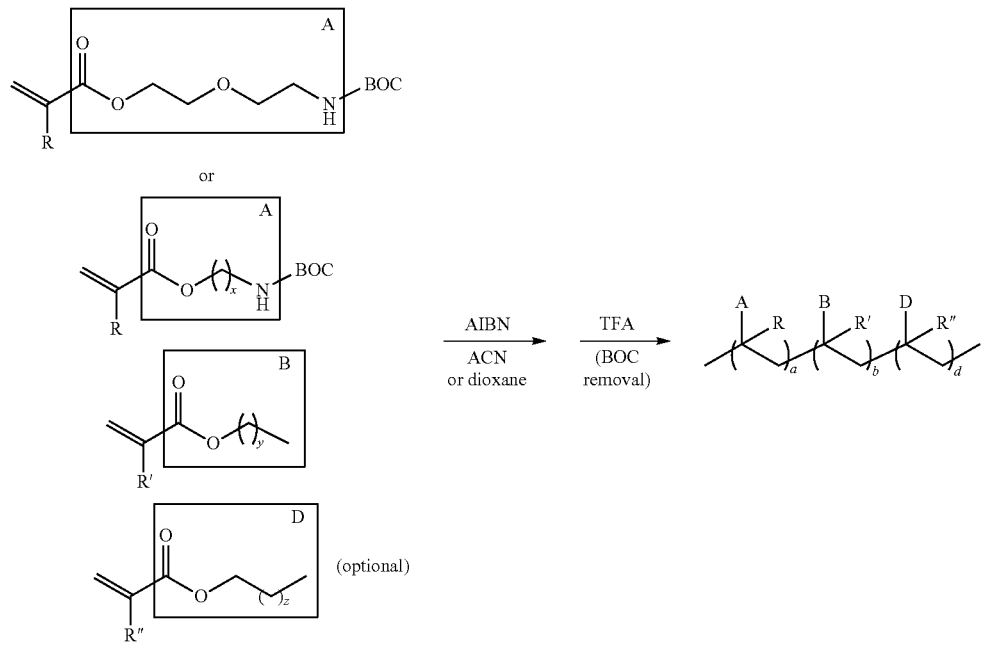

R, R', and R" are independently hydrogen or methyl
x=2, 3, or 4
y=0, 1, 2, 3, 4, or 5 [methyl (C1)-hexyl (C6)]
z=integer ≥8 [decyl (C10) or greater]
a, b, and d are integers selected such that the polymer has the desired ratio of monomers as described above.

X mol % amine-protected acrylate monomer, Y mol % lower hydrophobic group acrylate monomer, and optionally Z mol % higher hydrophobic group acrylate monomer are added to a reaction tube equipped with a stir bar. An appropriate solvent (e.g., acetonitrile or dioxane) is added, followed by an appropriate catalyst (e.g., AIBN), and the reaction mixture is purged with $N_2$. The reaction tubes are then capped and transferred to an oil bath and heated (e.g., 60° C.) for sufficient time to allow polymerization (e.g., 3 h). The crude polymer may be purified by appropriate means, including but not limited to dialysis, column chromatography, and precipitation, prior to removal of the BOC protecting groups. The BOC protecting groups are removed by reaction with 2M HCl in glacial acetic acid. Removal of the BOC protecting groups yield polymer primary amines and a water soluble membrane active poly(acrylate) polyamine. The polymer may then be purified by appropriate means, including dialysis, column chromatography, and precipitation.

Synthesis of (Ant 40911-3 23-28, Ant 40911-35-2)

2,2'-Azobis(2-methylpropionitrile) (AIBN, radical initiator), acetonitrile, and dioxane were purchased from Sigma Aldrich. Acrylate and methacrylate monomers were filtered to remove inhibitors. 3-(BOC-amino)1-propanol (TCI) was reacted with acryloyl chloride (CAS 814-68-6) to produce BOC-amino propyl acrylate (BAPA).

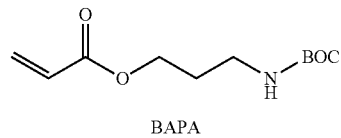 [SMILES: C=CC(=O)OCCCNC(=O)OC(C)(C)C]

BAPA

In a 2 L round-bottom flask equipped with a stir bar, 2-(2-aminoethoxy)ethanol (21.1 g, 202.9 mmol) was dissolved in 350 mL dichloromethane. In a separate 1 L flask, BOC anhydride (36.6 g, 169.1 mmol) was dissolved in 660 mL dichloromethane. The 2 L round-bottom flask was fitted with an addition funnel and BOC anhydride solution was added to the flask over 6 h. The reaction was left to stir overnight. In a 2 L separatory funnel, the product was washed with 300 ml each of 10% citric acid, 10% $K_2CO_3$, sat. $NaHCO_3$, and sat. NaCl. The product, BOC protected 2-(2-aminoethoxy)ethanol, was dried over $Na_2SO_4$, gravity filtered, and DCM was evaporated using rotary evaporation and high vacuum.

In a 500 ml round bottom flask equipped with a stir bar and flushed with argon, BOC protected 2-(2-aminoethoxy) ethanol (27.836 g, 135.8 mmol) was added, followed by 240 mL anhydrous dichloromethane. Diisopropylethyl amine (35.5 ml, 203.7 mmol) was added, and the system was placed in a dry ice/acetone bath. Acryloyl Chloride (12.1 ml, 149.4 mmol) was diluted using 10 ml of dichloromethane, and added drop-wise to the argon flushed system. The system was kept under argon and left to come to room temperature and stirred overnight. The product was washed with 100 mL each of $dH_2O$, 10% citric acid, 10% $K_2CO_3$, sat. $NaHCO_3$, and saturated NaCl. The product, BOC-amino ethyl ethoxy acrylate (BAEEA), was dried over $Na_2SO_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30. Fractions were collected and solvent was removed using rotary evaporation and high vacuum. BAEEA, was obtained with 74% yield. BAEEA was stored in the freezer.

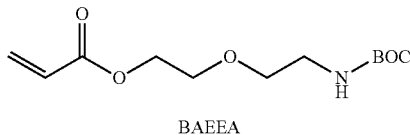 [SMILES: C=CC(=O)OCCOCCNC(=O)OC(C)(C)C]

BAEEA

Polymer 40911-3 23-28

70% BAPA, 25% butyl methacrylate (CAS 97-88-1), 5% octadecyl methacrylate (CAS 4813-57-4), (3% AIBN catalyst) mole feed ratio (0.0139 total mol). BAPA (9.739 mmol) (A), butyl methacrylate (3.478 mmol) (B), and octadecyl methacrylate (0.6957 mmol) (D) were added to a 20 mL reaction tube equipped with a stir bar. Acetonitrile (16 ml) was added, followed by AIBN (0.4174 mmol). The above steps were repeated in order to have two reactions run in tandem. The reaction mixture was purged with Na for 30 min. The reaction tubes were then capped and transferred to an oil bath and heated at 60° C. for 3 h. The tubes were removed and the contents were combined. The crude polymer was precipitated into deionized water, and reacted with neat trifluoroacetic acid (40 ml) for 1.5 h to remove the BOC protecting groups and produce the primary amines and a water soluble membrane active poly(acrylate) polyamine. 200 mL deionized $H_2O$ ($dH_2O$) were added to the reaction, the solution was transferred to 3500 MW cutoff cellulose tubing, dialyzed against high salt for 24 h, then against $dH_2O$ for 18 h. The contents were evaporated to dryness, dissolved in 100 mL $dH_2O$ and lyophilized. The dried polymer was dissolved in 50% MeOH/100 mM ammonium formate/0.2% formic acid solution at 25 mg/ml. Three injections of crude polymer solution (250 mg, 10 ml) were purified on S-200 sephacryl media using an XK50/30 cm column used at a flow rate of 5.0 ml/min. The column was packed and used according to the manufacturer's instructions. (GE Healthcare, instructions 56-1130-82 Al, 52-2086-00 AK). Polymer elution was detected using a Shimadzu RID-10A refractive index collector. Fractions from 23 min to 28 min were collected and combined for each run. The solvent was evaporated and the purified polymer was lyophilized twice.

Polymer Ant 40911-35-2

80% BAEEA, 15% butyl methacrylate, 5% octadecyl acrylate, (3% AIBN catalyst) mole feed ratio (0.013913 total mol). BAEEA (A) (11.13 mmol), butyl methacrylate (B) (2.086 mmol), and octadecyl acrylate (D) (0.6957 mmol) were added to a 20 mL reaction tube equipped with a stir bar. Dioxane (16 ml) was added, followed by AIBN (0.4174 mmol). The above steps were repeated in order to have two reactions run in tandem. The reaction mixture was purged with $N_2$ for 30 min. The reaction tubes were then capped and transferred to an oil bath and heated at 60° C. for 3 h. The tubes were removed and the contents were combined. Dioxane was evaporated through rotary evaporation and high vacuum and the crude polymer was dissolved in 89.8% dichloromethane/10% tetrahydrofuran/0.2% triethylamine solution at 70 mg/ml. Three injections of crude polymer solution (700 mg, 10 ml) were purified on a Jordi gel divinyl benzene $10^4$ Å column (internal diameter: 22 mm, length: 500 mm) used at a flow rate of 5.0 ml/min. Polymer elution was detected using a Shimadzu RID-10A refractive index collector. Fractions from 15.07 min-17.13 min were collected and combined. The solvent was evaporated through rotary evaporation.

Approximately 10 mg of the polymer was dissolved in 0.5 mL 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5µ 7.8×300 Mixed Bed LS DVB column. A molecular weight of 172,000 and a PDI of 1.26 were obtained.

The purified BOC-protected polymer was reacted with neat trifluoroacetic acid (7 ml) for 1.5 h (or 2 M HCl in glacial acetic acid for 0.5 h) to remove the BOC protecting groups and produce the amines. 40 mL $dH_2O$ were added to the reaction, the solution was transferred to 3500 MW cutoff cellulose tubing, dialyzed against high salt for 24 hr, then against $dH_2O$ for 18 h. The contents were evaporated to dryness, then dissolved in 20-30 mL $dH_2O$ and lyophilized twice. The polymer solution was stored at 2-8° C.

The number of carbon atoms linking the amine to the backbone of the polymer and whether or not the linker is branched, affects the pKa of the amine and steric effects near the amine. For example, for the above polymers, ethyl amine has a pKa of about 8.1, propyl amine has a pKa of about 9.3, and pentyl amine has a pKa of about 10.2. The pKa of the amine or steric effects near the amine affect the lability of masking groups attached to the amine. For reversible attachment of a maleic anhydride to an amine, a higher pKa of the amine results is a slower rate of release of an anhydride from the amine. Also, increased steric hindrance near the amine, such as with an isopropyl linker, may increase the pKa of the amine.

Polymer Lau 41305-38-17-19

80% BAPA, 20% ethyl methacrylate (CAS 97-63-2), (3% AIBN catalyst) mole feed ratio (0.0105 total mol). BAPA (A) (8.40 mmol) and ethyl methacrylate (B) (2.10 mmol) were added to a 15 mL reaction tube equipped with a stir bar. Acetonitrile (11.5 ml) was added followed by AIBN (0.315 mmol). The above steps were repeated in order to have two reactions run in tandem. The reaction mixture was purged with $N_2$ for 30 min. The reaction tubes were then capped and transferred to an oil bath and heated at 60° C. for 3 h. The tubes were removed and the contents were combined. Acetonitrile was evaporated through rotary evaporation and high vacuum and the crude polymer was dissolved in 74.8% dichloromethane/25% tetrahydrofuran/0.2% triethylamine solution at 50 mg/ml. Three injections of crude polymer solution (500 mg, 10 ml) were purified on a Jordi gel fluorinated divinyl benzene $10^4$ Å column (internal diameter: 22 mm, length: 500 mm) used at a flow rate of 5.0 ml/min. Polymer elution was detected using a Shimadzu RID-10A refractive index collector. Fractions from 17.16 min-19.18 min were collected and combined. The solvent was evaporated through rotary evaporation. The purified BOC-protected polymer was reacted with 2M HCl in glacial acetic acid (7 ml) for 1.5 h to remove the BOC protecting groups and produce the amines. 40 mL $dH_2O$ were added to the reaction, the solution was transferred to 3500 MW cutoff cellulose tubing, dialyzed against high salt for 24 hr, then against dH$_2$O for 18 h. The contents were evaporated to dryness, then dissolved in 30 mL dH$_2$O and lyophilized twice.

F. Similar Polymers, Synthesized from (Protected) Amine Monomers, Lower Hydrophobic Group Monomers, and Higher Hydrophobic Group Octadecyl Groups would be Predicted to be Effective in the Practice of the Described Invention Polymer Characterization Example 2. Characterization of DW1360

A. Amphipathic Analysis 1,6-diphenyl-1,3,5-hexatriene (DPH, Invitrogen) fluorescence ($\lambda_{ex}$=350 nm; $\lambda_{em}$=452 nm) is enhanced in a hydrophobic environment. This fluorophore was used to analyze the DW1360 polymer. 0.5 µM (final concentration) DPH was added to 10 µg DW1360 in 0.5 mL 50 mM HEPES buffer, pH 8.0. The solution was then tested for DPH accumulation in a hydrophobic environment by measuring fluorescence of DPH. Increased DPH fluorescence in the presence of the conjugates indicates the formation of a hydrophobic environment by the polymer.

B. Molecular Weight

Polymer Molecular Weights (mass) (MW) were determined on a Wyatt Dawn Heleos II run in conjunction with optilab rEX in batch mode. Polymers was brought up at varying concentrations in appropriate solvent and each was loaded onto the Wyatt system. Astra software then calculated changes in refractive index as a function of concentration (dn/dc) which was used in a Zimm plot to calculate MW. The average molecular weight determined for purified DW1360 was 4000-6000 Da. The average molecular weight for the purified acrylate polymers was about 100-120 kDa.

C. Particle Sizing and Zeta Potential

The zeta potential of the polymers was measured using a Malvern Zetasizer nano series (Nano ZS) instrument. The zeta potential of the CDM-masked polymers varied between 0 and −30 mV and more predominantly between 0 and −20 mV. Zeta potential was measured in isotonic glucose buffered at pH 8 with residual HEPES. At pH 7, the conjugates would be expected to gain some positive charge due to protonation of some of the amines.

D. Quantification of Amine Groups in Conjugate after CDM-Reagent Modification

DW1360 polymer was synthesized as described previously followed by treatment with 14 wt equivalents HEPES base and 7 wt equivalents of a 2:1 wt:wt mixture of CDM-NAG and CDM-PEG (average 11 units). One hour later, the amine content of the maleic anhydride derivative treated conjugate was measured by treatment with trinitrobenzene sulfonic acid (TNBS) in 100 mM NaHCO$_3$. When normalized to a conjugate that had not been maleamate modified, it was determined that the amount of modified amines was about 75% of total. This degree of modification may be varied by changing the amount of added maleic anhydride or altering the reaction conditions.

E. Liposome Lysis 10 mg of egg phosphatidylcholine was hydrated with 1 mL of buffer containing 100 mM carboxyfluorescein (CF) and 10 mM HEPES pH 7.5. Liposomes were then be extruded through 100-nm pores polycarbonate filters (Nucleopore, Pleasanton, Calif.). Unentrapped CF was removed by size exclusion chromatography using Sepharose 4B-200 eluting with 10 mM HEPES at pH 8 and 0.1 mol/L NaCl. A 200 µL aliquot of the CF-loaded liposomes were added to 1.8 mL of isotonic buffer. Fluorescence ($\lambda_{ex}$=488, $\lambda_{em}$=540) was measured 30 min after addition of 0.25 µg of polymers to vesicle suspensions. At the end of each experiment, vesicles were disrupted by the addition of 40 µl of a 1% Triton X-100 solution to determine maximal lysis.

Example 3. Melittin Amphipathic Polymer Peptides

TABLE 1

Melittin peptides demonstrated to exhibit high membrane activity.

| Melittin Amino Acid Sequence having high Membrane activity | | Reversibly inhibited[b] |
|---|---|---|
| GIGAVLKVLTTGLPALISWIKRKRQQ | SEQ ID 5 | + |
| GIGAVLKVLTTGLPALISWISRKKRQQ | SEQ ID 6 | n.d. |
| GIGARLKVLTTGLPR ISWIKRKRQQ | SEQ ID 7 | n.d. |
| GIGAILKVLSTGLPALISWIKRKRQE | SEQ ID 8 | n.d. |
| GIGAVLKVLTTGLPALIGWIKRKRQQ | SEQ ID 9 | n.d. |
| GIGAVLKVLATGLPALISWIKRKRQQ | SEQ ID 10 | n.d. |
| GIGAVLKVLSTGLPALISWIKRKRQQ | SEQ ID 11 | n.d. |
| GIGAILKVLATGLPTLISWIKNKRKQ | SEQ ID 12 | + |
| YIGAILKVLATGLPTLISWIKNKRKQ | SEQ ID 13 | n.d. |
| GIGAILHVLATGLPTLISWIHHHQQ | SEQ ID 14 | n.d. |
| GIGAILKVLATGLPTLISWIRNRRRQ | SEQ ID 15 | − |

TABLE 1-continued

Melittin peptides demonstrated to exhibit high membrane activity.

| Melittin Amino Acid Sequence having high Membrane activity | | Reversibly inhibited[b] |
|---|---|---|
| GIGAILRVLATGLPTLISWIKNKRKQ | SEQ ID 16 | n.d. |
| GIGAILKVLATGLPTLISWIKRKRKQ | SEQ ID 17 | + |
| GIGAILKVLATGLPTLISWIKKKKQQ | SEQ ID 18 | + |
| GIGAILKVLATGLPTLISWIKNKRKQGSKKKK | SEQ ID 19 | + |
| KKGIGAILKVLATGLPTLISWIKNKRKQ | SEQ ID 20 | + |
| GIGAILEVLATGLPTLISWIKNKRKQ | SEQ ID 21 | + |
| GIGAVLSVLTTGLPALISWIKR | SEQ ID 22 | n.d. |
| GIGAVLKVLTTGLPALISWIKRKR | SEQ ID 23 | n.d. |
| GIGAVLKVLTTGLPALISWIKR | SEQ ID 24 | n.d. |
| Ac-CIGAVLKVLTTGLPALISWIKRKRQQ-NH$_2$ | SEQ ID 25 | + |
| (Ac-CIGAVLKVLTTGLPALISWIKRKRQQ-NH$_2$)$_2$ | core sequence disclosed as SEQ ID 26 | + |
| QQRKRKIWSILAPLGTTLVKLVAGIG-NH$_2$ | SEQ ID 27 | n.d. |
| QQRKRKIWSILAPLGTTLVKLVAGIC-NH$_2$ | SEQ ID 28 | + |
| QQRKRKIWSILAALGTTLVKLVAGIC-NH$_2$ | SEQ ID 29 | + |
| QQKKKKIWSILAPLGTTLVKLVAGIC-NH$_2$ | SEQ ID 30 | + |
| QQRKRKIWSILAPLGTTLVKLVAGIC(N-PDP-PE[a])-NH$_2$ | SEQ ID 31 | + |
| QKRKNKIW SILTPLGTALVKLIAGIG-NH$_2$ | SEQ ID 32 | + | n.d. - not determined
[a] - Dioleolyl Phosphatidyl Ethanolamine
[b] - modification with CDM, CDM-gal, or CDM-PEG or a combination thereof inhibits membrane activity.

Masking Agents

Example 4. Masking Agents

A. Synthesis of 2-Propionic-3-Methylmaleic Anhydride Masking Agent Precursor (Carboxydimethylmaleic Anhydride or CDM)

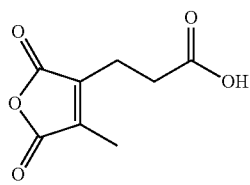

2-propionic-3-methylmaleic anhydride

To a suspension of sodium hydride (0.58 g, 25 mmol) in 50 mL anhydrous tetrahydrofuran was added triethyl-2-phosphonopropionate (7.1 g, 30 mmol). After evolution of hydrogen gas had stopped, dimethyl-2-oxoglutarate (3.5 g, 20 mmol) in 10 mL anhydrous tetrahydrofuran was added and stirred for 30 min. 10 mL water was then added, and the tetrahydrofuran was removed by rotary evaporation. The resulting solid and water mixture was extracted with 3×50 mL ethyl ether. The ether extractions were combined, dried with magnesium sulfate, and concentrated to a light yellow oil. The oil was purified by silica gel chromatography elution with 2:1 ether:hexane to yield 4 g (82% yield) of pure triester. The 2-propionic-3-methylmaleic anhydride was then formed by dissolving of this triester into 50 mL of a 50/50 mixture of water and ethanol containing 4.5 g (5 equivalents) of potassium hydroxide. This solution was heated to reflux for 1 h. The ethanol was then removed by rotary evaporation and the solution was acidified to pH 2 with hydrochloric acid. This aqueous solution was then extracted with 200 mL ethyl acetate, isolated, dried with magnesium sulfate, and concentrated to a white solid. This solid was then recrystallized from dichloromethane and hexane to yield 2 g (80% yield) of 2-propionic-3-methylmaleic anhydride.

Thioesters, esters, and amides may be synthesized from CDM by conversion of CDM to its acid chloride with oxalyl chloride followed by the addition of a thiol, ester, or amine and pyridine. CDM and its derivatives are readily modified, by methods standard in the art, with targeting ligands, steric stabilizers, charged groups, and other reactive groups. The resultant molecules can be used to reversibly modify amines.

Masking agents were synthesized through modification of CDM to produce preferably charge neutral agents:

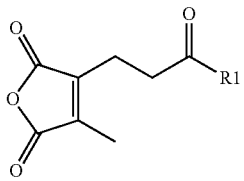

wherein R1 comprises an ASGPr targeting ligand or steric stabilizer (e.g. PEG).

B. Masking Agent Containing an ASGPr Targeting Group

The most widely-studied hepatocyte targeting ligands are based on galactose, which is bound by the asialoglycoprotein receptor (ASGPr) on hepatocytes. Attachment of galactose or a galactose derivative has been shown to facilitate hepatocyte targeting of a few highly water soluble, uncharged polymers, including: the oligosaccharide chitosan, a polystyrene derivative, and a polyacrylamide HPMA. ASGPr targeting groups are readily generated using lactose, a galactose-glucose disaccharide, via modification of the glucose residue. Lactobionic acid (LBA, a lactose derivative in which the glucose has been oxidized to gluconic acid) is readily incorporated into a maleic anhydride derivative using standard amide coupling techniques.

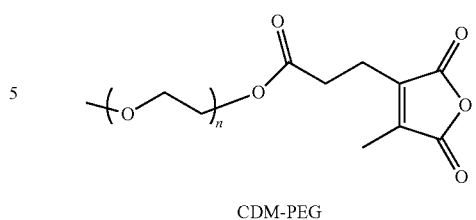

CDM-PEG

Preferably, PEG containing from 5 to 20 ethylene units are attached to the di-substituted maleic anhydride. More preferably, PEG containing 10-14 ethylene units are attached to the di-substituted maleic anhydride. The PEG may be of variable length and have a mean length of 5-20 or 10-14 ethylene units. Alternatively, the PEG may be monodisperse, uniform or discrete; having, for example, exactly 11 or 13 ethylene units.

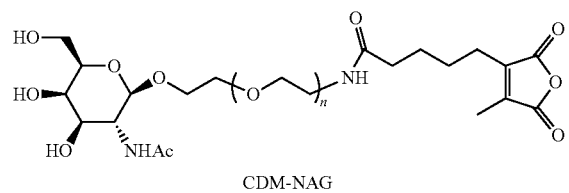

CDM-NAG

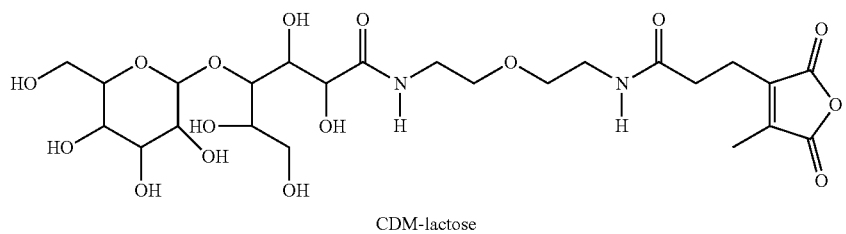 [SMILES: CC1=C(CCC(=O)NCCOCCNC(=O)C(O)C(O)C(OC2OC(CO)C(O)C(O)C2O)C(O)CO)C(=O)OC1=O]

CDM-lactose

C. Steric Stabilizer CDM-PEG and Targeting Group CDM-NAG (N-Acetyl Galactosamine) Syntheses To a solution of CDM (300 mg, 0.16 mmol) in 50 mL methylene chloride was added oxalyl chloride (2 g, 10 wt. eq.) and dimethylformamide (5 µl). The reaction was allowed to proceed overnight, after which the excess oxalyl chloride and methylene chloride were removed by rotary evaporation to yield the CDM acid chloride. The acid chloride was dissolved in 1 mL of methylene chloride. To this solution was added 1.1 molar equivalents polyethylene glycol monomethyl ether (MW average 550) for CDM-PEG or (aminoethoxy)ethoxy-2-(acetylamino)-2-deoxy-β-D-galactopyranoside (i.e. amino bisethoxy-ethyl NAG) for CDM-NAG, and pyridine (200 µl, 1.5 eq) in 10 mL of methylene chloride. The solution was then stirred 1.5 h. The solvent was then removed and the resulting solid was dissolved into 5 mL of water and purified using reverse-phase HPLC using a 0.1% TFA water/acetonitrile gradient.

As shown above, a PEG spacer may be positioned between the anhydride group and the ASGPr targeting group. A preferred PEG spacer contains 1-10 ethylene units.

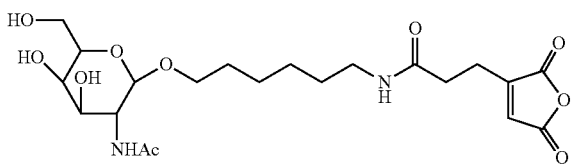

CDM-NAG with alkyl spacer

Reversible Polymer Modification

Example 5. Reversible Modification/Masking of Membrane Active Polyamine; i.e., Modification of Membrane Active Polymer with CDM-NAG or a Mixture of CDM-NAG Plus CDM-PEG To a solution of xmg membrane active polyamine (e.g. DW1360 described above) in isotonic glucose was added 14×mg of HEPES free base followed by either 7×mg CDM-NAG or a mixture of 2.3×mg CDM-NAG and 4.6×mg CDM-PEG, for a total of 7×disubstituted maleic anhydride masking agent. The solution was then incubated for at least 30 min at RT prior to animal administration. Reaction of CDM-NAG or CDM-PEG with the polyamine yielded:

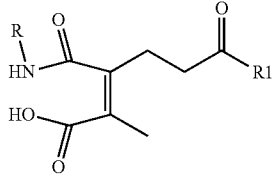

wherein R is the polymer and R1 comprises a ASGPr targeting moiety or steric stabilizer. The anhydride carboxyl produced in the reaction between the anhydride and the polymer amine exhibits ~1/20$^{th}$ of the expected charge (Rozema et al. Bioconjugate Chemistry 2003). Therefore, the membrane active polymer is effectively neutralized rather than being converted to a highly negatively charged polyanion.

Example 6. Reversible Modification/Masking of Melittin with CDM-NAG

Prior to modification, 5×mg of CDM-NAG was lyophilized from a 0.1% aqueous solution of glacial acetic acid. To the dried NAG derivative was added a solution of ×mg melittin in 0.2×mL of isotonic glucose and 10×mg of HEPES free base. Following complete dissolution of CDM-NAG, the solution was then incubated for at least 30 min at RT prior to animal administration. Reaction of CDM-NAG with the peptide yielded:

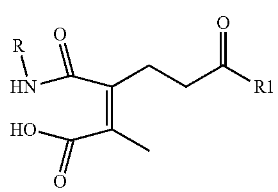

wherein R is melittin and R1 comprises the ASGPr targeting moiety NAG. The anhydride carboxyl produced in the reaction between the anhydride and the polymer amine exhibits ~1/20$^{th}$ of the expected charge (Rozema et al. Bioconjugate Chemistry 2003). Therefore, the membrane active polymer is effectively neutralized rather than being converted to a highly negatively charged polyanion.

siRNA-Conjugate

Example 7. Synthesis of GalNAc Cluster

A. Synthesis of {2-[2-(2-Hydroxy-ethoxy)-ethoxy]-ethoxy}-acetic acid benzyl ester 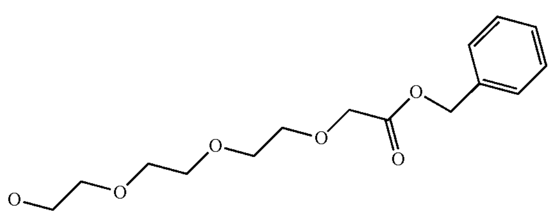 [SMILES: O=C(COCCOCCOCCO)OCc1ccccc1] 2-[2-(2-Hydroxy-ethoxy)-ethoxy]-ethanol (62.2 g, 414 mmol) was dissolved under argon in 875 mL of abs. DMF and cooled to 0° C. NaH (12.1 g, 277 mmol, 55% in mineral oil) was carefully added, the ice bath removed, and stirring continued for 1 h at 80° C. The reaction mixture was cooled to ambient temperature and treated with bromoacetic acid (18.98 g, 137 mmol) which was added via dropping funnel as a DMF-solution (20 mL). After an additional 30 min. at 75° C., bromomethyl-benzene (23.36 g, 137 mmol) was added neat and esterification allowed to proceed for 30 min. Cooling, careful pouring onto crushed ice, extraction with ethyl acetate, washing with water, drying over $Na_2SO_4$, and evaporation of all solvents, followed by flash chromatography ($SiO_2$, ethyl acetate/heptane=8/2) yielded 6.41 g of the title compound as a yellow oil. MS (ISP): 299.2 $[M+H]^+$.

B. Acetic acid (3aR,5R,6R,7R,7aR)-6-acetoxy-5-acetoxymethyl-2-methyl-5,6,7,7a-tetrahydro-3aH-pyrano[3,2-d]oxazol-7-yl ester 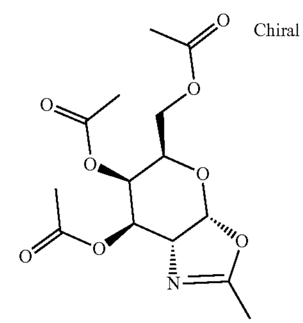 [SMILES: CC(=O)OC[C@H]1O[C@@H]2OC(C)=N[C@@H]2[C@@H](OC(C)=O)[C@H]1OC(C)=O] Commercially available acetic acid (2S,3R,4R,5R,6R)-4,5-diacetoxy-6-acetoxymethyl-3-acetylamino-tetrahydro-pyran-2-yl ester (10.0 g, 26 mmol) was dissolved in 116 mL of abs. $CH_2Cl_2$ and treated with trimethylsilyl triflate (14.27 g, 64 mmol). The reaction was allowed to proceed over night at 45° C. After cooling to 0° C., triethylamine (4.88 mL, 35 mmol) was added, the mixture diluted with $CH_2Cl_2$ and washed with $NaHCO_3$-solution and water. Drying over $Na_2SO_4$ and evaporation of the solvent yielded 10.3 g of the title compound as brownish oil which was used without further purification for the next step. MS (ISP): 330.0 $[M+H]^+$.

C. (2-{2-[2-((2R,3R,4R,5R,6R)-4,5-Diacetoxy-6-acetoxymethyl-3-acetylamino-tetrahydro-pyran-2-yloxy)-ethoxy]-ethoxy}-ethoxy)-acetic acid benzyl ester The above prepared acetic acid (3aR,5R,6R,7R,7aR)-6-acetoxy-5-acetoxymethyl-2-methyl-5,6,7,7a-tetrahydro-3aH-pyrano[3,2-d]oxazol-7-yl ester (10.3 g, 26 mmol) and {2-[2-(2-hydroxy-ethoxy)-ethoxy]-ethoxy}-acetic acid benzyl ester (8.62 g, 29 mmol) were mixed in 520 mL of CH$_2$Cl$_2$ and treated with 63 g of molecular sieves 4 Angstrom. After 1 h, trimethylsilyl triflate (6.13 g, 28 mmol) was added. The reaction mixture was stirred over the weekend at ambient temperature. Triethylamine (5.21 mL, 37 mmol) was added, the molecular sieves filtered off, the filtrate diluted with CH$_2$Cl$_2$ and washed with NaHCO$_3$-solution and water. Drying over Na$_2$SO$_4$ and evaporation of the solvent followed by flash chromatography (SiO$_2$, ethyl acetate/AcOH/MeOH/water=60/3/3/2) afforded 15.7 g of the title compound as a brownish oil. MS (ISP): 626.6 [M−H]$^-$.

D. (2-{2-[2-((2R,3R,4R,5R,6R)-4,5-Diacetoxy-6-acetoxymethyl-3-acetylamino-tetrahydro-pyran-2-yloxy)-ethoxy]-ethoxy}-ethoxy)-acetic acid

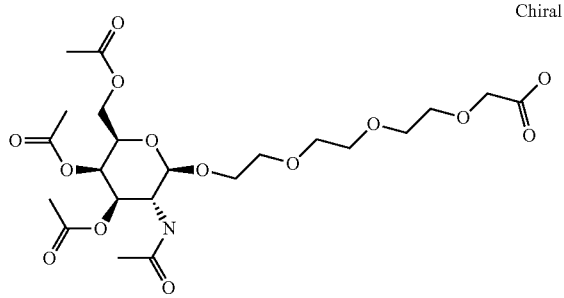 [SMILES: CC(=O)N[C@H]1[C@H](OCCOCCOCCOCC(=O)O)O[C@H](COC(C)=O)[C@H](OC(C)=O)[C@@H]1OC(C)=O]

The above prepared (2-{2-[2-((2R,3R,4R,5R,6R)-4,5-diacetoxy-6-acetoxymethyl-3-acetylamino-tetrahydro-pyran-2-yloxy)-ethoxy]-ethoxy}-ethoxy)-acetic acid benzyl ester (15.7 g, 25 mmol) was dissolved in 525 mL of ethyl acetate and hydrogenated over 1.6 g of Pd/C (10%) under 1 atm. Of H$_2$ at ambient temperature for 3 h. Filtration over Celite, evaporation of the solvent, followed by flash chromatography (SiO$_2$, CH$_2$Cl$_2$/MeOH=80/20) gave 6.07 g of the title compound as a brownish gum. MS (ISP): 536.5 [M−H]$^-$.

E. Acetate Protected GalNAc Cluster Benzyl Ester

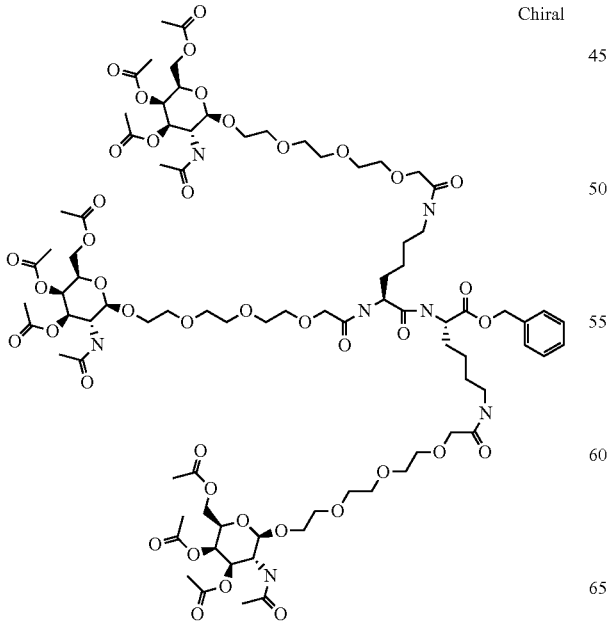

The above prepared (2-{2-[2-((2R,3R,4R,5R,6R)-4,5-diacetoxy-6-acetoxymethyl-3-acetylamino-tetrahydro-pyran-2-yloxy)-ethoxy]-ethoxy}-ethoxy)-acetic acid (2.820 g, 5.246 mmol) and (S)-6-amino-2-((S)-2,6-diamino-hexanoylamino)-hexanoic acid benzyl ester hydrochloride (preparation see below, 0.829 g, 1.749 mmol) were dissolved in a mixture of 32 mL of CH$_2$Cl$_2$ and 3.2 mL of DMF, treated successively with Hünig's base (2.096 mL, 12.25 mmol), 1-hydroxy-7-azabenzotriazole (0.714 g, 5.248 mmol) and 1-(3-dimethylaminopropyl)-3-ethylcarbodiimide hydrochloride (1.006 g, 5.248 mmol), and stirred over night at ambient temperature. All volatiles were removed i.V. and the crude reaction mixture purified by preparative HPLC (38 runs, Gemini, 5µ, C18) to give after lyophilization 1.650 g of the title product as white powder. MS (ISP): 1945.8 [M+Na]$^+$.

F. Acetate Protected GalNAc Cluster Free Acid (Sugar Hydroxyls Protected). (17S,20S)-1-((2R,3R,4R,5R,6R)-3-acetamido-4,5-diacetoxy-6-(acetoxymethyl)tetrahydro-2H-pyran-2-yloxy)-20-(1-((2R,3R,4R,5R,6R)-3-acetamido-4,5-diacetoxy-6-(acetoxymethyl)tetra-hydro-2H-pyran-2-yloxy)-11-oxo-3,6,9-trioxa-12-azahexadecan-16-yl)-17-(2-(2-(2-(2-((2R,3R,4R,5R,6R)-3-acetamido-4,5-diacetoxy-6-(acetoxymethyl)tetrahydro-2H-pyran-2-yloxy)ethoxy)ethoxy)ethoxy)-acetamido)-11,18-dioxo-3,6,9-trioxa-12,19-diazahenicosan-21-oic acid

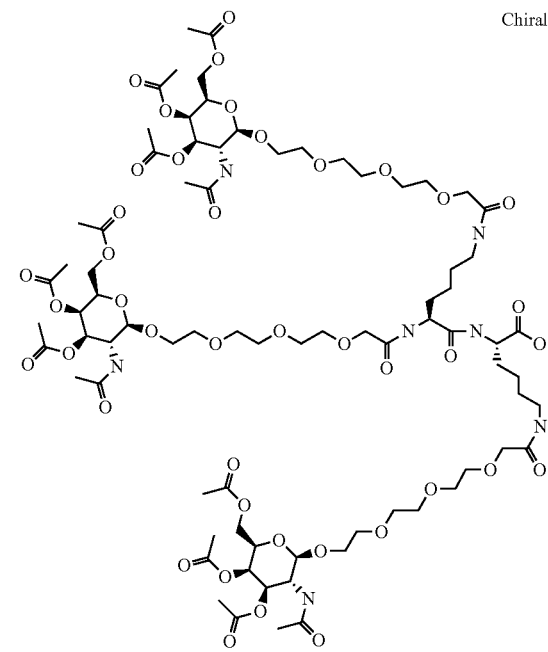 [SMILES: CC(=O)N[C@H]1[C@H](OCCOCCOCCOCC(=O)NCCCC[C@H](NC(=O)[C@H](CCCCNC(=O)COCCOCCOCCO[C@@H]2O[C@H](COC(C)=O)[C@H](OC(C)=O)[C@H](OC(C)=O)[C@H]2NC(C)=O)NC(=O)COCCOCCOCCO[C@@H]2O[C@H](COC(C)=O)[C@H](OC(C)=O)[C@H](OC(C)=O)[C@H]2NC(C)=O)C(=O)O)O[C@H](COC(C)=O)[C@H](OC(C)=O)[C@@H]1OC(C)=O]

The above prepared GalNAc Cluster benzyl ester (0.674 g, 0.350 mmol) was dissolved in 50 mL of MeOH and hydrogenated over 0.065 g of Pd/C (10%) under 1 atm. of H$_2$ at ambient temperature for 4 h. Filtration over Celite and evaporation of the solvent left 0.620 g of the title compound as a white foam. MS (ISP): 1917.0 [M+2H]$^{2+}$.

Example 8. Synthesis of Galactose Cluster Branch Point, (S)-6-amino-2-((S)-2,6-diamino-hexanoylamino)-hexanoic acid benzyl ester hydrochloride

A. (S)-6-tert-Butoxycarbonylamino-2-(9H-fluoren-9-ylmethoxycarbonylamino)-hexanoic acid benzyl ester

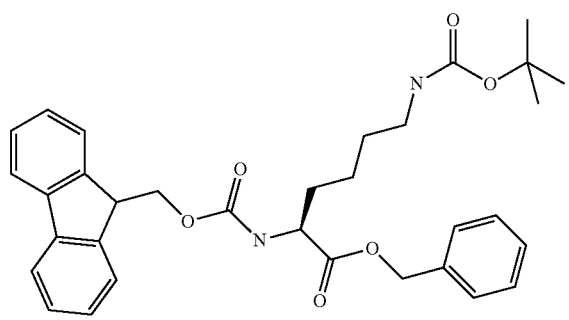 [SMILES: CC(C)(C)OC(=O)NCCCC[C@H](NC(=O)OCC1c2ccccc2-c2ccccc21)C(=O)OCc1ccccc1]

(S)-6-tert-Butoxycarbonylamino-2-(9H-fluoren-9-ylmethoxycarbonylamino)-hexanoic acid (5.00 g, 10.67 mmol) and phenyl-methanol (2.305 g, 21.34 mmol) were dissolved in 25 mL of $CH_2Cl_2$ and treated successively with N-hydroxybenzotriazole (1.933 g, 11.74 mmol), 1-ethyl-3-(3-dimethylaminopropyl)carbodiimide hydrochloride (EDC, 2.250 g, 11.74 mmol), and ethyl-diisopropyl-amine (2.137 mL, 12.49 mmol). After stirring for 90 min, the volatiles were removed i.v. at ambient temperature, the residue taken up in ethyl acetate, washed with water, $NH_4Cl$-solution and brine, dried over $Na_2SO_4$ and evaporated. The crude mixture was then dissolved in 20 mL of ethanol and the product precipitated by adding 10 mL of water. Filtration and drying yielded 5.669 g of the title compound which was recrystallized from ethanol/hexane to give 4.27 g of pure benzyl ester. MS (ISP): 559.2 $[M+H]^+$.

B. (S)-2-((S)-2,6-Bis-tert-butoxycarbonylamino-hexanoylamino)-6-tert-butoxy-carbonylamino-hexanoic acid benzyl ester

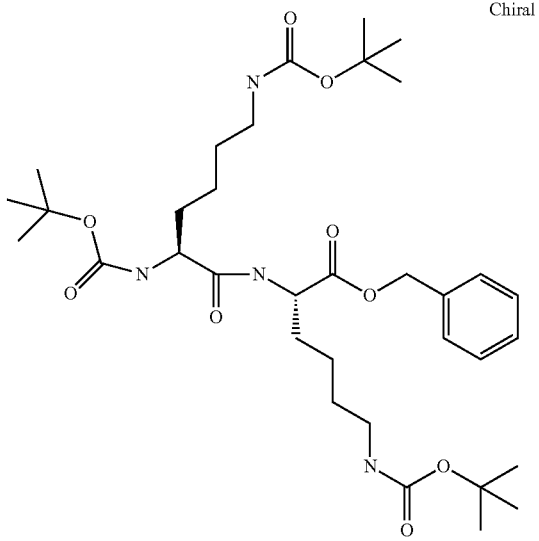 [SMILES: CC(C)(C)OC(=O)NCCCC[C@H](NC(=O)OC(C)(C)C)C(=O)N[C@@H](CCCCNC(=O)OC(C)(C)C)C(=O)OCc1ccccc1]

The above prepared (S)-6-tert-Butoxycarbonylamino-2-(9H-fluoren-9-ylmethoxycarbonyl-amino)-hexanoic acid benzyl ester (4.270 g, 7.643 mmol) was dissolved in 15 mL of THF and treated with 15 mL of diethylamine. After 4 h at ambient temperature MS and TLC indicated the absence of starting material. Evaporation of the solvents and azeotropic drying with toluene afforded 4.02 g of the free amine which was used directly in the next step.

Commercially available (S)-2,6-bis-tert-butoxycarbonylamino-hexanoic acid (3.177 g, 9.17 mmol) was dissolved in 13 mL of $CH_2Cl_2$ and treated at 0° C. with ethyl-diisopropyl-amine (4.71 mL, 27.5 mmol), O-(1,2-dihydro-2-oxo-pyridyl)-1,1,3,3-tetramethyluronium tetrafluoroborate (TPTU, 2.725 g, 9.172 mmol). After 15 minutes, with the above prepared amine as a solution in minimal $CH_2Cl_2$ and 1.57 mL of ethyl-diisopropyl-amine (1.2 eq.), the reaction was allowed to proceed for 2 h at ambient temperature. All volatiles were removed i.v., the residue taken up in ethyl acetate, washed with $NaHCO_3$-solution, $NH_4Cl$-solution and water, dried over $Na_2SO_4$ and evaporated. Flash chromatography ($SiO_2$, heptane/ethyl acetate=4/6), followed by crystallization from heptane/minimal amounts of ethyl acetate produced 4.516 g of the title compound as a white solid. MS (ISP): 665.4 $[M+H]^+$.

C. (S)-6-Amino-2-((S)-2,6-diamino-hexanoylamino)-hexanoic acid benzyl ester trihydrochloride

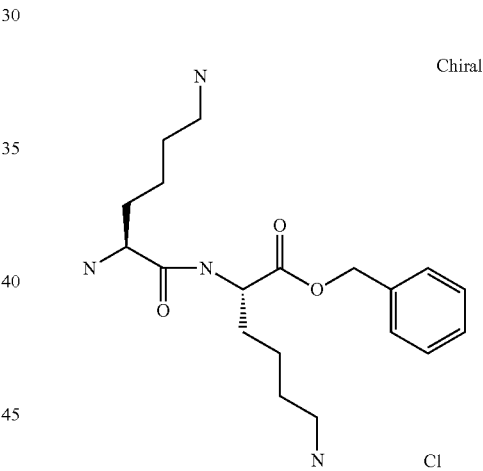

The above prepared (S)-2-((S)-2,6-bis-tert-butoxycarbonylamino-hexanoylamino)-6-tert-butoxycarbonylamino-hexanoic acid benzyl ester (4.516, 6.793 mmol) was dissolved in 4 mol/L HCl in dioxane. After a couple of min, gas evolved and a precipitate was formed. After 3 h at ambient temperature, the reaction mixture was carefully evaporated and scrupulously dried to yield 3.81 g of the title compound as an off-white foam which was used without further purification for Example 7. E. GalNAc Cluster benzyl ester above. MS (ISP): 365.3 $[M+H]^+$.

Example 9. Polynucleotide Targeting Moiety

The polynucleotide targeting moiety was made by attachment of a GalNAc cluster and a pharmacokinetic modulator to the amines on a lysine or ornithine scaffold molecule. The carboxyl group on the scaffold was then available for covalent attachment to the RNAi polynucleotide, such as an siRNA.

Example 10. GalNAc Cluster-Palmitoyl Targeting Moiety

A. (S)-2-(9H-Fluoren-9-ylmethoxycarbonylamino)-6-hexadecanoylamino-hexanoic acid benzyl ester

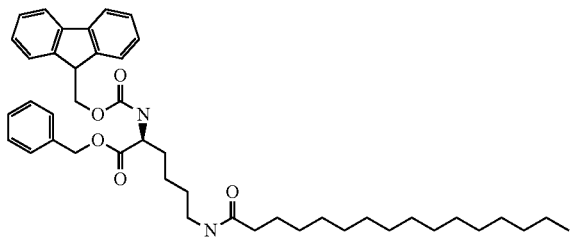 [SMILES: CCCCCCCCCCCCCCCC(=O)NCCCC[C@H](NC(=O)OCC1c2ccccc2-c2ccccc21)C(=O)OCc1ccccc1]

Commercially available Fmoc-Lys(palmitoyl)-OH (0.899 g, 1.481 mmol) was suspended in 15 mL of CH$_2$Cl$_2$ and successively treated with benzylic alcohol (0.320 g, 0.305 mL, 2.96 mmol, 2 eq.), hydroxybenzotriazol (HOBT, 0.268 g, 1.63 mmol, 1.1 eq.), 1-(3-dimethylaminopropyl)-3-ethylcarbodiimide.HCl (EDC, 0.312 g, 1.63 mmol, 1.1 eq.), and N-ethyl-diisopropylamine (0.224 g, 0.297 mL, 1.733 mmol, 1.17 eq.). The yellow solution was then stirred for 2 h. Pouring onto crushed ice/NH$_4$Cl solution, extraction with ethyl acetate, washing with water, drying over Na$_2$SO$_4$, and evaporation of all solvents, followed by flash chromatography (SiO$_2$, ethyl acetate/heptane=1/1) afforded 0.692 g of the title compound as an off-white solid. MS (ISP): 697.6 [M+H]$^+$.

B. (S)-2-Amino-6-hexadecanoylamino-hexanoic acid benzyl ester

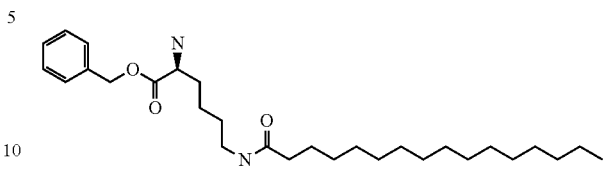

The above prepared (S)-2-(9H-Fluoren-9-ylmethoxycarbonylamino)-6-hexadecanoyl-amino-hexanoic acid benzyl ester (0.692 g, 0.993 mmol) was dissolved in 15 mL of THF and treated with 19 mL of diethylamine (~18 eq.). After 3 h at ambient temperature all volatiles were removed i.v. and the crude reaction mixture purified by flash chromatography (SiO$_2$, CH$_2$Cl$_2$/MeOH (10%)) to yield 0.355 g of the title compound as a white solid. MS (ISP): 475.3 [M+H]$^+$.

C.

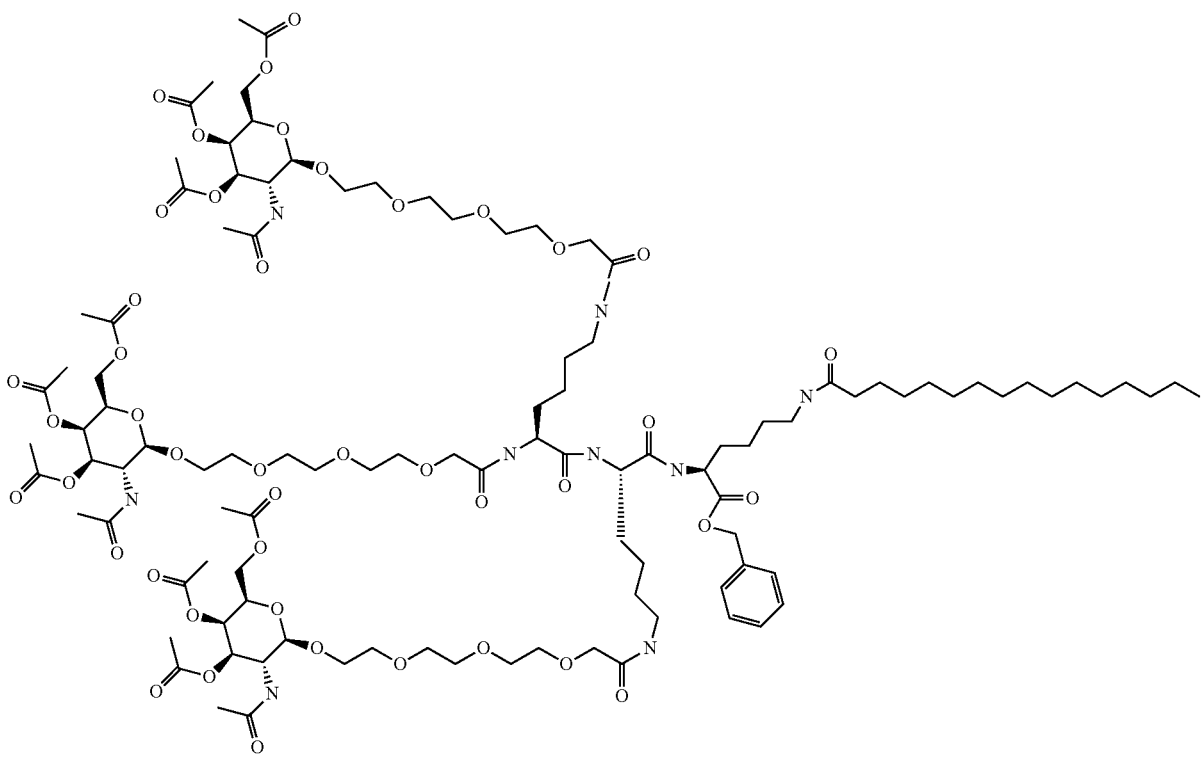 [SMILES: CCCCCCCCCCCCCCCC(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)OCc1ccccc1]

The above prepared GalNAc Cluster free acid (Example 7F.) (17S,20S)-1-((2R,3R,4R,5R,6R)-3-acetamido-4,5-diacetoxy-6-(acetoxymethyl)tetrahydro-2H-pyran-2-yloxy)-20-(1-((2R,3R,4R,5R,6R)-3-acetamido-4,5-diacetoxy-6-(acetoxymethyl)-tetrahydro-2H-pyran-2-yloxy)-11-oxo-3,6,9-trioxa-12-azahexadecan-16-yl)-17-(2-(2-(2-(2-((2R,3R,4R,5R,6R)-3-acetamido-4,5-diacetoxy-6-(acetoxymethyl)tetrahydro-2H-pyran-2-yloxy)ethoxy)ethoxy)-ethoxy)acetamido)-11,18-dioxo-3,6,9-trioxa-12,19-diazahenicosan-21-oic acid (0.185 g, 0.101 mmol) was dissolved in 2.0 mL of CH$_2$Cl$_2$ and successively treated with 1-hydroxy-7-azabenzotriazole (HOAt, 0.014 g, 0.101 mmol, 1 eq.), 1-(3-dimethylaminopropyl)-3-ethylcarbodiimide.HCl (EDC, 0.019 g, 0.101 mmol, 1 eq.), and N-ethyl-diisopropylamine (0.013 g, 0.017 mL, 0.101 mmol, 1 eq.). After stirring for 15 min. at ambient temperature, (S)-2-amino-6-hexadecanoylamino-hexanoic acid benzyl ester (0.048 g, 0.101 mmol, 1 eq.), dissolved in minimal $CH_2Cl_2$, was added and the reaction allowed to proceed for 2 h. The solvent was then evaporated and the crude mixture purified by flash chromatography ($SiO_2$, $CH_2Cl_2$/MeOH (7% to >10%)) to yield 0.133 g of the title compound as a white foam. MS (ISP): 1167.1 $[M+2Na]^{2+}/2$.

D.

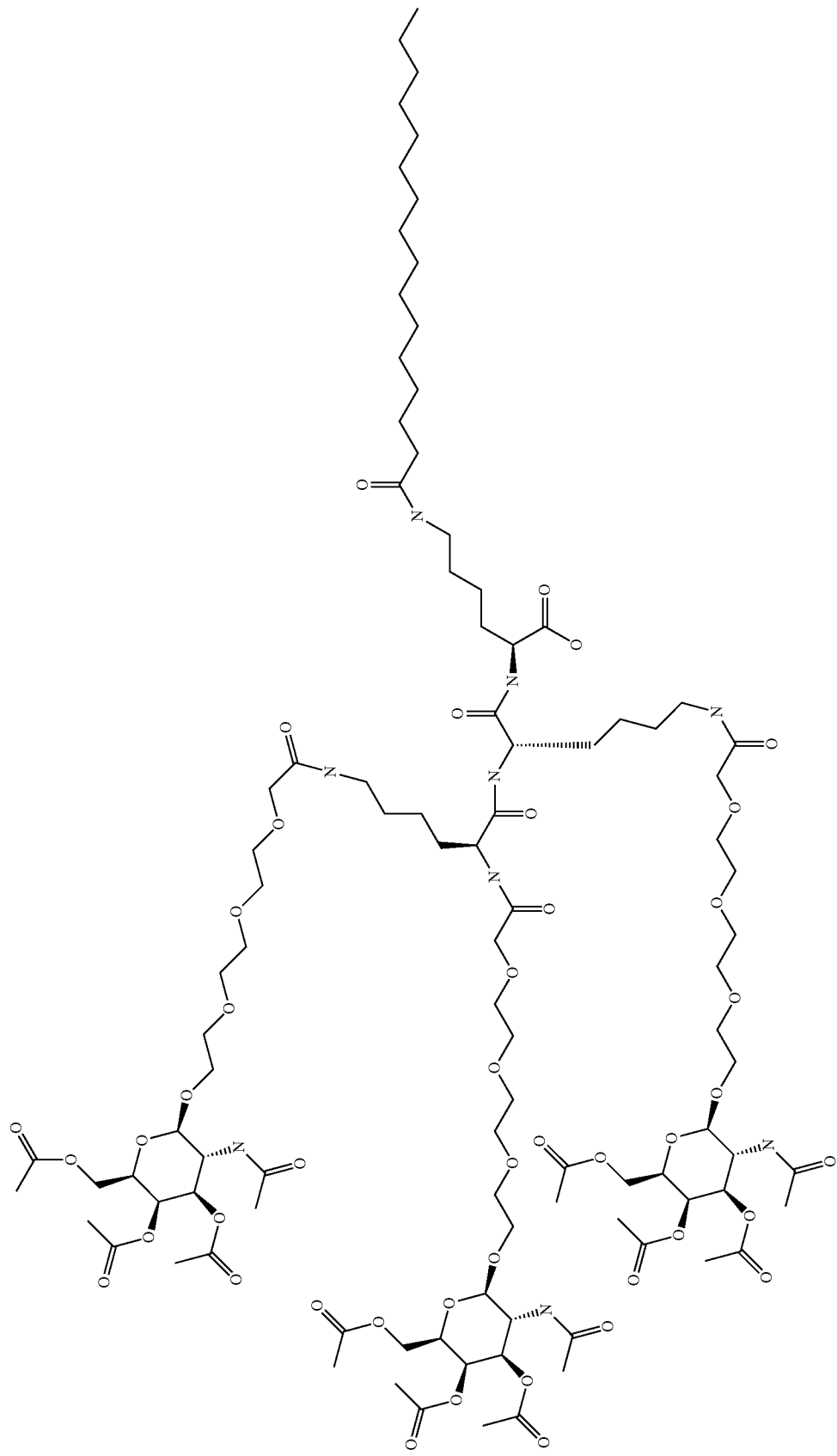

The above prepared benzyl ester (0.130 g, 0.057 mmol)) was dissolved in 5 mL of MeOH and hydrogenated over 0.024 g of Pd/C (10%) under 1 atm. of $H_2$ at ambient temperature for 3 h. Filtration over Celite and evaporation of the solvent left 0.123 g of the title compound as a colorless oil. MS (ISP): 2221.0 $[M+Na]^+$.

Example 11. Synthesis of GalNAc Cluster Palmitoyl with Ornithine Linker (C16)

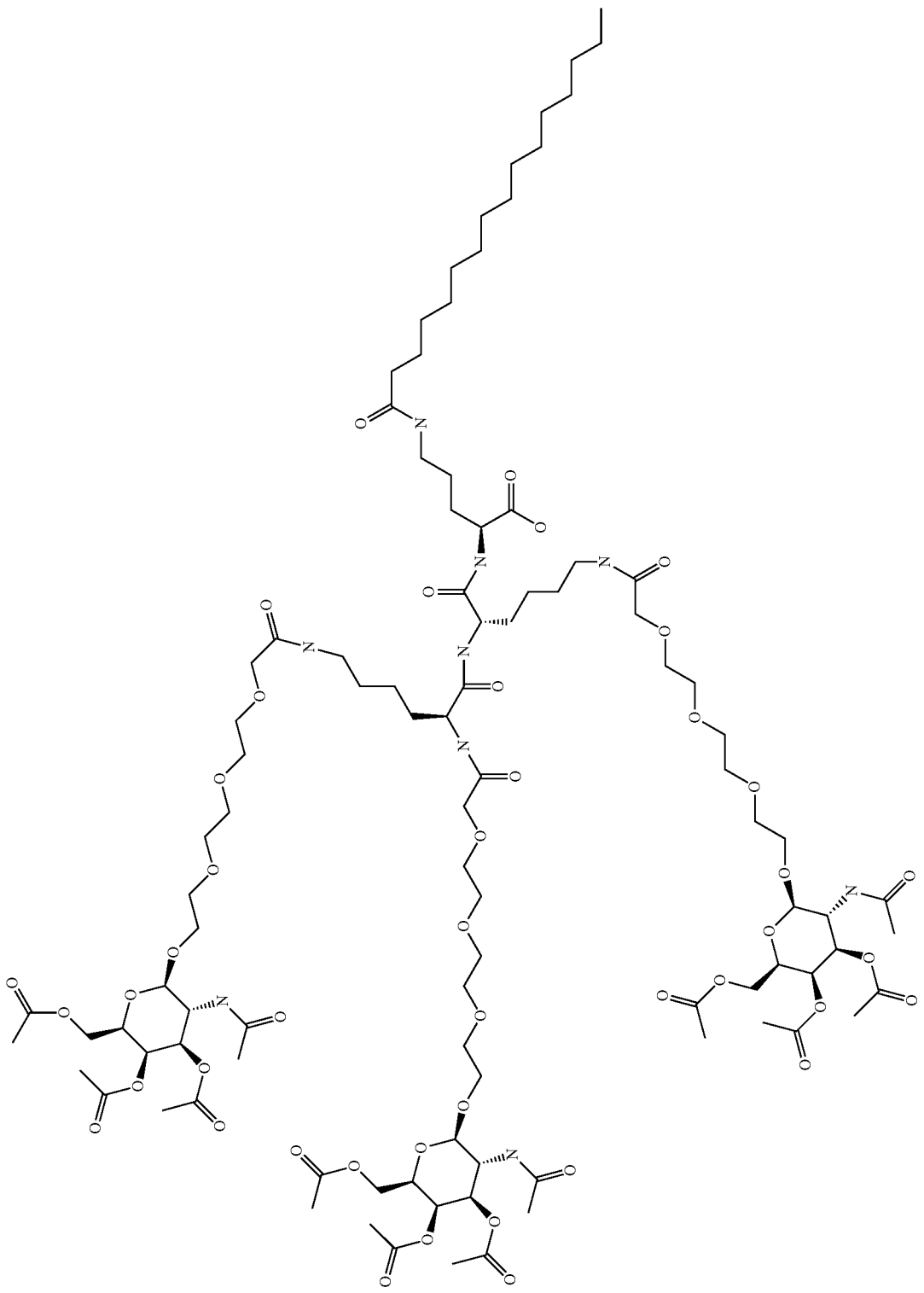

Prepared in analogy to example 10 but using Fmoc-L-Orn(palmitoyl)-OH instead of Fmoc-Lys(palmitoyl)-OH as white foam. MS (ISP): 1093.1 [M+2H]$^{2+}$/2.

Example 12. Synthesis of GalNAc Cluster (E)-hexadec-8-enoyl (C16)

A. (S)-2-(9H-Fluoren-9-ylmethoxycarbonylamino)-6-((E)-hexadec-8-enoylamino)-hexanoic acid 2-trimethylsilanyl-ethyl ester

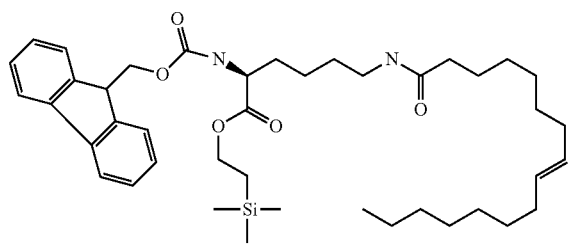 [SMILES: CCCCCCC/C=C/CCCCCCC(=O)NCCCC[C@H](NC(=O)OCC1c2ccccc2-c2ccccc21)C(=O)OCC[Si](C)(C)C]

Fmoc-Lys((E)-hexadec-8-enoyl)-OH (0.500 g, 0.827 mmol) was suspended in 15 mL of CH$_2$Cl$_2$ and successively treated with 2-(trimethylsilyl)ethanol (0.196 g, 0.236 mL, 1.65 mmol, 2 eq.), 1-hydroxy-7-azabenzotriazole (HOAt, 0.123 g, 0.909 mmol, 1.1 eq.), 1-(3-dimethylaminopropyl)-3-ethylcarbodiimide.HCl (EDC, 0.174 g, 0.909 mmol, 1.1 eq.), and N-ethyl-diisopropylamine (0.125 g, 0.164 mL, 0.967 mmol, 1.17 eq.). The yellow solution was then stirred over the weekend. Pouring onto crushed ice/HCl solution, extraction with ethyl acetate, washing with water, drying over Na$_2$SO$_4$, and evaporation of all solvents, followed by flash chromatography (SiO$_2$, CH$_2$Cl$_2$/MeOH=9/1) and crystallization from AcOEt/heptane delivered 0.488 g of the title compound as off-white semi-solid. MS (ISP): 705.6 [M+H]$^+$.

B. (S)-2-Amino-6-((E)-hexadec-8-enoylamino)-hexanoic acid 2-trimethylsilanyl-ethyl ester

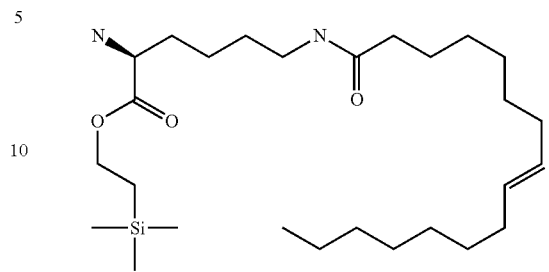

The above prepared (S)-2-(9H-fluoren-9-ylmethoxycarbonylamino)-6-((E)-hexadec-8-enoylamino)-hexanoic acid 2-trimethylsilanyl-ethyl ester (0.488 g, 0.690 mmol) was dissolved in 15 mL of THF and treated with 1.35 mL of diethylamine (~18 eq.). After 3 h at ambient temperature all volatiles were removed i.v. and the crude reaction mixture purified by flash chromatography (SiO$_2$, CH$_2$Cl$_2$/MeOH (10%)) to yield 0.259 g of the title compound as yellow oil. MS (ISP): 483.6 [M+H]$^+$.

C. GalNac Cluster (E)-hexadec-8-enoyl (C16)

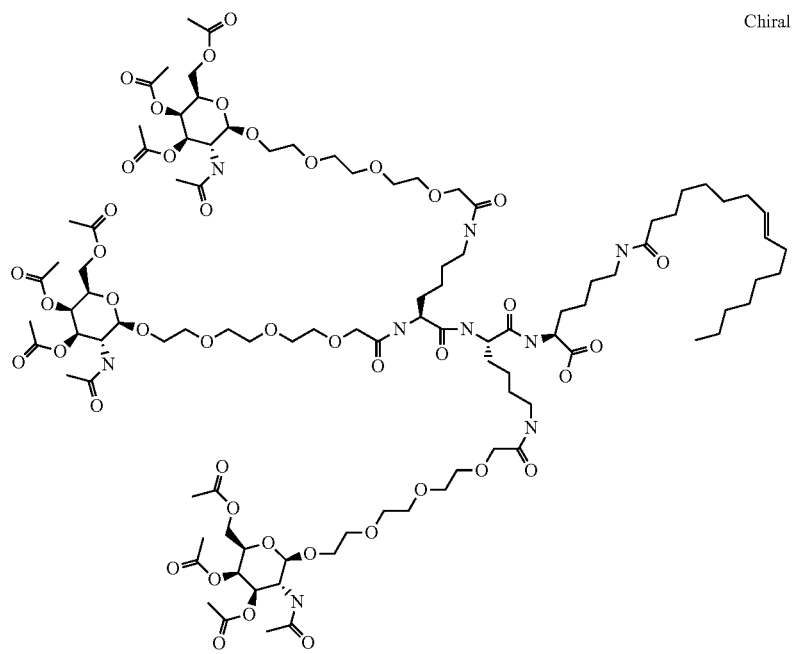 [SMILES: CCCCCCC/C=C/CCCCCCC(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)O]

The above compound was prepared as above using (S)-2-amino-6-((E)-hexadec-8-enoylamino)-hexanoic acid 2-trimethylsilanyl-ethyl ester and cleaving the protecting group as follows: After the penultimate step, the resultant 2-trimethylsilanyl-ethyl ester (245 mg, 0.107 mmol, Eq: 1.00) was combined with THF abs. (5 mL) to give a colorless solution. Tetrabutyl-ammonium fluoride trihydrate (168 mg, 0.533 mmol, Eq: 5.00) was added at 0° C. and the reaction was stored in the fridge over night. Pouring onto crushed ice, extraction with ethyl acetate, washing with water, drying over Na$_2$SO$_4$, and evaporation of all solvents yielded a sticky oil. Dissolution in acetonitrile and water and lyophilization afforded eventually 0.120 g of the title compound as white solid. MS (ISP): 1121.5 [M+2Na]$^{2+}$/2.

Example 13. Synthesis of GalNAc Cluster Oleyl (C18)

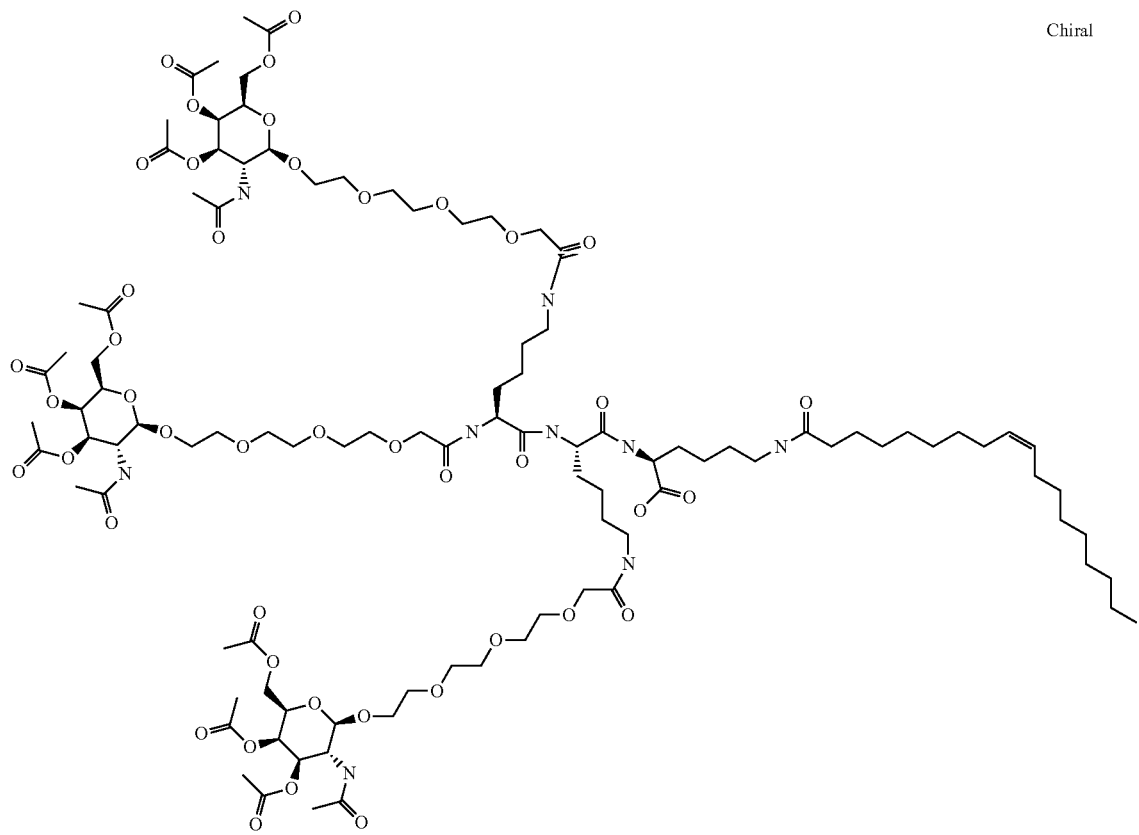 [SMILES: CCCCCCCC/C=C\CCCCCCCC(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)O]

Prepared in analogy to the example above but using (S)-2-(trimethylsilyl)ethyl 2-amino-6-oleamidohexanoate instead of (S)-2-amino-6-((E)-hexadec-8-enoylamino)-hexanoic acid 2-trimethylsilanyl-ethyl ester, as off-white foam. MS (ISP): 1113.6 [M+2H]$^{2+}$/2.

Example 14. Synthesis of GalNAc Cluster (9E,12E)-octadeca-9,12-dienoyl (C18)

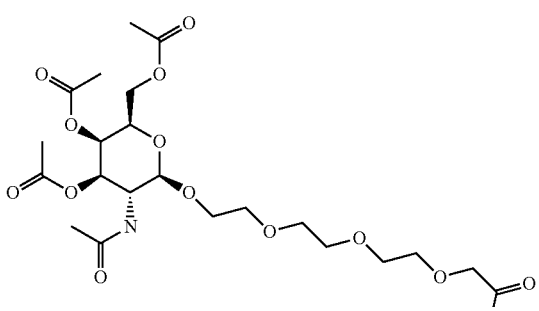

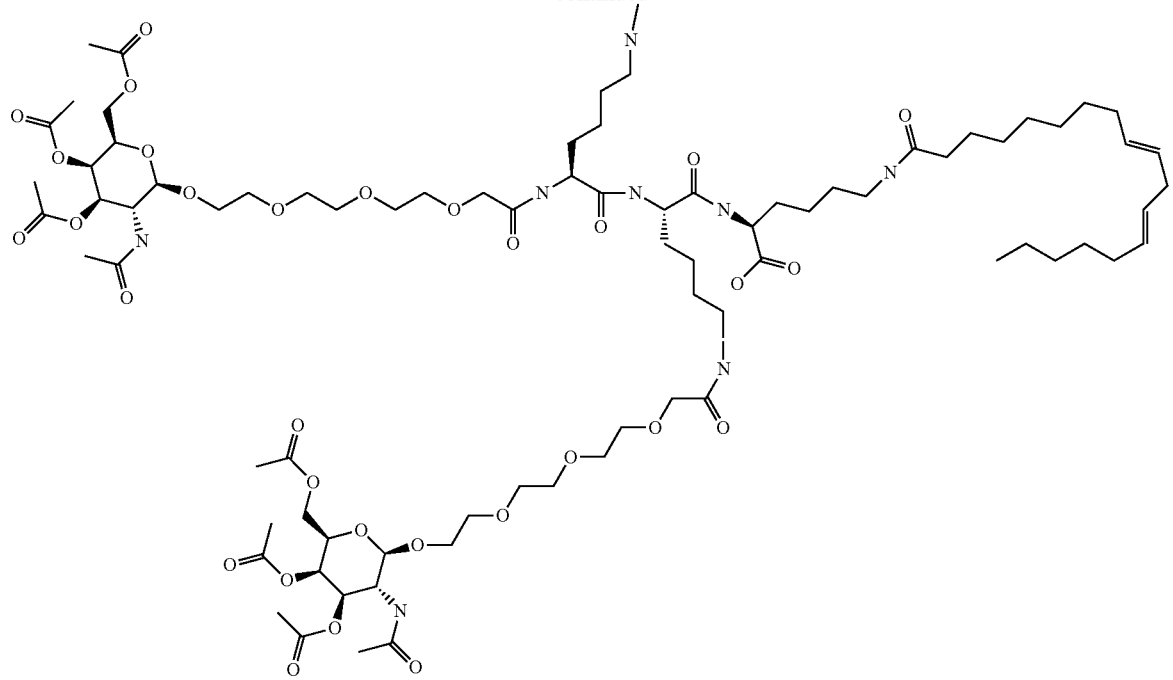
Prepared in analogy to the example above, but using (S)-2-(trimethylsilyl)ethyl 2-amino-6-((9E,12E)-octadeca-9,12-dienamido)hexanoate instead of (S)-2-amino-6-((E)-hexadec-8-enoylamino)-hexanoic acid 2-trimethylsilanyl-ethyl ester, as yellow lyophilized solid. MS (ISP): 1134.55 $[M+2Na]^{2+}/2$.
Example 15. Synthesis of GalNAc Cluster-Octanoyl (C8)
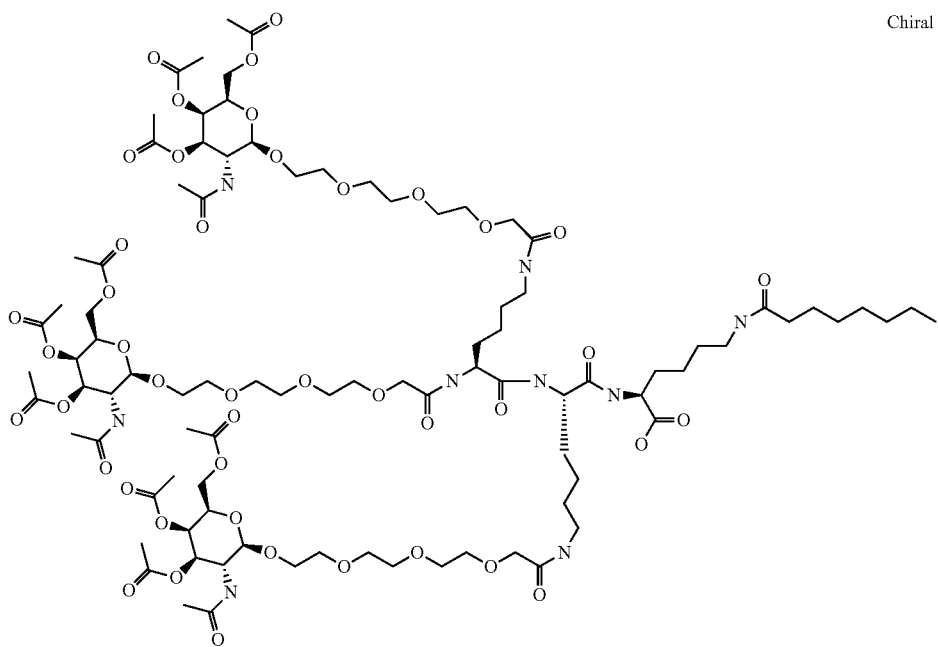 [SMILES: CCCCCCCC(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)O]

Prepared as described above, but using Fmoc-Lys(octanoyl)-OH instead of Fmoc-Lys(palmitoyl)-OH as light yellow foam. MS (ISP): 1044.5 [M+2H]$^{2+}$/2.

Example 16. Synthesis of GalNAc Cluster-Dodecanoyl (C12)

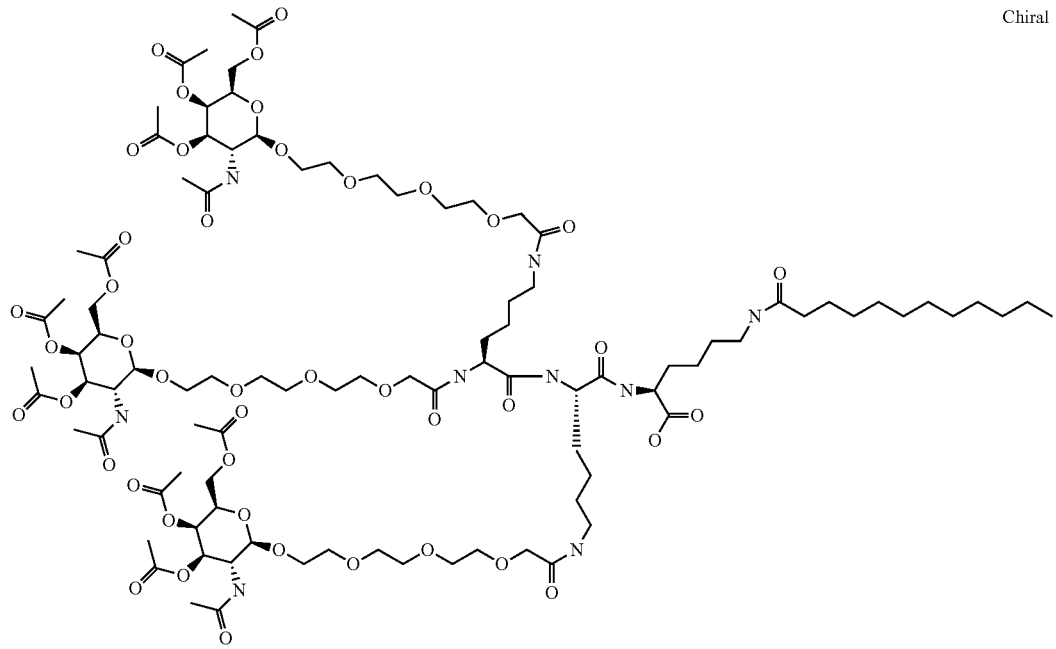 [SMILES: CCCCCCCCCCCC(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)O]

Prepared as described above but using Fmoc-Lys(dodecanoyl)-OH instead of Fmoc-Lys(palmitoyl)-OH as light yellow foam. MS (ISP): 2166.04 [M+Na]$^+$.

Example 17. Synthesis of GalNAc Cluster-C20-Acyl

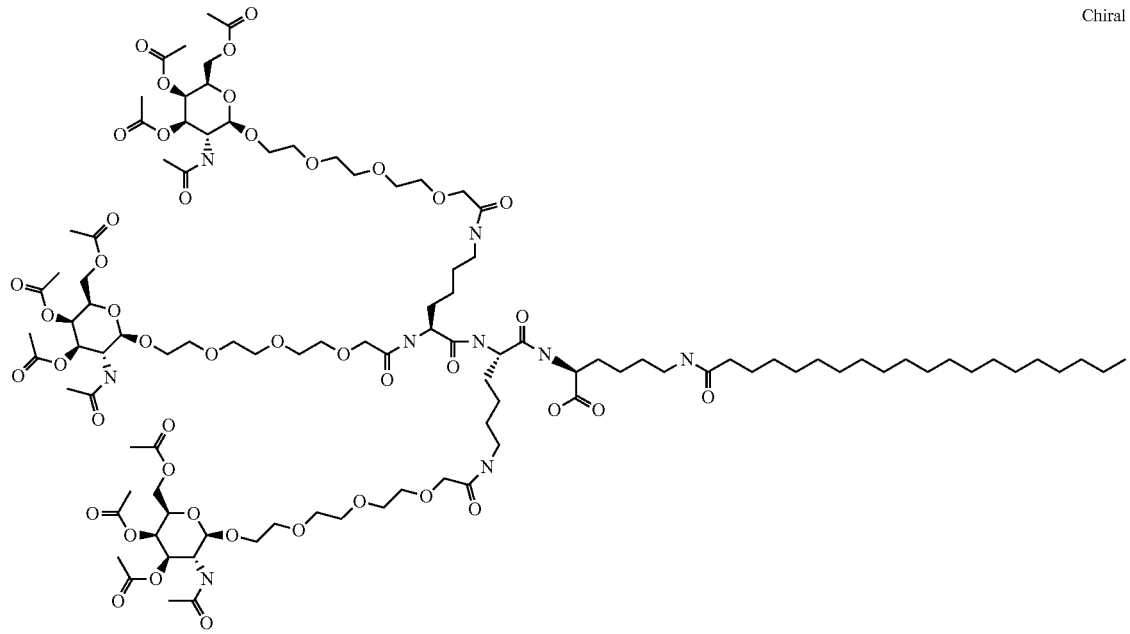 [SMILES: CCCCCCCCCCCCCCCCCCCC(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)O]

Prepared as described above but using Fmoc-Lys(icosanoyl)-OH instead of Fmoc-Lys(palmitoyl)-OH as light yellow foam. MS (ISP): 1150.58 [M+2Na]$^{2+}$/2.

Example 18. Synthesis of GalNAc Cluster-C24-Acyl

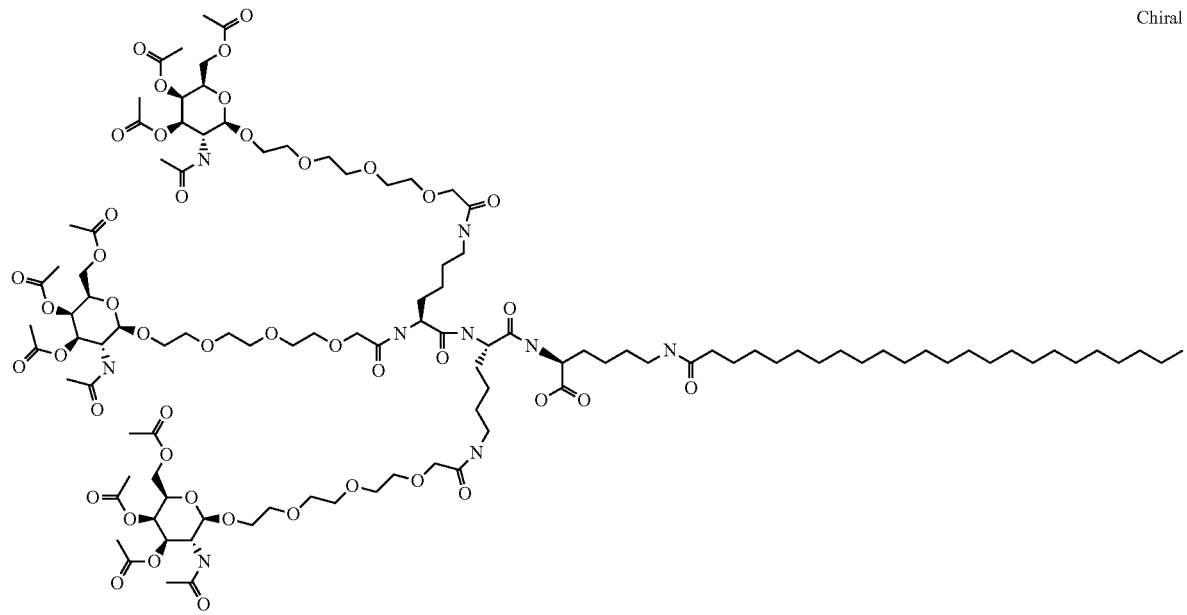 [SMILES: CCCCCCCCCCCCCCCCCCCCCCCC(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)O]

was prepared as described above but using Fmoc-Lys(tetracosanoyl)-OH instead of Fmoc-Lys(palmitoyl)-OH as light yellow foam. MS (ISP): 2312.24 [M+H]$^+$.

Example 19. Synthesis of GalNAc Cluster-Dioctanoyl (2×C8)

A. (S)-6-((S)-2,6-Bis-tert-butoxycarbonylamino-hexanoylamino)-2-(9H-fluoren-9-yl-methoxycarbonylamino)-hexanoic acid

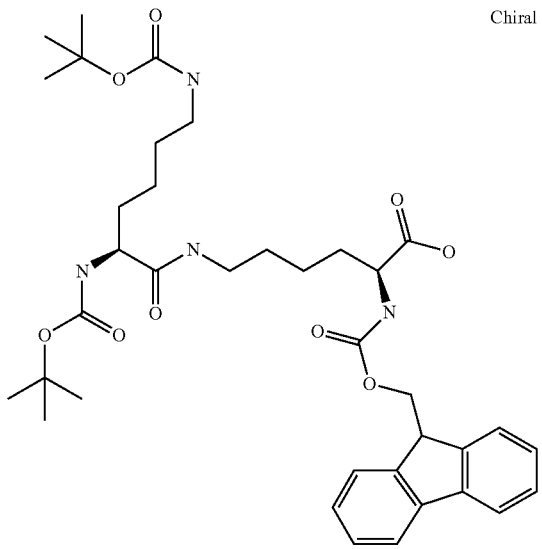 [SMILES: CC(C)(C)OC(=O)NCCCC[C@H](NC(=O)OC(C)(C)C)C(=O)NCCCC[C@H](NC(=O)OCC1c2ccccc2-c2ccccc21)C(=O)O]

In a round-bottomed flask, Fmoc-Lys-OH (1.393 g 3.78 mmol, Eq: 1.00) was dissolved in CH$_2$Cl$_2$ (16 mL) to give a light yellow solution. Huenig's base (1.955 g, 2.57 mL, 15.1 mmol, Eq: 4.00) and trimethylchlorosilane (0.863 g, 1.00 mL, 7.94 mmol, Eq: 2.10) were added and the reaction mixture was stirred for 20 min.

In a second round-bottomed flask, Boc-Lys(Boc)-OH (1.31 g, 3.78 mmol, Eq: 1.00) was dissolved in DMF (16 mL) to give a colorless solution. Huenig's base (0.587 mg, 0.77 mL, 4.54 mmol, Eq: 1.20) and TPTU [125700-71-2] (1.123 g, 3.78 mmol, Eq: 1.00) were added and the reaction mixture was stirred for 15 min. The solution from the first flask containing the corresponding silyl ester monosilylamine was then added and the reaction was stirred for another 2 hours. The mixture was poured onto crushed ice/NH$_4$Cl, extracted 2× with AcOEt, washed with H$_2$O and brine, dried over Na$_2$SO$_4$, and evaporated to dryness. Flash chromatography SiO$_2$ (8% MeOH in CH$_2$Cl$_2$) gave 2.324 g of the title compound as off-white foam. MS (ISP): 697.5 [M+H]$^+$, 719.4 [M+Na]$^+$.

B. (S)-6-((S)-2,6-Bis-tert-butoxycarbonylamino-hexanoylamino)-2-(9H-fluoren-9-ylmethoxy-carbonylamino)-hexanoic acid benzyl ester

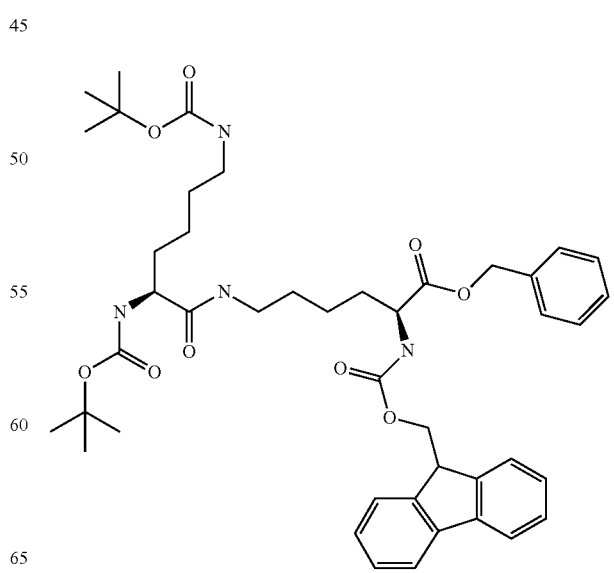

The above prepared (S)-6-((S)-2,6-bis-tert-butoxycarbonylamino-hexanoylamino)-2-(9H-fluoren-9-ylmethoxycarbonylamino)-hexanoic acid (2.32 g, 3.33 mmol, Eq: 1.00) and phenyl-methanol (0.720 g, 6.66 mmol, Eq: 2.00) were dissolved in 30 mL of $CH_2Cl_2$ and treated successively with 1-hydroxy-7-azabenzotriazole (HOAt, 0.498 g, 3.66 mmol, Eq: 1.10), 1-ethyl-3-(3-dimethylaminopropyl)carbodiimide hydrochloride (EDC, 0.702 g, 3.66 mmol, Eq: 1.10), and ethyl-diisopropyl-amine (0.503 g, 0.66 mL, 3.90 mmol, Eq: 1.17). After stirring for 120 minutes, the volatiles were removed i.v. Ensuing flash chromatography (8% MeOH in $CH_2Cl_2$) yielded 2.573 g of the title compound as light yellow waxy solid. MS (ISP): 787.5 $[M+H]^+$.

C. (S)-6-((S)-2,6-Diamino-hexanoylamino)-2-(9H-fluoren-9-ylmethoxycarbonylamino)-hexanoic acid benzyl ester

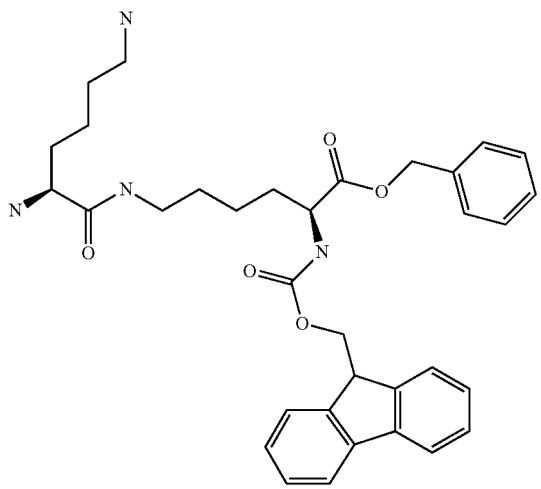 [SMILES: NCCCC[C@H](N)C(=O)NCCCC[C@H](NC(=O)OCC1c2ccccc2-c2ccccc21)C(=O)OCc1ccccc1]

The above prepared (S)-6-((S)-2,6-bis-tert-butoxycarbonylamino-hexanoylamino)-2-(9H-fluoren-9-ylmethoxycarbonylamino)-hexanoic acid benzyl ester (as hydrochloride, 0.613 g, 0.779 mmol, Eq: 1.00) was dissolved in dioxane (4 mL) and treated with 3.89 mL of 4 M HCl in dioxane (Eq: 10). After 3 h MS indicated the absence of starting material. All volatiles were removed i.v. to afford 0.519 g of the title compound as hydrochloride which was used without further purification for the next step. MS (ISP): 587.3 $[M+H]^+$.

D. (S)-6-((S)-2,6-Bis-octanoylamino-hexanoylamino)-2-(9H-fluoren-9-ylmethoxy-carbonylamino)-hexanoic acid benzyl ester

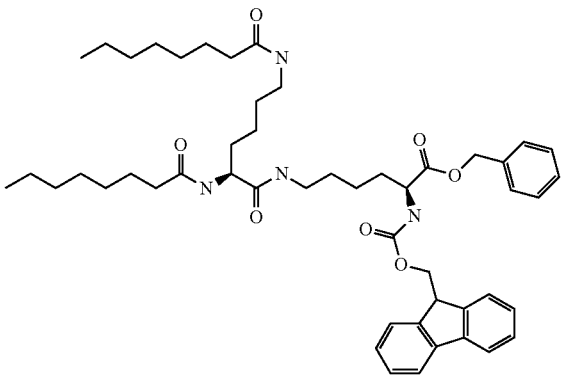 [SMILES: CCCCCCCC(=O)NCCCC[C@H](NC(=O)CCCCCCC)C(=O)NCCCC[C@H](NC(=O)OCC1c2ccccc2-c2ccccc21)C(=O)OCc1ccccc1]

The above prepared (S)-6-((S)-2,6-diamino-hexanoylamino)-2-(9H-fluoren-9-ylmethoxy-carbonylamino)-hexanoic acid benzyl ester (0.519 g, 0.771 mmol, Eq: 1.00) and caprylic acid (0.234 g, 1.619 mmol, Eq: 2.10) were dissolved in 12 mL of $CH_2Cl_2$ and treated successively with 1-hydroxy-7-azabenzotriazole (HOAt, 0.220 g, 1.619 mmol, Eq: 2.10), 1-ethyl-3-(3-dimethylaminopropyl)carbodiimide hydrochloride (EDC, 0.310 g, 1.619 mmol, Eq: 2.10), and ethyl-diisopropyl-amine (0.498 g, 0.666 mL, 3.855 mmol, Eq: 5.00). After stirring for 180 minutes, the mixture was poured onto crushed ice, extracted twice with AcOEt, washed with water, dried over $MgSO_4$, and evaporated to dryness. Crystallization from AcOEt/hexane yielded 0.453 g of the title compound as white solid. MS (ISP): 839.8 $[M+H]^+$, 861.8 $[M+Na]^+$.

E. (S)-2-Amino-6-((S)-2,6-bis-octanoylamino-hexanoylamino)-hexanoic acid benzyl ester

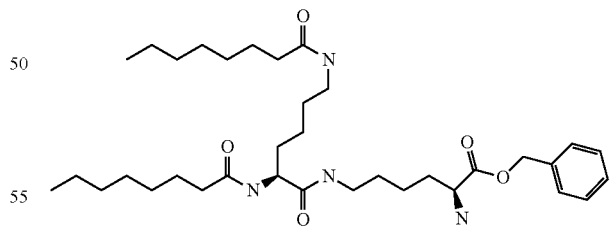

The above prepared (S)-6-((S)-2,6-bis-octanoylamino-hexanoylamino)-2-(9H-fluoren-9-ylmethoxycarbonylamino)-hexanoic acid benzyl ester (0.450 g, 0.536 mmol) was suspended in 2.2 mL of THF and treated with 2.2 mL of diethylamine (~40 eq.). After vigorously stirring at ambient temperature for 24 h, all volatiles were removed i.v. and the crude reaction product triturated twice with EtOEt to produce 0.258 g of the title compound as white solid. MS (ISP): 617.5 $[M+H]^+$.

F. GalNAc Cluster-Dioctanoyl (2×C8)

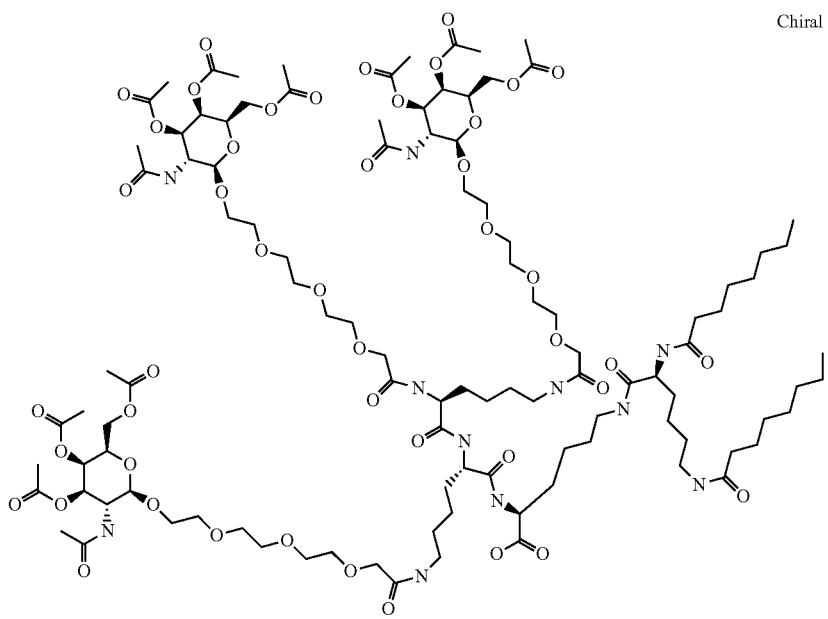 [SMILES: CCCCCCCC(=O)NCCCC[C@H](NC(=O)CCCCCCC)C(=O)NCCCC[C@H](NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)[C@H](CCCCNC(=O)COCCOCCOCCO[C@@H]1O[C@H](COC(C)=O)[C@H](OC(C)=O)[C@H](OC(C)=O)[C@H]1NC(C)=O)NC(=O)COCCOCCOCCO[C@@H]1O[C@H](COC(C)=O)[C@H](OC(C)=O)[C@H](OC(C)=O)[C@H]1NC(C)=O)C(=O)O]

Prepared as described above, but using (S)-2-amino-6-((S)-2,6-bis-octanoylamino-hexanoylamino)-hexanoic acid benzyl ester instead of (S)-2-amino-6-hexadecanoylamino-hexanoic acid benzyl ester as white foam. MS (ISP): 2342.19 [M+H]$^+$.

Example 20. Polynucleotide Targeting Moiety-siRNA Syntheses

A. Materials

Dry methanol (MeOH), sodium methylate, Amberlite IR-120, sodium sulfate, dry N,N-Dimethylformamide (DMF), dry dichloromethane (DCM), N,N'-Dicyclohexyl-carbodbmide (DCC), N-hydroxysuccinimide (NETS), N,N-Diisopropylethylamine (DIPEA) and sodium acetate solution (3 M, pH 5.2) were purchased from Sigma Aldrich Chemie GmbH (Taufkirchen, Germany). Triethylammonium acetate (TEAA) buffer (2.0 M, pH 7.0) and Acetonitrile (ACN) (HPLC quality) for RP-HPLC were purchased from Biosolve (Valkenswaard, Netherlands). Ethanol (EtOH) (p.a.) was purchased from Merck (Darmstadt, Germany). Purified water from a Optilab HF (Membra Pure, Germany) system was used. Resource RPC 3 mL column (10×0.64 cm; 15 µm particle size) was purchased from GE Healthcare (Freiburg, Germany). HPLC purification was accomplished using an ÄKTA Explorer 100 (GE Healthcare).

B. Synthesis of GalNAc Cluster-RNA Conjugate

Compound 1 (150 mg; 0.082 mmol) was dissolved in dry MeOH (5.5 mL) and 42 µL sodium methylate was added (25% solution in MeOH). The mixture was stirred under an argon atmosphere for 2 h at room temperature. An equal amount of methanol was added as well as portions of the cationic exchange resin Amberlite IR-120 to generate a pH around 7.0. The Amberlite was removed by filtration, the solution was dried over Na$_2$SO$_4$ and the solvent was removed under reduced pressure. Compound 2 was obtained in quantitative yield as a white foam. TLC (SiO$_2$, DCM/MeOH 5:1+0.1% CH$_3$COOH): R$_f$ 2=0.03; for detection a solution of sulfuric acid (5%) in MeOH was used, followed by heating. ESI-MS, direct injection, negative mode; [M−H]$^{-1}$$_{calculated}$: 1452.7; [M−H]$^{1-}$$_{measured}$: 1452.5.

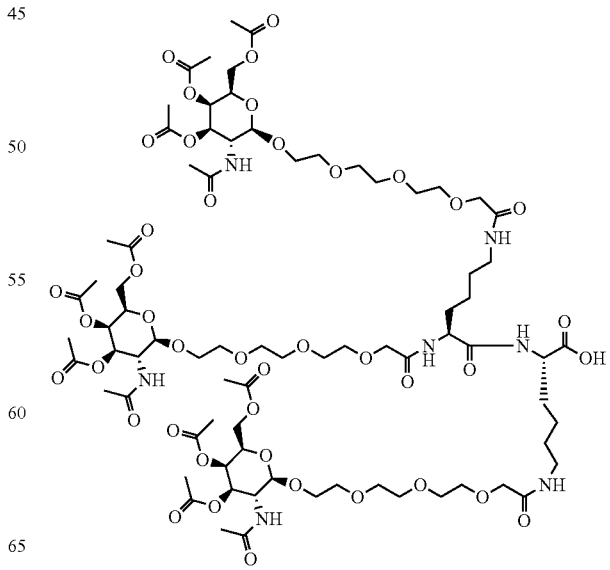

Compound 1

Compound 2

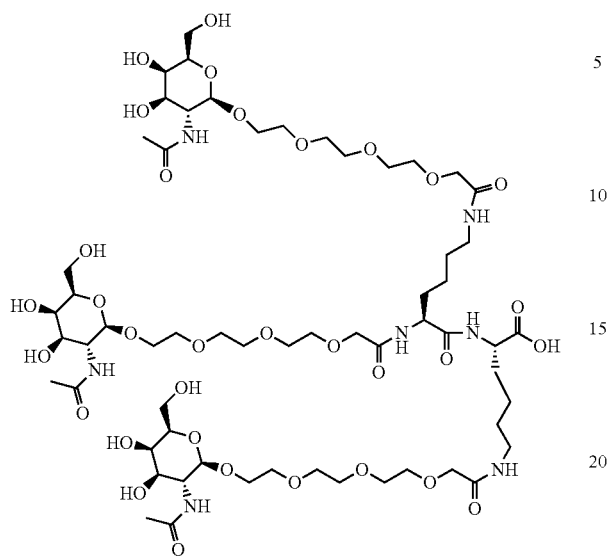

Compound 2 (20 mg; 0.014 mmol) was co-evaporated with pyridine and dichloromethane. The residue was dissolved in dry DMF (0.9 mL) and a solution of N-Hydroxysuccinimide in DMF (1.6 mg; 0.014 mmol) was added while stirring under an argon atmosphere. At 0° C. a solution of DCC in DMF (3.2 mg; 0.016 mmol) was slowly added. The reaction was allowed to warm to room temperature and stirred over night. Compound 3 was used without further purification for conjugation to RNA equipped with a C-6 amino linker, compound 4.

Compound 3

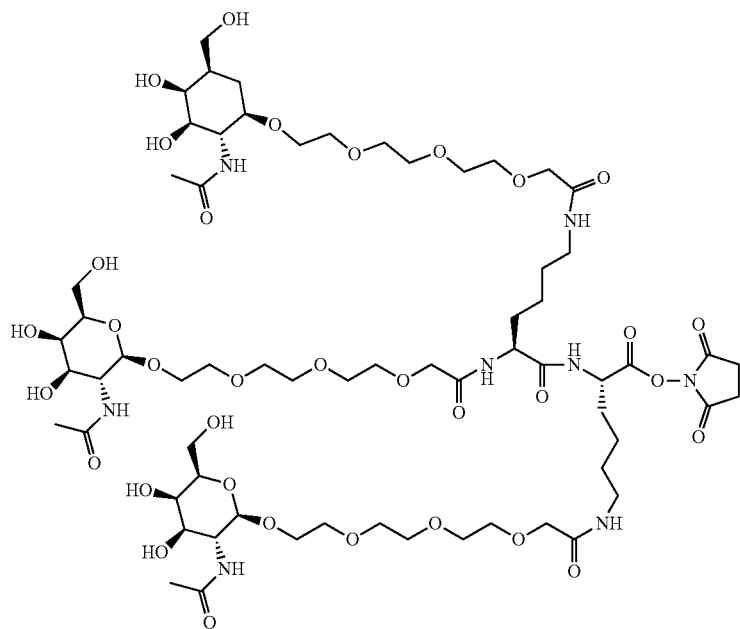

Compound 4

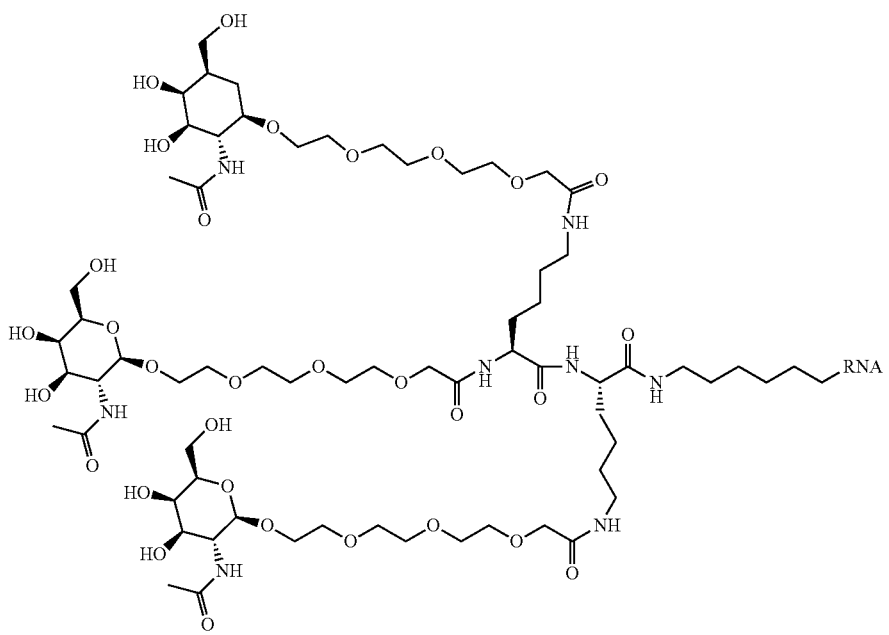

B. Synthesis of GalNAc Cluster-PK-RNA Conjugates

Compounds of the general structure represented by compound 1 were dissolved in dry MeOH and sodium methylate (9 equivalents) was added (25% solution in MeOH). The mixture was stirred under an argon atmosphere for 2 h at room temperature. The reaction mixture was diluted with methanol and subsequently portions of the cationic exchange resin Amberlite IR-120 were added to generate a pH around 7.0. The Amberlite was removed by filtration, the solution was dried with $Na_2SO_4$ and the solvent was removed under reduced pressure. Compounds of the general structure represented by compound 2 were obtained in quantitative yields as white foams.

Compound 1

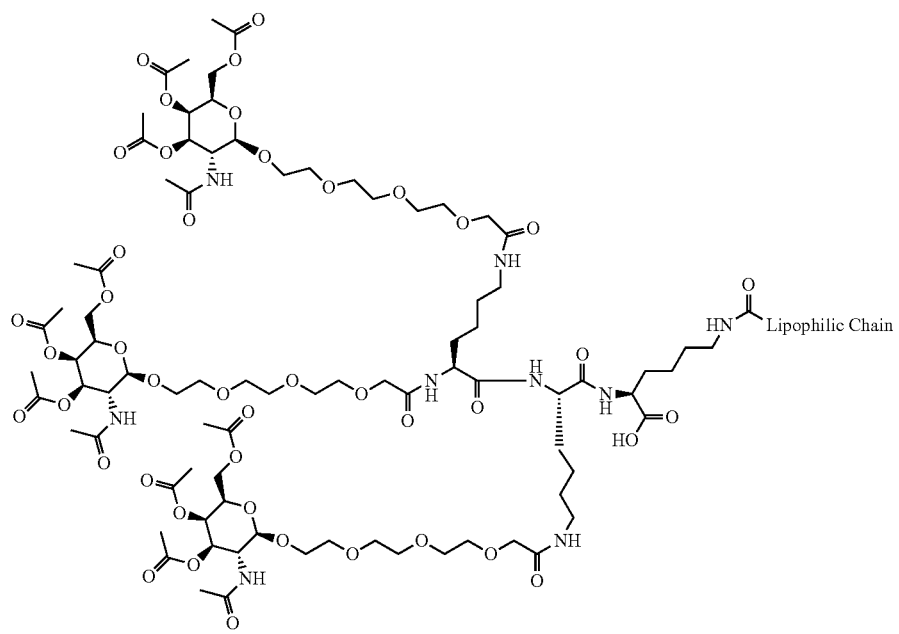

Compound 2

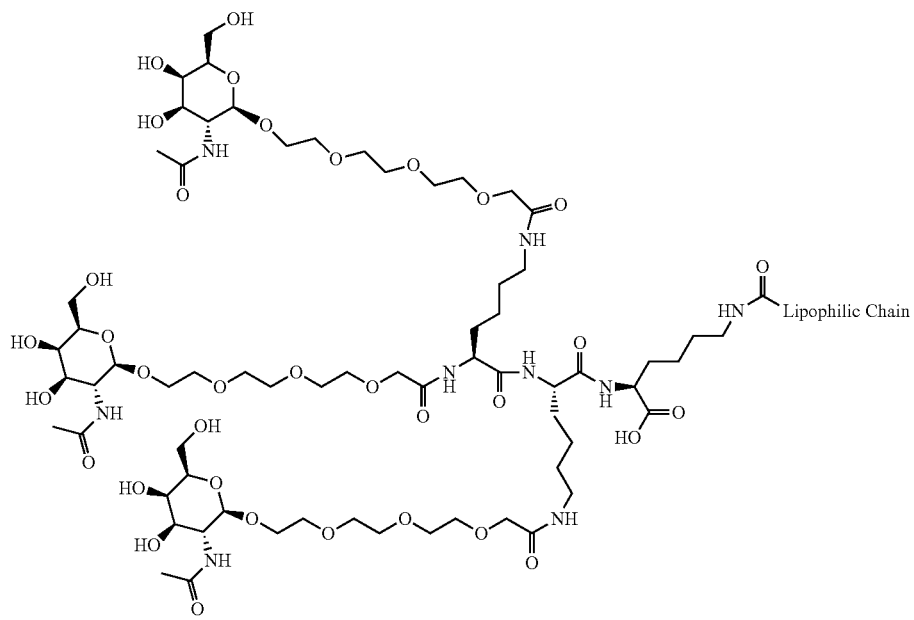

In the next step, Compounds of the general structure represented by compound 2 were activated by NHS formation. Compound 2 was co-evaporated with pyridine and dichloromethane. The residue was dissolved in dry DMF and a solution of N-Hydroxysuccinimide in DMF (1.0 equivalents) was added while stirring under an argon atmosphere. At 0° C. a solution of DCC in DMF (1.1 equivalents) was slowly added. The reaction was allowed to warm to room temperature and stirring was continued over night. The resultant activated compounds of the general structure represented by compound 3 were used without further purification for conjugation to RNA. The polynucleotide targeting moiety was conjugated to the 5'-ends of RNAs via a six carbon containing amino-linker (represented by compound 4).

Compound 3

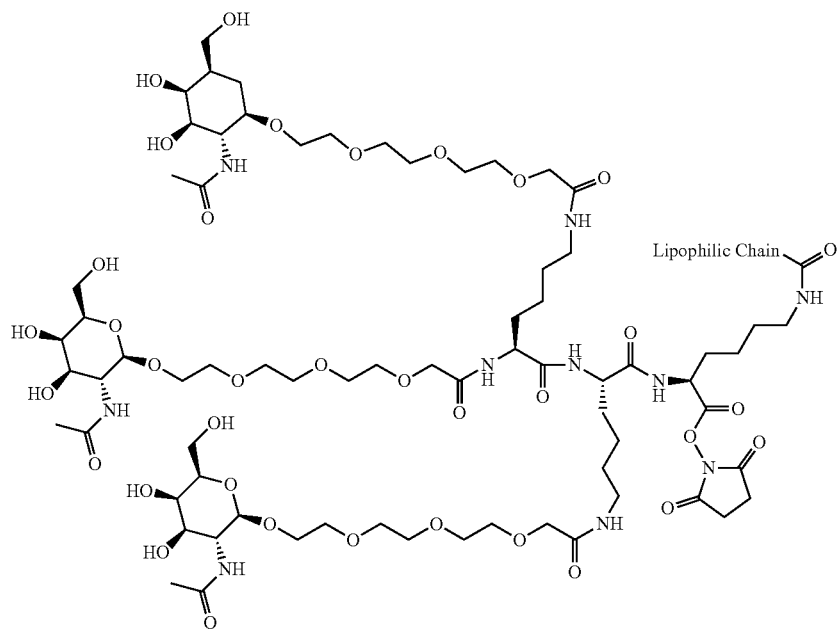

Compound 4
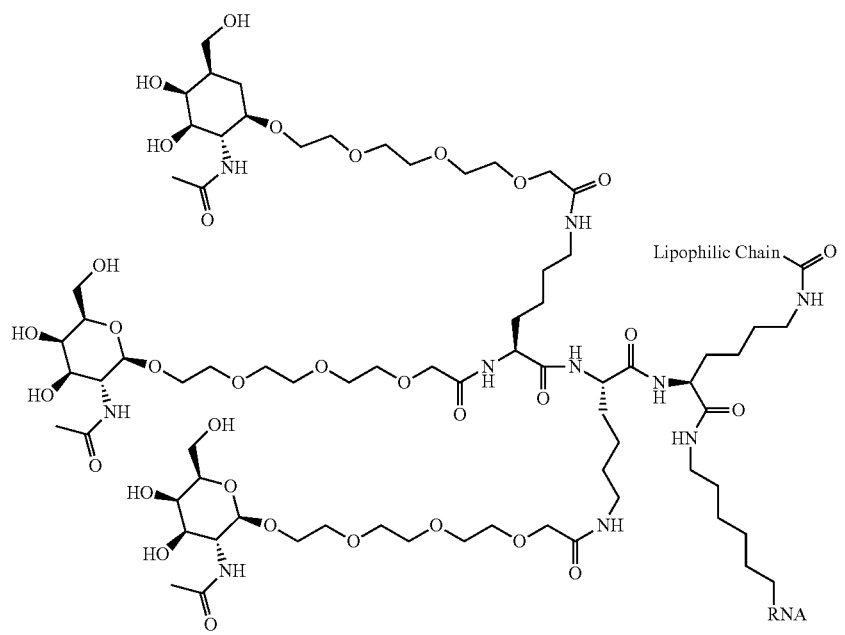
C. Synthesis of Amino-Modified RNA
RNA equipped with a C-6-aminolinker at the 5'-end of the sense strand was produced by standard phosphoramidite chemistry on solid phase at a scale of 1215 μmol using an ÄKTA Oligopilot 100 (GE Healthcare, Freiburg, Germany) and controlled pore glass as solid support (Prime Synthesis, Aston, Pa., USA). RNA containing 2'-O-methyl nucleotides were generated employing the corresponding phosphoramidites, 2'-O-methyl phosphoramidites and TFA-hexylaminolinker amidite (Sigma-Aldrich, SAFC, Hamburg, Germany). Cleavage and deprotection as well as purification was achieved by methods known in the field (Wincott F., et al, NAR 1995, 23, 14, 2677-84). The amino-modified RNA was characterized by anion exchange HPLC (purity: 96.1%) and identity was confirmed by ESI-MS ($[M+H]^{1+}_{calculated}$: 6937.4; $[M+H]^{1+}_{measured}$: 6939.0. Sequence: 5'-$(NH_2C_6)$GGAAUCuuAuAuuuGAUCcAsA-3' (SEQ ID NO: 1); u, c: 2'-O-methyl nucleotides of corresponding bases, s: phosphorthioate.

D. Synthesis of GalNAc Cluster RNA Conjugate (Compound 4)

RNA (2.54 μmol) equipped with a C-6 amino linker at the 5'-end was lyophilized and dissolved in 250 μL sodium borate buffer (0.1 M sodium borate, pH 8.5, 0.1 M KCl) and 1.1 mL DMSO. After addition of 8 μL DIPEA, a solution of compound 3 (theoretically 0.014 mmol) in DMF was slowly added to the RNA solution under continuous stirring. The reaction mixture was agitated at 35° C. over night. The reaction was monitored using RP-HPLC (Resource RPC 3 mL, buffer: A: 100 mM TEAA in water, B: 100 mM TEAA in 95% ACN, gradient: 5% B to 22% B in 20 CV). After precipitation of RNA using sodium acetate (3 M) in EtOH at −20° C., the RNA conjugate was purified using the conditions mentioned above. Pure fractions were pooled and the desired conjugate, compound 4, was precipitated using sodium acetate/EtOH. Compound 4 has been isolated in 59% yield (1.50 μmol). The purity of compound 4 was analyzed by anion exchange HPLC (purity: 91.7%) and identity was confirmed by ESI-MS ($[M+H]^{1+}_{calculated}$: 8374.4; $[M+H]^{1+}_{measured}$: 8376.5.

E. General Synthesis of GalNAc Cluster-PK-RNA Conjugates (Compound 4)

RNA equipped with a C-6 amino linker at the 5'-end was lyophilized from water and dissolved in a mixture of sodium borate buffer (0.1 M sodium borate, pH 8.5, 0.1 M KCl) and DMSO in a 1:4 ratio. After addition of DIPEA, a solution of compound 3 (6 equivalents) in DMF was slowly added under continuous stirring to the RNA solution. The reaction mixture was agitated at 35° C. over night. The reaction was monitored using RP-HPLC (Resource RPC 3 mL, buffer: A: 100 mM TEAA in water, B: 100 mM TEAA in 95% ACN, gradient: 5% B to 70% B in 20 CV). After precipitation of RNA using sodium acetate (3 M, pH 5.2) in EtOH at −20° C., the RNA conjugate was purified using the conditions mentioned above. The pure fractions were pooled and the desired conjugate of the general structure 4 was precipitated using sodium acetate/EtOH to give the pure RNA conjugate.

F. Annealing of siRNA

Compounds 4 with RNA sense strands were annealed with a 2'-O-methyl-modified anti sense RNA strands: Antisense sequence: 5'-uuGGAUcAAAu-AuAAGA-uUCcscsU-3' (SEQ ID NO: 2). The siRNA conjugates directed against the apolipoprotein B mRNA were generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. Duplex formation was confirmed by native gel electrophoresis.

In Vivo siRNA Delivery

Example 21. Administration of RNAi Polynucleotides In Vivo, and Delivery to Hepatocytes RNAi polynucleotide conjugates and masked polymers were synthesized as described above. Six to eight week old mice (strain C57BL/6 or ICR, ~18-20 g each) were obtained from Harlan Sprague Dawley (Indianapolis Ind.). Mice were housed at least 2 days prior to injection. Feeding was performed ad libitum with Harlan Teklad Rodent Diet (Harlan, Madison Wis.). RNAi polynucleotide conjugates and masked polymers were synthesized as described above. Mice were injected with 0.2 mL solution of delivery polymer and 0.2 mL siRNA conjugates into the tail vein. For simultaneous injection of polymer and siRNA, the siRNA-conjugate was added to modified polymer prior to injection and the entire amount, 0.4 ml, was injected. The composition was soluble and nonaggregating in physiological conditions. For injections in which polymer and siRNA are injected separately, polymer was injected in 0.2 mL of formulation solution and siRNA was injected in 0.2 mL of isotonic glucose. Solutions were injected by infusion into the tail vein. Injection into other vessels, e.g. retro-orbital injection, were equally effective.

Serum ApoB Levels Determination.

Mice were fasted for 4 h (16 h for rats) before serum collection by submandibular bleeding. Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm.

Plasma Factor VII (F7) Activity Measurements.

Plasma samples from mice were prepared by collecting blood (9 volumes) by submandibular bleeding into microcentrifuge tubes containing 0.109 mol/L sodium citrate anticoagulant (1 volume) following standard procedures. F7 activity in plasma is measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

Example 22

The siRNAs had the following sequences:
apoB siRNA:

```
sense
                                        (SEQ ID 1)
5' GGAAUCuuAuAuuuGAUCcAsA 3' antisense
                                        (SEQ ID 2)
5' uuGGAUcAAAuAuAAGAuUCcscsU 3'
``` factor VII siRNA

```
sense
                                            (SEQ ID 3)
5' GGAUfCfAUfCfUfCfAAGUfCfUfUfACfdTdT 3' antisense
                                            (SEQ ID 4)
5' GUfAAGACfUfUfGAGAUfGAUfCfCfdTsdT 3'
``` small letter=2'-O—CH$_3$ substitution
s=phosphorothioate linkage
f after nucleotide=2'-F substitution
d before nucleotide=2'-deoxy Galactose Cluster-PK Targeted siRNA Example 23. Delivery of siRNA to Hepatocytes In Vivo Using siRNA-Galactose Cluster-Pharmacokinetic Modulator Conjugates Co-Administered with Masked DW1360 Delivery Polymer siRNA and delivery polymer were prepared and administered as described using the indicated doses of siRNA and polymer.

A. Co-Administration of siRNA-Conjugates and Masked Lau 41305-38-17-19 Delivery Polymer Lau 41305-38-17-19 was modified with 7 weight equivalents of 2:1 CDM-PEG:CDM-NAG. Fully 2'F/MeO stabilized Factor VII siRNA was conjugated to GalNAc$_3$-palmitoyl targeting moiety or other indicated targeting moiety. Co-administration of siRNA-conjugate and Lau 41305-38-17-19 delivery polymer into 20 gm ICR mice (n=3) resulted in decreased serum Factor VII protein levels, indicating delivery of the siRNA to hepatocytes and inhibition of Factor VII gene expression. Efficient delivery required both the delivery polymer and targeting moiety conjugation to the RNAi polynucleotide (Table 2). No significant knockdown was observed with up to unconjugated siRNA. No target gene knockdown was observed in the absence of co-administered delivery polymer. The GalNAc$_3$-palmitoyl targeting ligand provided improved delivery of siRNA to liver cells compared to GalNAc$_3$ targeting moiety or cholesterol polynucleotide targeting moieties.

TABLE 2

Knockdown of target gene in vivo following injection of siRNA-GalNAc cluster conjugate plus delivery polymer, effect of polymer dose.

| Targeting moiety | siRNA dose [a] (mg/kg) | Polymer dose [a] (mg/kg) | Relative % Factor VII [b] |
|---|---|---|---|
| n/a | 0 | 0 | 100 ± 4 |
| n/a | 0 | 3 | 100 |
| GalNAc$_3$-palmitoyl | 2 | 0 | 100 |
| GalNAc | 2 | 3 | 100 |
| GalNAc$_3$ | 2 | 3 | 42 ± 5 |
| cholesterol | 2 | 3 | 68 ± 17 |
| GalNAc$_3$-palmitoyl | 2 | 3 | 21 ± 2 |

[a] mg siRNA or polymer per kilogram animal weight
[b] relative % protein

B. Co-Administration of siRNA-Conjugates and Masked Melittin Delivery Peptide

Tyr-Melittin was modified with 5 weight equivalents of CDM-NAG. Fully 2'F/MeO stabilized Factor VII siRNA was conjugated to GalNAc$_3$-palmitoyl targeting moiety or other indicated targeting moiety. Co-administration of siRNA-conjugate and Tyr-Melittin delivery peptide into 20 gm ICR mice (n=3) resulted in decreased serum Factor VII protein levels, indicating delivery of the siRNA to hepatocytes and inhibition of Factor VII gene expression. Efficient delivery required both the delivery peptide and targeting moiety conjugation to the RNAi polynucleotide (Table 3). No significant knockdown was observed with up to unconjugated siRNA. No target gene knockdown was observed in the absence of co-administered delivery polymer. The GalNAc$_3$-palmitoyl targeting ligand provided improved delivery of siRNA to liver cells compared to cholesterol polynucleotide targeting moiety.

TABLE 3

Knockdown of target gene in vivo following injection of siRNA-GalNAc cluster conjugate plus delivery polymer, effect of polymer dose.

| Targeting moiety | siRNA dose [a] (mg/kg) | Melittin dose [a] (mg/kg) | Relative % Factor VII [b] |
|---|---|---|---|
| n/a | 0 | 0 | 100 |
| n/a | 0 | 5 | 100 |
| GalNAc$_3$-palmitoyl | 5 | 0 | 100 |
| Cholesterol | 5 | 5 | 73 ± 14 |
| GalNAc$_3$-palmitoyl | 5 | 5 | 34 ± 11 |

[a] mg siRNA or peptide per kilogram animal weight
[b] relative % protein

C. Effect of Hydrophobic Group Size on Delivery of siRNA-Galactose Cluster-Pharmacokinetic Modulator Conjugates when Codelivered with Masked DW1360 Delivery Polymer DW1360 was modified with 7 weight equivalents of 2:1 CDM-PEG:CDM-NAG. Fully 2'F/MeO stabilized apoB siRNA was conjugated to GalNAc$_3$-PK targeting moieties having the indicated hydrophobic PK group. Co-administration of siRNA-conjugate and DW1360 delivery peptide into 20 gm ICR mice (n=3) resulted in decreased serum ApoB protein levels, indicating delivery of the siRNA to hepatocytes and inhibition of ApoB gene expression. Efficient delivery required both the delivery peptide and targeting moiety conjugation to the RNAi polynucleotide (Table 4). Optimal delivery was observed with polynucleotide targeting ligands having PK groups with 16-20 carbon atoms (hydrophobic groups having 15-19 carbon atoms).

TABLE 4

Knockdown of target gene in vivo following injection of siRNA-GalNAc cluster conjugate plus delivery polymer, effect of polymer dose.

| PK modulator | PK carbon number | siRNA dose [a] (mg/kg) | polymer dose [a] (mg/kg) | Relative % ApoB [b] |
|---|---|---|---|---|
| n/a | | 0 | 0 | 100 |
| none | — | 0.25 | 12.5 | 47 ± 17 |
| Octanoyl | 8 | 0.25 | 12.5 | 52 ± 3 |
| Dodecanoyl | 12 | 0.25 | 12.5 | 41 ± 8 |
| (E)-hexadec-8-enoyl | 16 | 0.25 | 12.5 | 27 ± 12 |
| Dioctanoyl | 16 | 0.25 | 12.5 | 25 ± 6 |
| palmitoyl | 16 | 0.25 | 12.5 | 21 ± 7 |
| Oleyl | 18 | 0.25 | 12.5 | 21 ± 2 |

TABLE 4-continued

Knockdown of target gene in vivo following injection of siRNA-GalNAc cluster conjugate plus delivery polymer, effect of polymer dose.

| PK modulator | PK carbon number | siRNA dose [a] (mg/kg) | polymer dose [a] (mg/kg) | Relative % ApoB [b] |
|---|---|---|---|---|
| (9E,12E)-octadeca-9,12-dienoyl | 18 | 0.25 | 12.5 | 21 ± 9 |
| C20-Acyl | 20 | 0.25 | 12.5 | 19 ± 8 |
| C24-Acyl | 24 | 0.25 | 12.5 | 44 ± 5 |

[a] mg siRNA or polymer per kilogram animal weight
[b] relative % protein

Example 24. Biodistribution of siRNA-GalNAc Cluster PK Administered In Vivo

Six different GalNAc cluster-PK targeting moieties comprising various hydrophobic side chains were covalently conjugated to an siRNA directed against ApoB. These conjugates were administered intravenously (i.v. bolus) into male Wistar rats at a dose of 2.5 mg/kg (Table 5). Blood samples were collected from different animals 5, 15, 30, 60, 90, 120, 240 and 360 min post dosing (n=2 for each time point). Immediately after blood draw EDTA plasma was generated which was subsequently treated with proteinase K (Epicentre Biotechnologies, USA). Liver and spleen tissue samples (500 mg) were harvested 1.5 and 6 h post dosing from sacrificed animals (n=2). Frozen tissue pieces were grinded to give a fine powder. An aliquot of each tissue was weighed and homogenized using Lysis Mixture (Panomics, USA), Proteinase K (Epicentre Biotechnologies, USA) and a SONOPULS HD 2070 (Bandelin, Germany) ultrasound homogenizer. The resulting final tissue lysates had concentrations of ~50 mg/mL.

The siRNA concentration in the plasma and tissue samples was determined using a proprietary oligonucleotide detection method. Briefly, the siRNA quantification was based on the hybridization of a complementary fluorescently (Atto-425) labeled PNA-probe with the antisense strand of the siRNA duplex and AEX-HPLC based separation. Quantification was done by fluorescence detection against an external calibration curve, that was generated from a dilution series of the corresponding non-conjugated ApoB duplex. This duplex was comprised of the identical antisense strand common for all conjugates tested in the PK experiment. Plasma samples (0.2-2 μL) and tissue samples (~1 mg) were injected onto the HPLC system.

The tissue results are shown in Table 5 for liver. In liver the lowest concentration was found siRNA having a targeting moiety lacking a PK modulator (no additional hydrophobic chain). siRNA concentrations were higher in liver for all the conjugates that bore a hydrophobic side chain PK modulator on the targeting moiety. The highest concentration after 1.5 hours was determined for the targeting moiety having two octanoyl side chains in addition to the GalNAc cluster. At 6 h post dosing, the targeting moiety having a $C_{20}$-acyl side chain in addition to the GalNAc cluster displayed the highest liver concentration. Therefore, liver uptake of GalNAc-conjugated siRNAs can be increased by modulating the PK properties when hydrophobic side chains are engineered into the targeting moiety.

Although the specific mechanism is not known, it is possible that the PK modulators resulted in increased plasma protein binding and therefore increased circulation time. Increased circulation time then led to increased tissue targeting. Conversely, in the absence of the PK modulator, the siRNA was more rapidly cleared from circulation by renal filtration.

Figure 7:
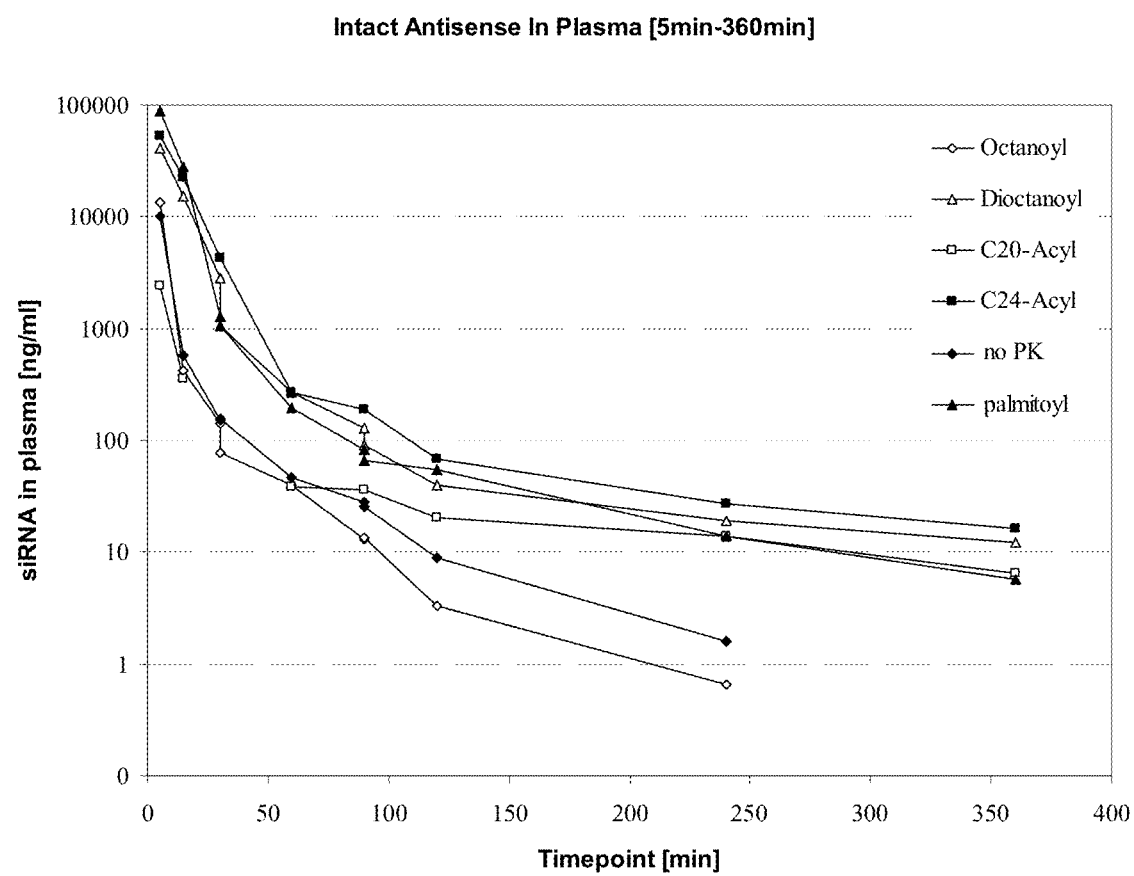
FIG. 7. Graph illustrating persistence in plasma of siRNA linked to various pharmacokinetic modulators.

The distribution properties can be partially correlated with the hydrophobicity of the side chains. No PK modulator and C8 PK modulator were more rapidly cleared from circulation, had the lowest liver targeted distribution, and exhibited the least target gene knockdown. In contrast, the presence of PK modulators having 16-20 carbon atoms were less rapidly cleared from circulation, had higher liver targeted distribution, and exhibited the increased target gene knockdown (FIG. 7).

TABLE 5 siRNA in liver 1.5 hours after administration

| Polynucleotide targeting moiety | siRNA in liver (ng/g)[a] |
|---|---|
| GalNAc cluster (C8) | 396 ± 204 |
| GalNAc cluster (2x C-8) | 2463 ± 1014 |
| GalNAc cluster (C20) | 1725 ± 1753 |
| GalNAc cluster (C24) | 767 ± 25 |
| GalNAc cluster (C-16) | 990 ± 326 |
| GalNAc-Cluster | 189 ± 22 |

[a] 1.5 h after injection

Example 25. Increased Tumor Targeting Through Use of a Pharmacokinetic Modulator siRNA were conjugated to either folate or cholesterol alone or to a folate-cholesterol pharmacokinetic modulator. 5 mg siRNAs were injected into KB xenograft mice. Tumors were then isolated and assayed for siRNA presence. Two (2) hours after injection, significantly more siRNA was found in the tumors for the siRNA conjugated to the folate-cholesterol pharmacokinetic modulator (>500 ng/g) than compared to siRNA conjugated to either folate or cholesterol alone (less than 100 ng/g). At six (6) hours post injection, the difference was even more pronounced, ~500 ng/g vs. <50 ng/g.

KB Xenograft Model:

KB cells were obtained from ATCC and grown in Folate free RPMI 1640 medium (#27016) from GIBCO/Invitrogen supplemented with 10% FBS. KB cells should be cultured in folate free medium for at 2 weeks before injection into host mice. Athymic Nude-Foxn1[nu] (Fox Chase Nude) were obtained from Harlan laboratory. The mice are fed folate free chow (DYET#17772, from Dyets Inc., Bethlehem, Pa. 18017) from 2-3 weeks before tumor inoculation and thereafter. Subconfluence KB cells are trypsinized, rinsed with PBS and suspended in PBS at 1 million/100 μl. 1-2 million cells were injected subcutaneously under the left flank and monitor tumor growth was monitored twice per week with digital calipers. Mice were injected with siRNA when tumors were between 5-8 mm in size and therefore predicted be well vascularized (typically 7-10 days).

siRNA Quantification:

Tissue samples were pulverized in frozen state and 15-25 mg frozen powder was suspended in 1 mL 1:3 Lysis Solution (Panomics/Affymetrix) diluted in nuclease-free water. Samples were sonicated with an ultrasonic stick and subsequently treated with Proteinase K (Panomics/Affymetrix) for 30 minutes at 65° C. After Proteinase K treatment, 20 μL 3M KCl was added to 200 μL tissue sonicate to precipitate the SDS. Samples are placed on ice for 10 minutes, and subsequently centrifuged for 15 minutes at 4000 rcf at 4° C. Supernatant was collected for siRNA quantification. 100 μL supernatant was mixed with 5 μL of 10 μM Atto610-PNA-probe solution targeting the antisense strand. Hybridization buffer (50 mM TRIS-Cl, pH 8.0) was added to a final volume of 200 μL. Samples are incubated in a thermal cycler at 95° C. for 15 minutes, then allowed to hybridize by reducing the temperature to 50° C. and further incubating 15 minutes. Calibration curves were generated from a siRNA dilution series under identical conditions, and all samples were then put into an HPLC autosampler. Samples were injected at a volume of 100 μL onto a Dionex DNAPac PA-100 4×250 mm column heated at 50° C. Sample was eluted using a binary gradient at a flow rate of 1 mL/min. Buffer A: 10 mM Tris, 30% ACN, 100 mM NaCl, pH 7. Buffer B: 10 mM Tris, 30% ACN, 900 mM NaCl, pH 7. Samples were analyzed using a Shimadzu RF-10Axl Fluorescence Detector (ex: 436 nm, em: 484 nm).

The invention claimed is:

1. A composition for delivering an RNA interference polynucleotide to a liver cell in vivo comprising the structure represented by:

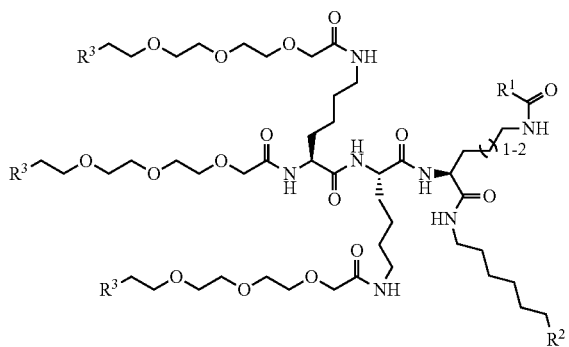

wherein $R^1$ comprises a hydrophobic group having 16 or more carbon atoms, $R^2$ comprises the RNA interference polynucleotide, and $R^3$ comprises a galactose or galactose derivative having affinity for the asialoglycoprotein receptor equal to or greater than that of galactose.

2. The composition of claim 1 wherein $R^1$ comprises cholesterol.

3. The composition of claim 1 wherein $R^1$ comprises hexadec-8-enoyl.

4. The composition of claim 1 wherein $R^1$ comprises oleyl.

5. The composition of claim 1 wherein $R^1$ comprises (9E,12E)-octadeca-9,12-dienoyl.

6. The composition of claim 1 wherein $R^1$ comprises dioctanoyl.

7. The composition of claim 1 wherein $R^1$ comprises C16-C20 acyl.

8. The composition of claim 7 wherein $R^1$ comprises C16 acyl.

9. The composition of claim 7 wherein $R^1$ comprises C18 acyl.

10. The composition of claim 7 wherein $R^1$ comprises C80 acyl.

11. The composition of claim 1 wherein $R^3$ comprises: galactosamine, N-formyl-galactosamine, N-acetylgalactosamine, N-propionyl-galactosamine, N-n-butanoyl-galactosamine, or N-iso-butanoylgalactosamine.

12. The composition of claim 1 wherein $R^3$ comprises N-formyl-galactosamine.

13. The composition of claim 1 wherein $R^3$ comprises N-acetylgalactosamine.

14. The composition of claim 1 wherein $R^3$ comprises N-propionyl-galactosamine.

15. The composition of claim 1 wherein $R^3$ comprises N-n-butanoyl-galactosamine.

16. The composition of claim 1 wherein $R^3$ comprises N-iso-butanoylgalactosamine.

17. The composition of claim 1 wherein the composition further comprises a polynucleotide delivery polymer.

18. The composition of claim 17 wherein the polynucleotide delivery polymer comprises a reversibly modified membrane active polyamine.

19. The composition of claim 1 wherein $R^2$ comprises: DNA, RNA, dsRNA, siRNA, or miRNA.

20. The composition of claim 1 wherein $R^2$ comprises siRNA.

* * * * *